US006521416B1

United States Patent
Birken et al.

(10) Patent No.: US 6,521,416 B1
(45) Date of Patent: Feb. 18, 2003

(54) DETERMINATION OF THE AMOUNT OF HLHβ CORE FRAGMENT IN A SAMPLE FROM A SUBJECT AND USES THEREOF

(75) Inventors: Steven Birken, Dumont, NJ (US); Yacov Maydelman, Fort Lee, NJ (US); Galina I. Kovalevskaya, New York, NY (US); John F. O'Connor, New Rochelle, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/630,273

(22) Filed: Aug. 1, 2000

Related U.S. Application Data

(63) Continuation of application No. PCT/US99/02279, filed on Feb. 3, 1999, and a continuation-in-part of application No. 09/018,122, filed on Feb. 3, 1998.

(51) Int. Cl.[7] ............................. C12Q 1/58; C12Q 1/00; G01N 33/53; G01N 33/537
(52) U.S. Cl. .................... 435/12; 435/7.1; 435/7.92; 435/4
(58) Field of Search ........................... 435/7.1, 4, 7.92, 435/12

(56) References Cited

U.S. PATENT DOCUMENTS 4,503,143 A * 3/1985 Gerber et al. ................ 435/7
4,851,356 A * 7/1989 Canfield et al. ............ 436/510

OTHER PUBLICATIONS

Birken et al. Metabolism of hCG and hLH to multiple urinary forms. Molecular and Cellular Endocrinology 125:121–131 (1996).*

* cited by examiner

Primary Examiner—Gary L. Kunz
Assistant Examiner—Regina M. Deberry
(74) Attorney, Agent, or Firm—John P. White; Cooper & Dunham LLP

(57) ABSTRACT

The present invention provides a method for predicting the likely timing of the onset of menopause for a perimenopausal female subject by determining the amount of hLHβcf in a sample from the subject comprising the steps of: (a) contacting a sample from the subject with an antibody which specifically binds to hLHβcf without substantially cross-reacting with hLH, hLHβ or hLHβcf, under conditions permitting formation of a complex between the antibody and hLHβcf; (b) measuring the amount of complex formed, so as to thereby determine the amount of hLHβcf in the sample; and (c) comprising the amount of hLHβcf in the subject's sample determined in step (b) with either (i) the amount determined for known postmenopausal female subject or (ii) the amount determined for a sample from a known premenopausal female subject, wherein an amount of hLHβcf in the sample similar to the amount of hLHβcf in the known postmenopausal sample indicates temporal proximity to the onset of menopause, and an amount of hLHβcf in the sample similar to the amount of hLHβcf in the known premenopausal sample indicates temporal distance from the onset of menopause for the subject. AS described herein amount is both concentration and pattern of measurement of concentrations in one or more consecutive urine specimens.

11 Claims, 39 Drawing Sheets

FIGURE 1

```
 1                                                                        20
Ser-Arg-Glu-Pro-Leu-Leu-Arg-Pro-Trp-Cys-His-Pro-Ile-Asn-Ala-Ile-Leu-Ala-Val-Glu-Lys-Glu-Gly
23
-Cys-Pro-Val-Cys-Ile-Thr-Val-Asn-Thr-Thr-Ile-Cys-Ala-Gly-Tyr-Cys-Pro-Thr-Met-Met-Arg-Val
45
Leu-Gln-Ala-Val-Leu-Pro-Pro-Leu-Pro-Gln-Val-Val-Cys-Thr-Tyr-Arg-Asp-Val-Arg-Phe-Glu-Ser-
67
Ile-Arg-Leu-Pro-Gly-Cys-Pro-Arg-Gly-Val-Asp-Pro-Val-Val-Ser-Phe-Pro-Val-Ala-Leu-Ser-Cys-
89
Arg-Cys-Gly-Pro-Cys-Arg-Arg-Ser-Thr-Ser-Asp-Cys-Gly-Gly-Pro-Lys-Asp-His-Pro-Leu-Thr
111
Cys-Asp-His-Pro-Gln-Leu-Ser-Gly-Leu-Leu-Phe
```

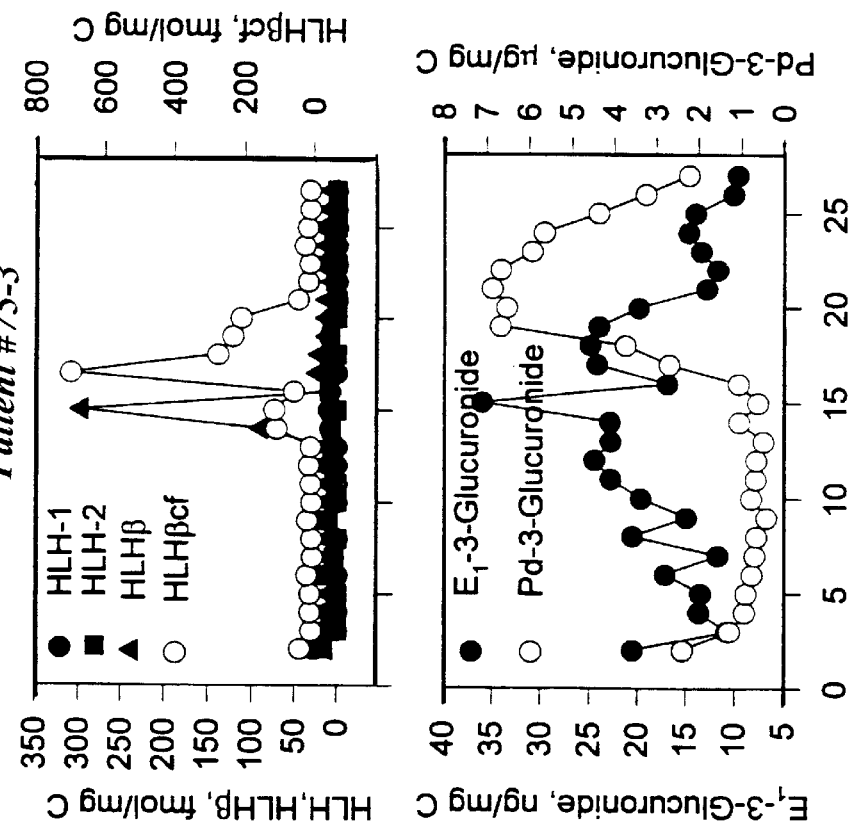
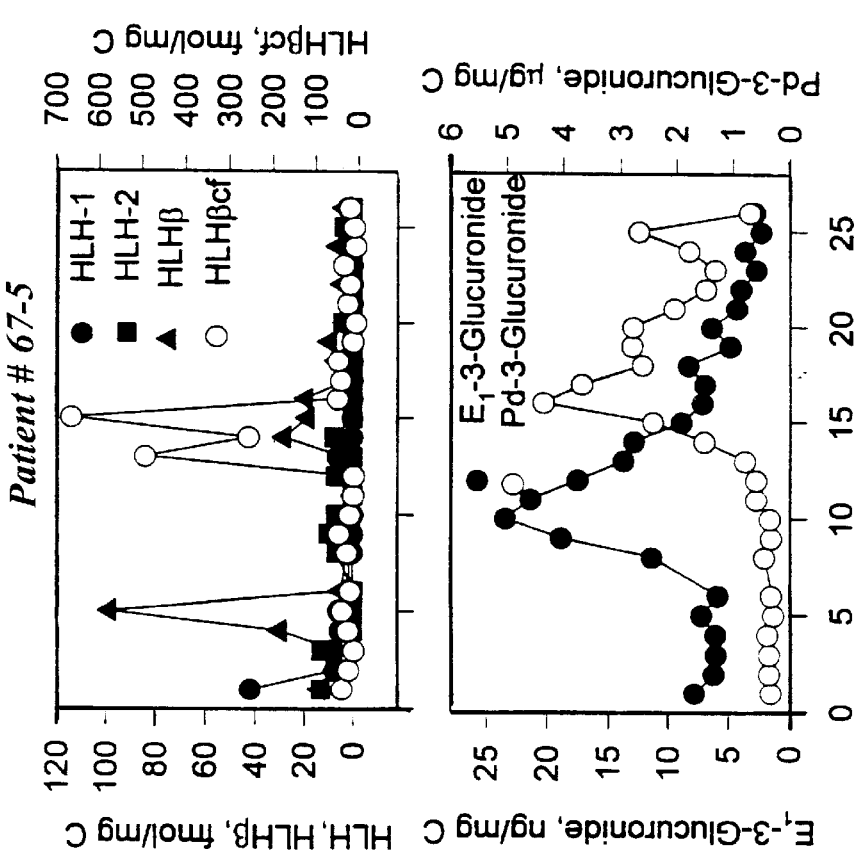

Day of Urine Collection (Random)

Day of Urine Collection (Random FMV)

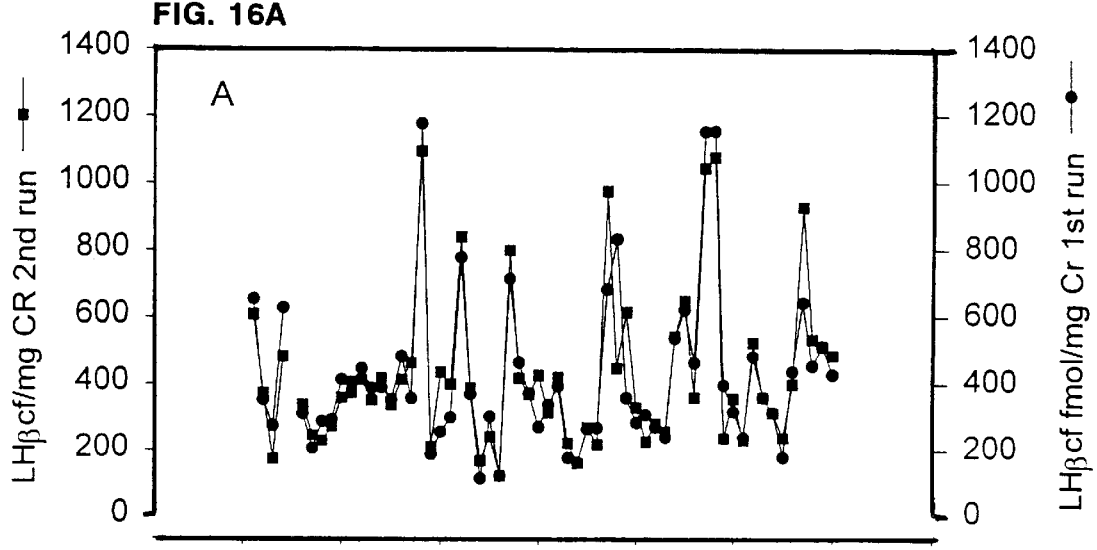
FIG. 16A
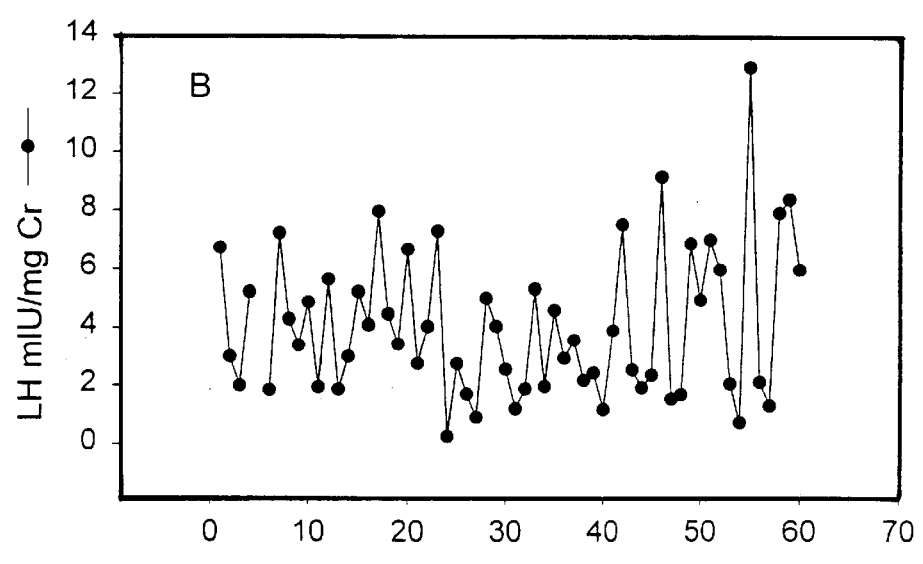
FIG. 16B  Day of Urine Collection

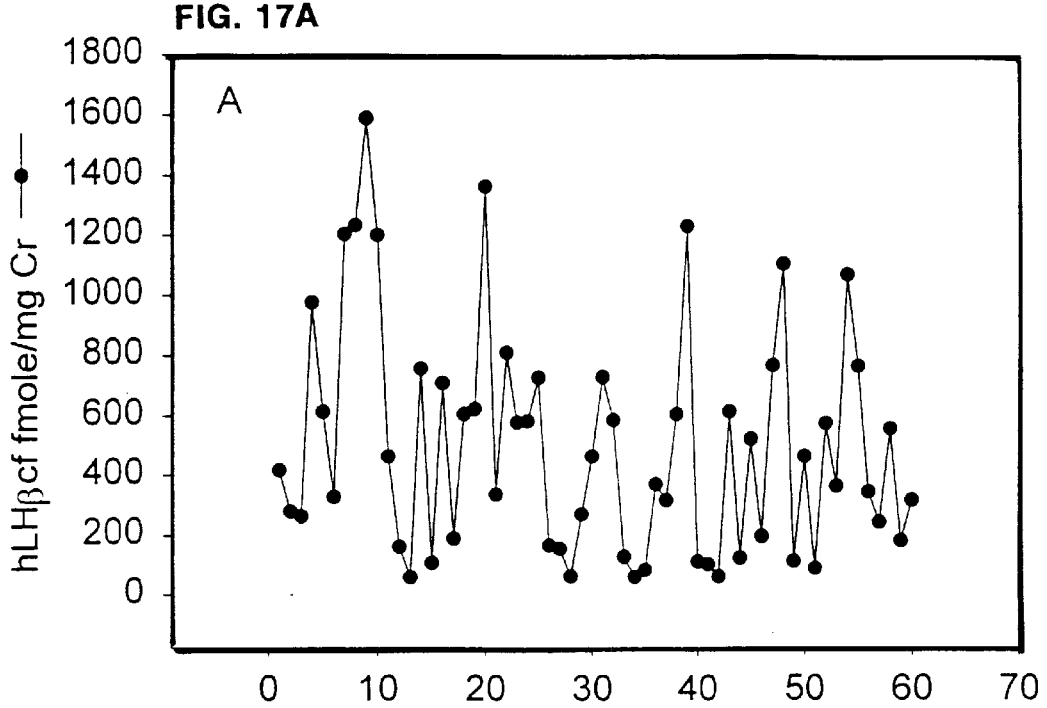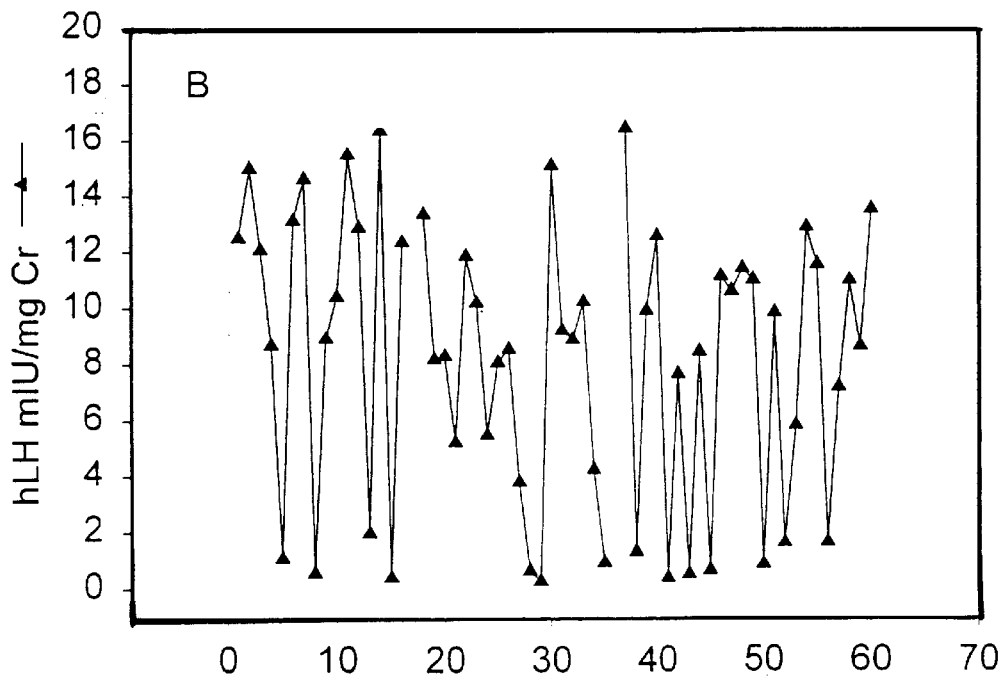
FIG. 17A
FIG. 17B Day of Urine Collection

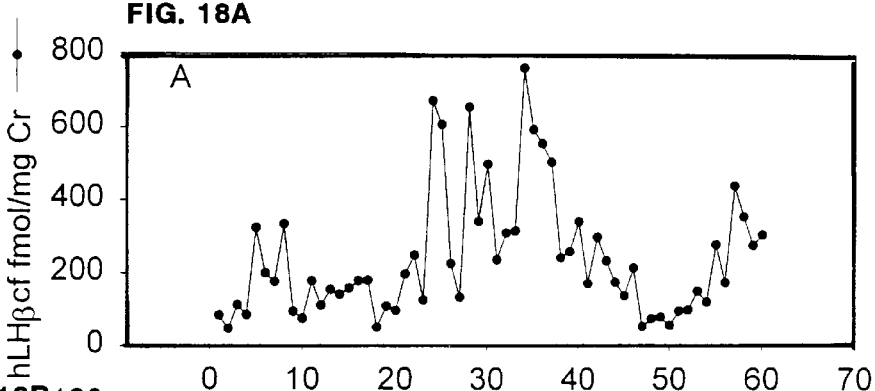
FIG. 18A
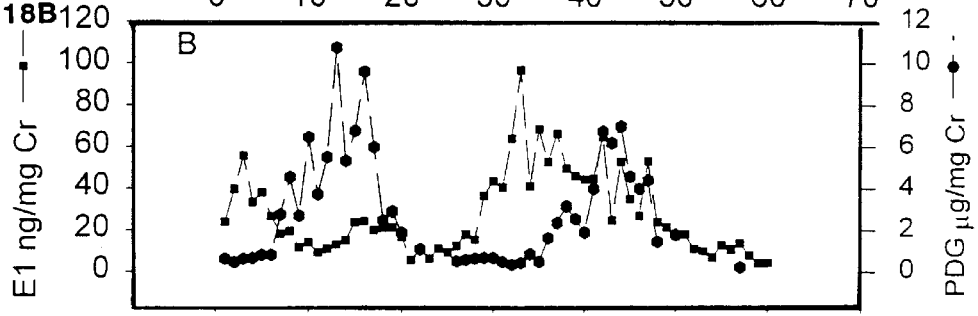
FIG. 18B
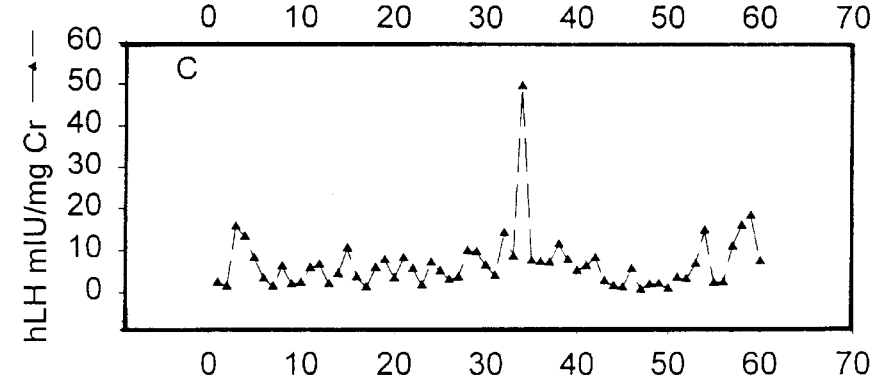
FIG. 18C   Day of Urine Collection

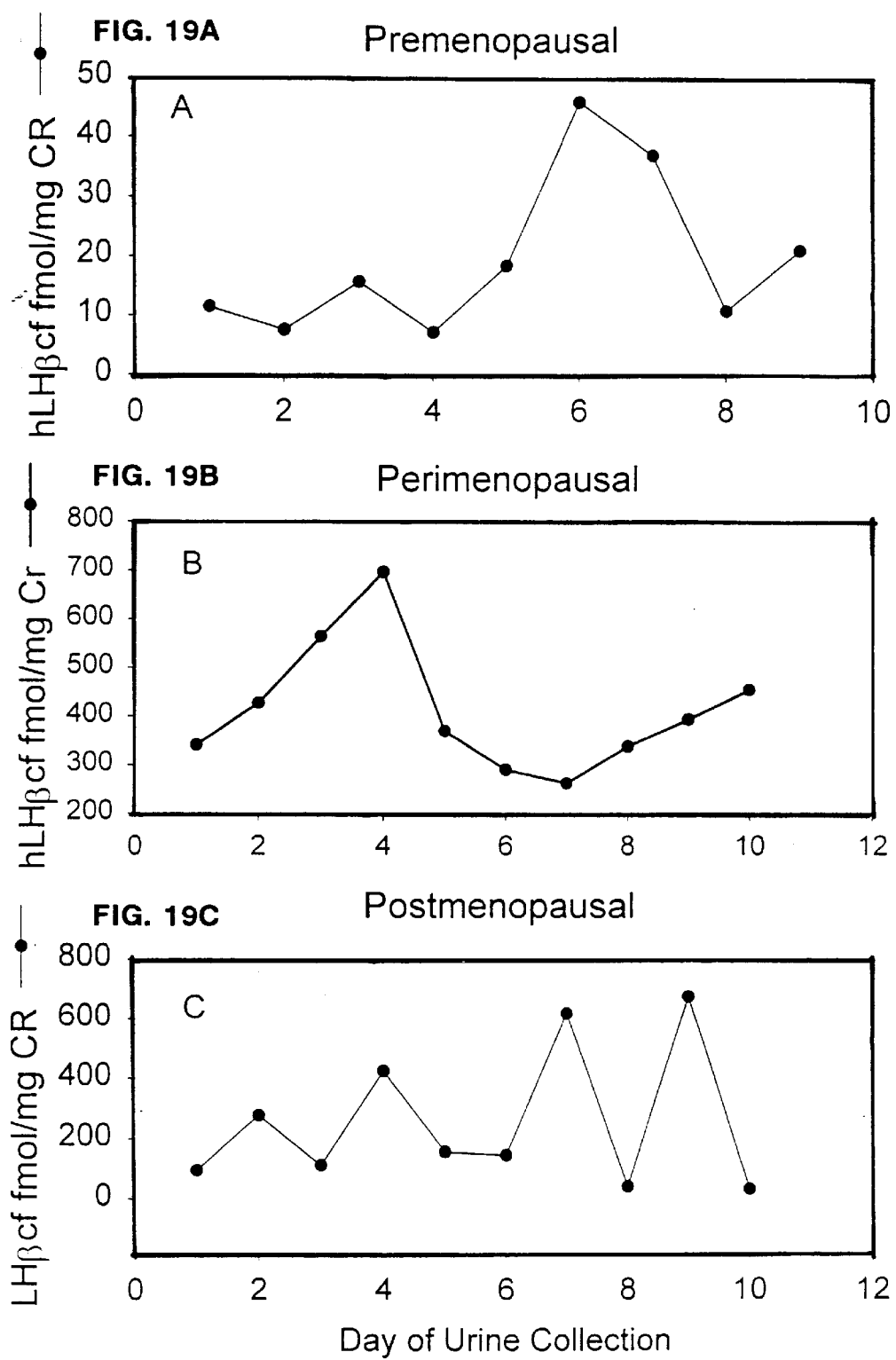
FIG. 19A Premenopausal
FIG. 19B Perimenopausal
FIG. 19C Postmenopausal
Day of Urine Collection DETERMINATION OF THE AMOUNT OF hLHβ CORE FRAGMENT IN A SAMPLE FROM A SUBJECT AND USES THEREOF This application is a continuation of PCT International Application No. PCT/US99/02279, filed Feb. 3, 1999, designating the United States of America, which is a CIP of and claiming the priority of U.S. Ser. No. 09/018,122, now abandoned filed Feb. 3, 1998, the contents of which are hereby incorporated by reference into the present application.

The invention disclosed herein was made with Government support under NIH Grant Nos. HD15454, ES07589 and M01-RR00645, AG13783, ES07589, AG 12745, AG12222 HD15454. Accordingly, the U.S. Government has certain rights in this invention.

Throughout this application, various publications are referenced by author and date. Full citations for these publications may be found listed alphabetically at the end of the specification immediately preceding the the claims. The disclosures of these publications in their entireties are hereby incorporated by reference into this application in order to more fully describe the state of the art as known to those skilled therein as of the date of the invention described and claimed herein.

BACKGROUND OF THE INVENTION

With the extension of the human life span, women spend one-third of their lives beyond the reproductive years. The transition into menopause, a normal process of aging, is associated with physical risks and psychological adjustments. It is critical to improve understanding of the these changes. However, there is a lack of diagnostic tools for monitoring the temporal stages in the history of menopause despite the importance of this transition period. There is no reliable test to determine how close a woman is to menopause. Clinical decisions for treatment of perimenopausal women today are based chiefly upon subjective symptoms rather than objective diagnostic tests.

There is a lack of adequate chemical markers for defining the menopausal state since neither serum gonadotropins, estradiol, nor inhibin A or B levels are adequate for diagnosis unless daily sampling is performed for prolonged periods of time (Burger, 1996;. Burger, et al., 1995; Burger, 1994a; Burger, 1994b; Hee, et al. 1993; Metcalf, 1988 ). A number of studies of women during the periovulatory period have indicated that the currently used biochemical markers of menopause are inadequate (Burger, 1996;. Burger, et al., 1995; Burger, 1994a; Burger, 1994b; Hee, et al. 1993; Metcalf, 1988; Santoro, et al. 1996). Gonadotropin levels fluctuate from postmenopausal cncentrations back down to levels found in normal, young cycling women (Burger, 1996; Burger, et al., 995; Burger, 1994a; Metcalf, 1988; Metcalf, et al. 1982; Metcalf and Donald, 1979). What appear to be normal ovulatory cycles may follow prolonged anovulatory periods coincident with postmenopausal concentrations of follicle stimulating hormone (FSH) and luteinizing hormone (LH) (Burger, 1996;. Burger, et al., 1995; Burger, 1994a; Burger, 1994b; Metcalf, 1988; Metcalf, and Donald, 1979; Metcalf, et al. 1981a). Some investigators declare that all current biochemical measurements have little predictive value during the menopausal transition because of the great variations in levels of steroids and gonadotropins. (Burger, 1996;. Burger, 1994a; Burger, 1994b; Hee, et al. 1993;. Metcalf, and Donald, 1979; Metcalf, et al. 1981b; Metcalf, 1979).

Although elevations in certain serum gonadotropin levels reflecting gametogenic failure usually occur several years before a decline in estrogen and irregular cycling begins, measurement of serum gonadotropin levels, estrogen, and inhibins A and B have limited value to the practicing physician. A reliable test is essential to differentiate a premenopausal woman from a woman very early in perimenopause or the laster from one in the middle of the transition; menopausal changes could be placed in relation to the stage of menopausal transition. This would help to resolve, or example, whether treatment for osteoporosis should begin much earlier or that hormone replacement therapy should begin at a different time rather than based on symptomatic discomfit. The present invention solves these problems by providing urinary-based immunoassay methods and assay kits Human gonadotropins undergo metabolic transformations, which result in the presence of several smaller, structurally and immunologically related forms in the urine. A major form of urinary hCG-associated immunoreactivity is an epitope on a molecule smaller than heterodimeric hCG (Birken et al., 1996; O'Connor et al., 1994; Schroeder and Halter, 1983). This molecule has been identified as an hCG beta core fragment (hCGβcf) (Birken et al., 1988; Blithe et al., 1988). In normal pregnancy, the core fragment constitutes a major mole fraction of urinary hCG excretion (Kato and Braunstein, 1988). Using polyclonal antisera raised against hCGβcf, immunoreactive beta core like activity can be detected in both postmenopausal women and in the periovulatory period of the normal menstrual cycle (Iles et al., 1992; Neven et al., 1993). However, some immunoreactivity results from cross-reactivity with the polyclonal hCGβcf antibodies. An hLH beta core fragment (hLHβcf) has been isolated from human pituitaries and a panel of monclonal antibodies has been generated (Birken et al., 1993a; Kovalevskaya et al., 1995).

The corresponding urinary fragment is inferred from mass spectral and immunochemical analysis of chromatographically separated urinary forms. Physico-chemical characteristics, primarily mass spectral and chromatographic, indicate that the pituitary and urinary forms of hLHβcf have a different structure, probably in the carbohydrate moieties. The carbohydrate moiety of the pituitary hLHβcf resembles that of pituitary hLHβ rather than displaying the degraded carbohydrate chains present in urinary hCGβcf. The endogenous urinary core material is extremely stable to repeated freeze/thaw cycles and prolonged storage at 4° C. or at room temperature. HLHβcf cross-reaction with some hLH cr hLHβ monoclonal antibodies may well interfere with the accurate estimation of the day of hLH surge when urinary tests are utilized. The expression of hLHβcf in the urine of both reproductive and postreproductive age women and in men, is now characterized employing assays highly specific for the pituitary form of the fragment.

Analysis or the metabolites of the gonadotropins excreted into urine can help to distinguish between healthy and abnormal physiological states. For example, the hCG β core fragment (hCGβcf) is present at high levels in the urine of normal pregnant women (Kato et al., 1988) but, also, occurs abnormally in the urine of nonpregnant patients with a variety of malignancies (O'Connor et al., 1988, Cole et al., 1988a,1988b,1990). Until now, it has not been possible to distinctly measure one of the fragments in the presence of the others. For example, the utility of the hCGβcf molecule as a marker of malignancies in postmenopausal women has been compromised by the cross-reactions of antibodies elicited to the hCGβcf with a molecule of similar structure and size (presumably the homologous fragment of hLH)

excreted by normal postmenopausal women in their urine. Consequently, the high threshold measurement compromised the ability of hCGβcf to serve as a cancer marker in this important patient population. Distinguishing hLHβcf from an hCGβcf, therefore, is of great value. A preponderance of hLHβcf may indicate a normal state while a major mole fraction of the hCG fragment may be associated with malignancy (Birken et al., 1993b). The present invention provides a method to make such a distinction. Immunological analysis of the hLHβcf in normal cycling women, as compared with infertile patients, may identify a metabolic marker associated with an abnormal state (i.e. an ovulatory cycles, polycystic ovarian disease). Antibodies to the hLHβcf, isolated from pituitary extract, can also be used to measure such a molecule in urine.

Methods for specific immunometric assays which report the levels of expression of this new hLH molecular form, hHLβcf, in men and women at different stages of their reproductive history are described herein. The present invention now makes it possible to evaluate the metabolism of hLH in premenopausal, perimenopausal and postmenopausal women and in men and to distinguish between normal and abnormal physiological states.

In addition, these methods to visualize LH fragment in plasma differentiates LH fragment derived directly from pituitary from that derived by peripheral cleavage of LH. hLHβcf may circulate in plasma.

The methods described herein measure the stable metabolic products of LH which are excreted into urine usually at much higher concentrations than the parent hormones, themselves, are found in urine or blood. These assays do not use heterodimeric hormones which are unstable, unless supplemented by stabilizers such as glycerol, because they dissociate into their constituent, non-covalently bound subunits, especially under acid conditions or upon freeze thaw cycles. Urinary metabolic forms represent endproducts of a degradative process. The forms explored have proven to be stable unlike the parent hormones which can dissociate into free subunits greatly complicating urinary measurements. Antibodies specific for hLH beta core fragment some of which are referred to in the present application, have been detailed in the related co-pending U.S. application Ser. No. 08/763,669 now U.S. Pat. No. 5,976,876 filed Dec. 11, 1996, the content of which is hereby incorporated by reference. In particular, related co-pending U.S. application Ser. No. 08/763,669 now U.S. Pat. No. 5,976,876 filed Dec. 11, 1996, describes monoclonal antibodies designated B505, B503 and B504 which are produced by the hybridoma cell lines accorded ATCC Accession Nos. 12000, 11999 and 12002 respectively and details methods for their production and use, which is hereby incorporated by reference.

This invention also provides monoclonal antibodies B503, B504 and B505 and the hybridoma cell lines for producing said antibodies. The hybridhybridoma cell lines were deposited pursuant to and in satisfaction of the requirements of the Budapest Treaty on the International Recognition of the Deposit of Microorganisms for the Purposes of Patent Procedure with the American Type Culture Collection (ATCC), 10801 University Boulevard, Manassas, Va. 20110-2209 on Dec. 11, 1995 under ATCC Designation Nos. 11999, 12002 and 12000, respectively. All restrictions upon public access to these deposits shall be removed upon the grant of a patent on this application and the deposit shall be replaced if viable samples cannot be made by the depository named hereinabove.

The present invention takes advantage of the natural metabolic processing of LH as a means of improving the diagnosis of women in perimenopause as well as to assess patterns of metabolites useful for monitoring estrogen replacement therapy.

The core fragment of hLHβ is useful as a urinary marker for many different physiological states including disease, as markers of the state of senescence the ovary.

As used in this application hLH beta core fragment (hLHβcf) means and includes a fragment of human luteinizing hormone (hLH) which is produced as a metabolize and which has been isolated from human pituitaries (Birken et al. 1993; Kovalevskaya et al., 1995) as well as related molecules and other metabolites of hLH which may be used as markers of menopause.

SUMMARY OF THE INVENTION

This invention provides a method for predicting the likely timing of the onset of menopause for a perimenopausal female subject by determining the amount of hLHβcf in a sample from the subject comprising the steps of: (a) contacting a sample from the subject with an antibody which specifically binds to hLHβcf without substantially cross-reacting with hLH, hLHβ or hCGβcf, under conditions permitting formation of a complex between the antibody and hLHβcf; (b) measuring the amount of complex formed, so as to thereby determine the amount of hLHβcf in the sample; and (c) comparing the amount of hLHβcf in the subject's sample determined in step (b) with either (i) the amount determined for known postmenopausal female subject or (ii) the amount determined for a sample from a known premenopausal female subject, wherein an amount of hLHβcf in the sample similar to the amount of hLHβcf in the known postmenopausal sample indicates temporal proximity to the onset of menopause, and an amount of hLHβcf in the sample similar to the amount of hLHβcf in the known premenopausal sample indicates temporal distance from the onset of menopause for the subject. As described herein amount is both concentration and pattern of measurement of concentrations in one or more consecutive urine specimens.

This invention further provides a method for predicting the likely timing of the onset of menopause for a perimenopausal female subject comprising the steps of: (a) contacting a urine sample from the subject with a capturing antibody which specifically binds to hLHβcf without substantially cross-reacting with hLH, hLHβ or hCGβcf under conditions permitting binding of the antibody with any hLHβcf present in the sample wherein the capturing antibody is bound to a matrix (b) separating hLHβcf bound to the matrix bound capturing antibody from hLHβcf not so bound; (c) contacting the hLHβcf bound matrix to the capturing antibody with a second antibody which specifically binds to hLHβcf that is bound to the capturing antibody without cross reacting with hLH, hLHβ or hCGβcf under conditions permitting binding of the second antibody to hLHβcf bound to the capturing antibody; (d) measuring the amount of the second antibody bound to the hLHβcf that is bound to the matrix bound capturing antibody so as to thereby determine the amount of hLHβcf in the sample; and (e) comparing the amount of hLHβcf in the subject's sample determined in step (d) with either (i) the amount determined for a sample from a known postmenopausal female subject or (ii) the amount determined for a sample from a known premenopausal female subject, wherein an amount of hLHβcf in the sample similar to amount of hLHβcf in the known postmenopausal sample indicates temporal proximity to the onset of menopause, and the amount of hLHβcf in the sample similar to the amount of hLHβcf in the known premenopausal sample indicates temporal distance from the onset of menopause for the subject. As described herein amount is both concentration and pattern of measurement of concentrations in one or more consecutive urine specimens.

This invention also provides a method for determining the likely timing of the onset of menopause for a perimenopausal female subject comprising: (a) obtaining a series of samples from the female subject over a period of time; and (b) determining the amount of hLHβcf in each of the samples, the presence of elevated levels of basal hLHβcf in each of the samples indicating that the onset of menopause in the subject is likely to occur in the near future. As described herein amount is both concentration and pattern of measurement of concentrations in one or more consecutive urine specimens.

This invention further provides a method for assessing ovarian function in a subject comprising the steps of: (a) contacting a sample from a subject with an antibody which specifically binds to hLHβcf without substantially cross-reacting with hLH, hLHβ or hCGβcf, under conditions permitting formation of a complex between the antibody and hLHβcf; (b) measuring the amount of complex formed, so as to thereby determine the amount of molecule in the sample; and (c) comparing the amount of hLHβcf in the subject's sample determined in step (b) with either (i) the amount determined for a sample from a subject with normal ovarian function or (ii) the amount determined for a sample from a subject with abnormal ovarian function, wherein an amount of hLHβcf in the sample similar to amount of hLHβcf in the sample from subjects having normal ovarian function indicates normal ovarian function, and amounts of hLHβcf in the sample similar to amounts of hLHβcf having abnormal ovarian function indicates abnormal ovarian function for the subject. As described herein amount is both concentration and pattern of measurement of concentrations in one or more consecutive urine specimens.

This invention also provides a method for determining the efficacy of hormone replacement therapy in a perimenopausal female subject comprising the steps of: (a) contacting a sample from the subject with an antibody which specifically binds to hLHβcf without substantially cross-reacting with hLH, hLHβ or hCGβcf, under conditions permitting formation of a complex between the antibody and hLHβcf; (b) measuring the amount of complex formed, so as to thereby determine the amount of hLHβcf; and (c) comparing the amount of hLHβcf measured in step (b) with either (i) the amount determined for a sample from a subject taken prior to the commencement of therapy or (ii) the amount determined for a sample after a prior course of therapy (iii) the amount determined for a sample from a known premenopausal female subject or (iv) the amount determined for a sample from a known postmenopausal female, wherein differences in the amounts of hLHβcf in the sample indicate efficacy of the hormone replacement therapy for the subject; amounts of hLHβcf in the sample similar to amounts of hLHβcf samples from known premenopausal subjects indicates efficacy of the hormone replacement therapy for the subject; amounts of hLHβcf molecule in the sample similar to amounts of hLHβcf in the sample from known postmenopausal subjects indicates lack of efficacy of the hormone replacement therapy for the subject. As described herein amount is both concentration and pattern of measurement of concentrations in one or more consecutive urine specimens.

Finally, this invention provides a diagnostic kit for predicting the likely timing of the onset of menopause for a perimenopausal female subject by determining the amount of hLHβcf in a sample from the subject comprising: (a) a solid matrix to which an antibody which specifically binds to hLHβcf without substantially cross-reacting with hLH, hLHβ or hCGβcf, under conditions permitting formation of a complex between the antibody and hLHβcf is bound; and (b) a second antibody labeled with a detectable marker; and (c) reagents permitting the formation of a complex between the antibody and hLHβcf. As described herein amount is both concentration and pattern of measurement of concentrations in one or more consecutive urine specimens.

BRIEF DESCRIPTION OF THE FIGURES

FIG. 1.

The hLH β core fragment isolated from human pituitary extracts. Antibodies were developed to this pituitary hLH β core fragment which recognize an homologous fragment of 10K MW in postmenopausal and perimenopausal as well as periovulatory urine. (Seq.ID.No.:1) Cleaved bonds are indicated by the arrows. Peptide portions deleted from the structure are in bold and crossed out. The remaining peptides are represented as Seq.ID.No.:2.: [Arg Pro Trp Cys His Pro Ile Asn Ala Ile Leu Ala Val Glu Lys Glu Gly Cys Pro Val Cys Ile Thr Val Asn Thr Thr Ile Cys Ala Gly Tyr Cys Pro Thr] [Leu Pro Pro Leu Pro Gln Val Val Cys Thr Tyr Arg Asp Val Arg Phe Glu Ser Ile Arg Leu Pro Gly Cys Pro Arg Gly Val Asp Pro Val Val Ser Phe Pro Val Ala Leu Ser Cys Arg Cys Gly Pro Cys]

FIG. 2.

Reverse phase of periovulatory and postmenopausal urine fractions which contain hLHβcf activity and pituitary hLHβcf. All fractions assayed in B505-B503 assay. The open circles denote the elution position of hLHβcf derived from the pituitary. The closed circles and squares denote the elution positions of hLHβcf partially purified from urine.

The difference in elution positions denotes a structural difference (probably carbohydrate differences) between the urinary and pituitary forms. The pituitary form elutes later while the urinary form in postmenopausal and premenopausal women elutes in identical positions. The pituitary form contains carbohydrate and sulfate similar to hLHβ. However, the urinary form may have trimmed carbohydrate.

FIGS. 3A–3K.

Figure 3A:
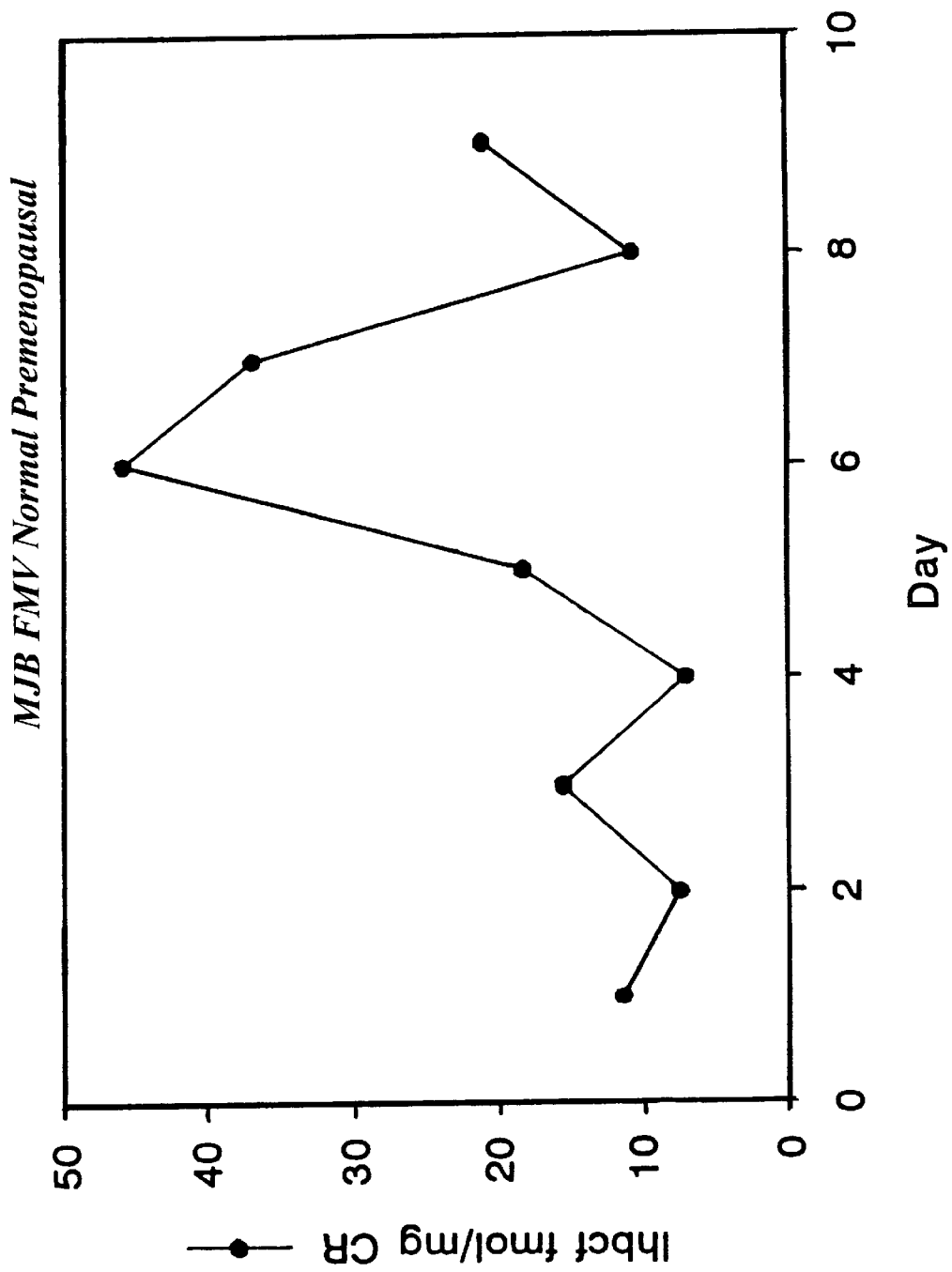
Figure 3B:
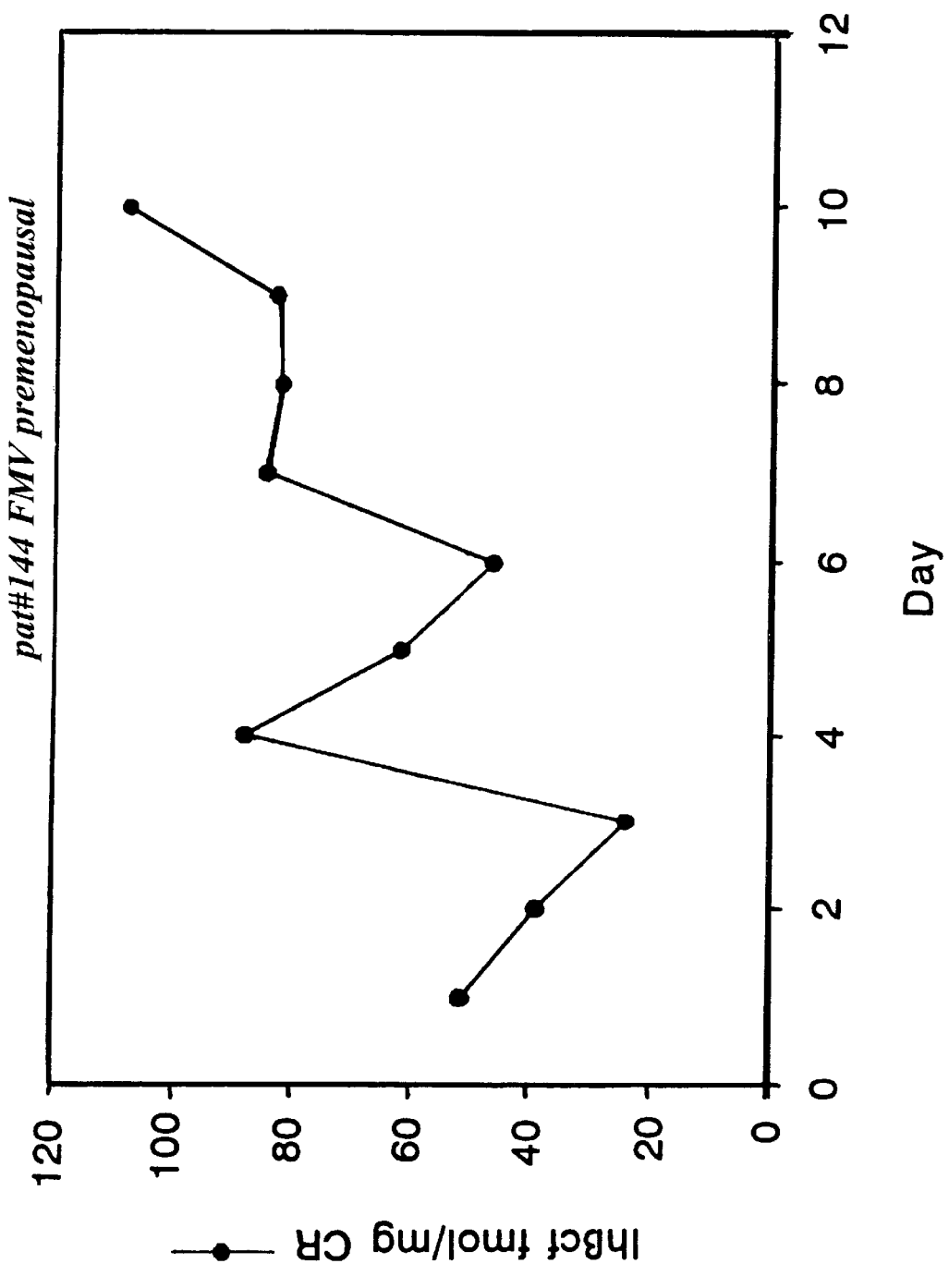
Figure 3C:
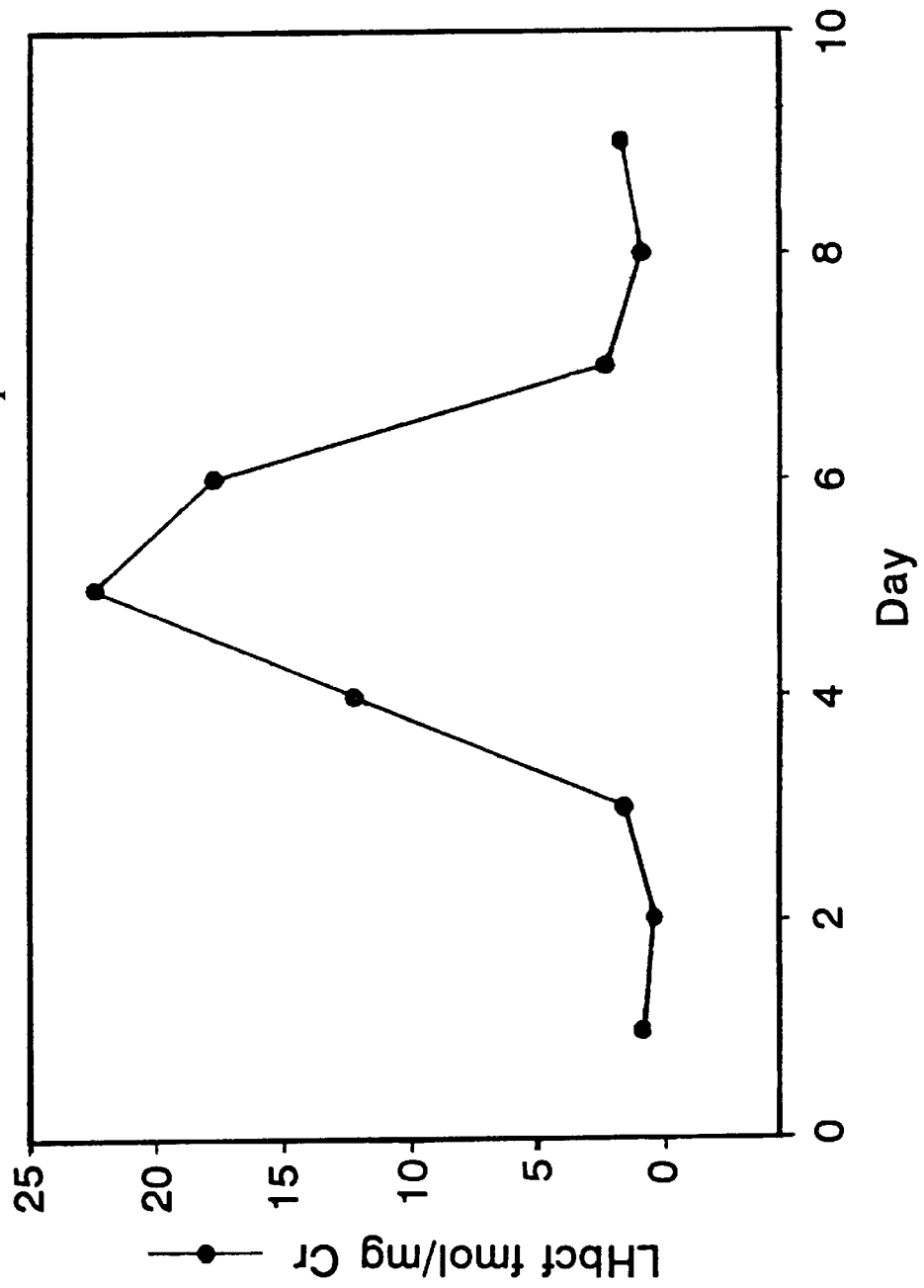
Figure 3D:
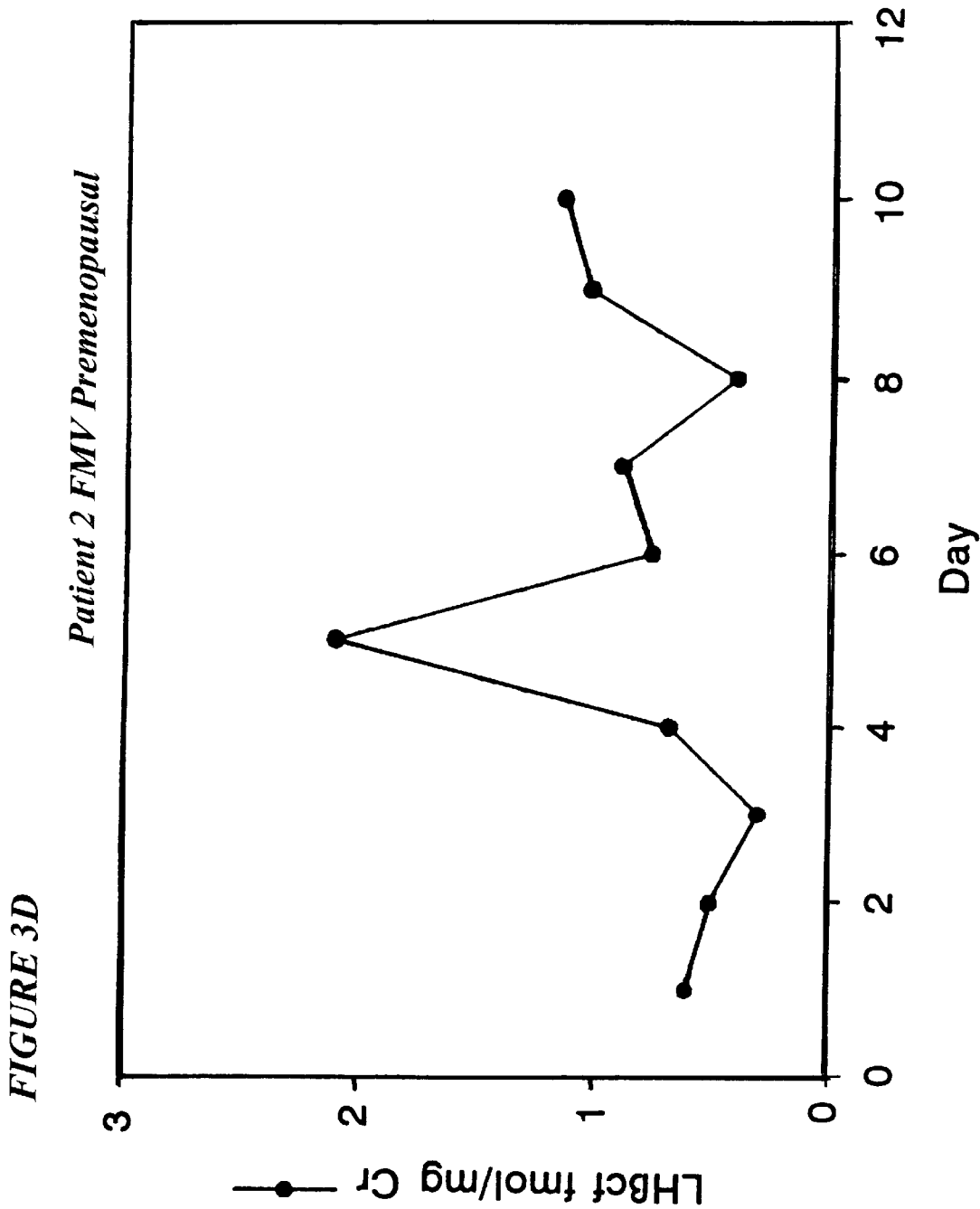
Figure 3E:
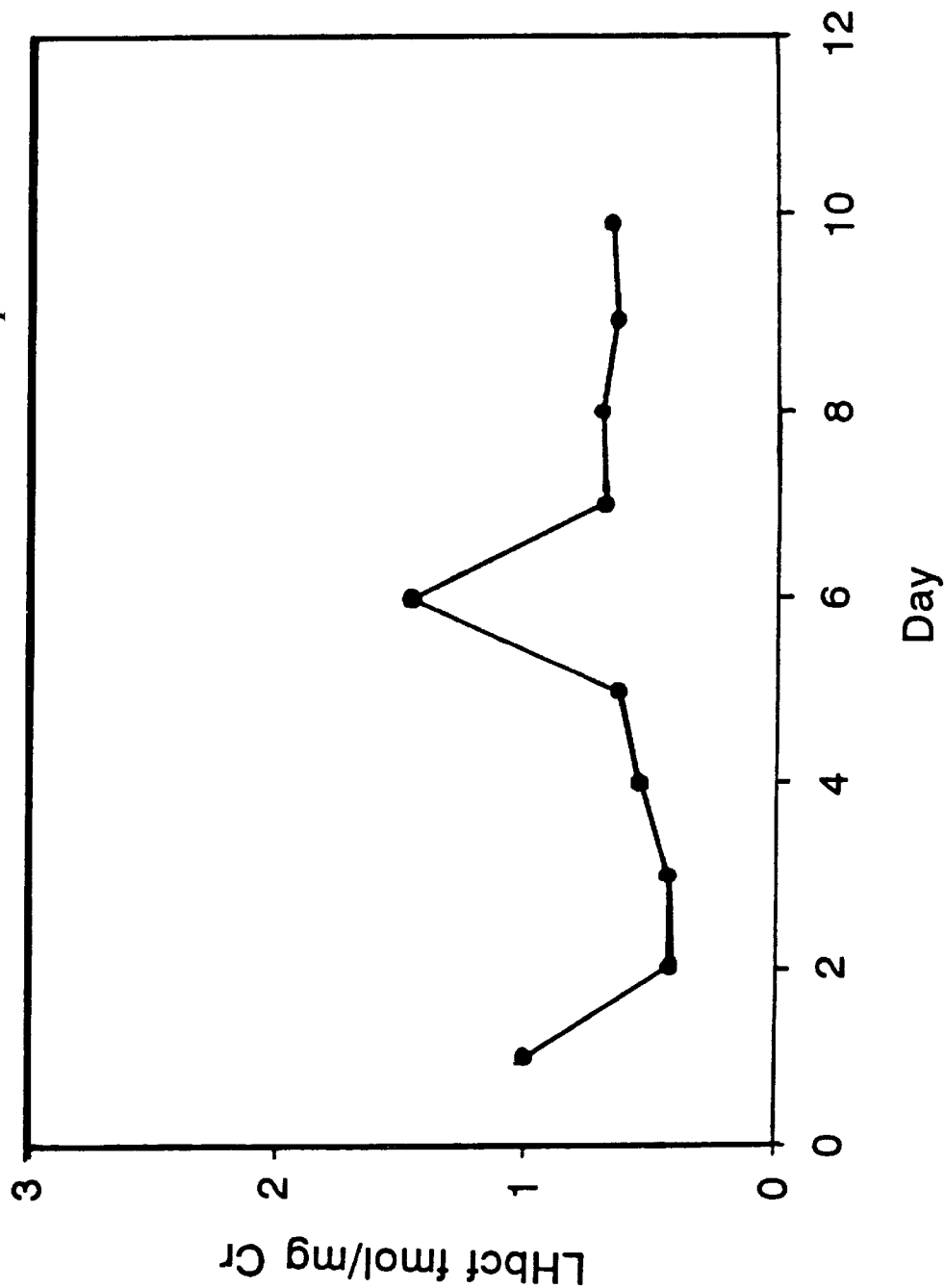
Figure 3F:
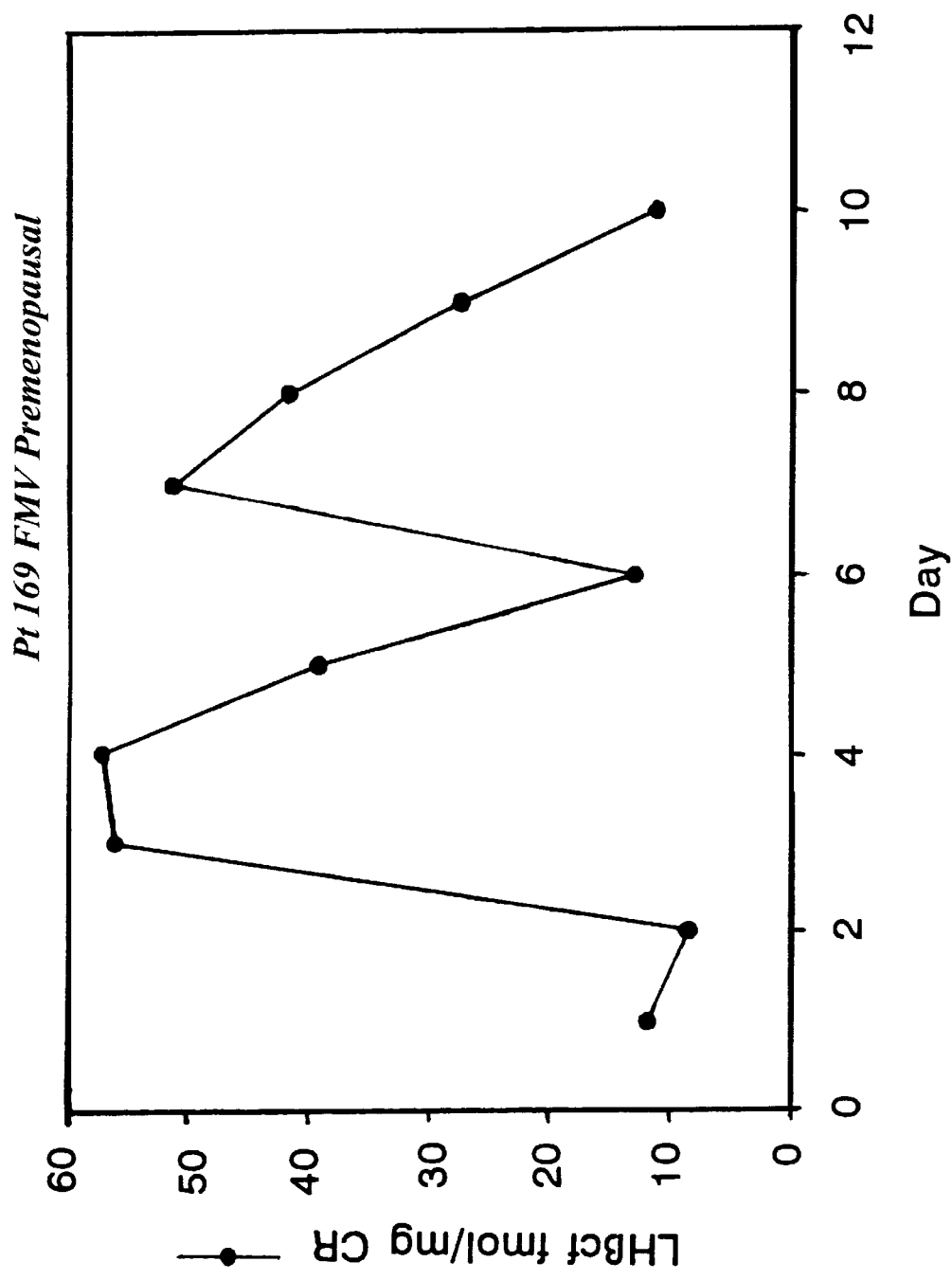
Figure 3G:
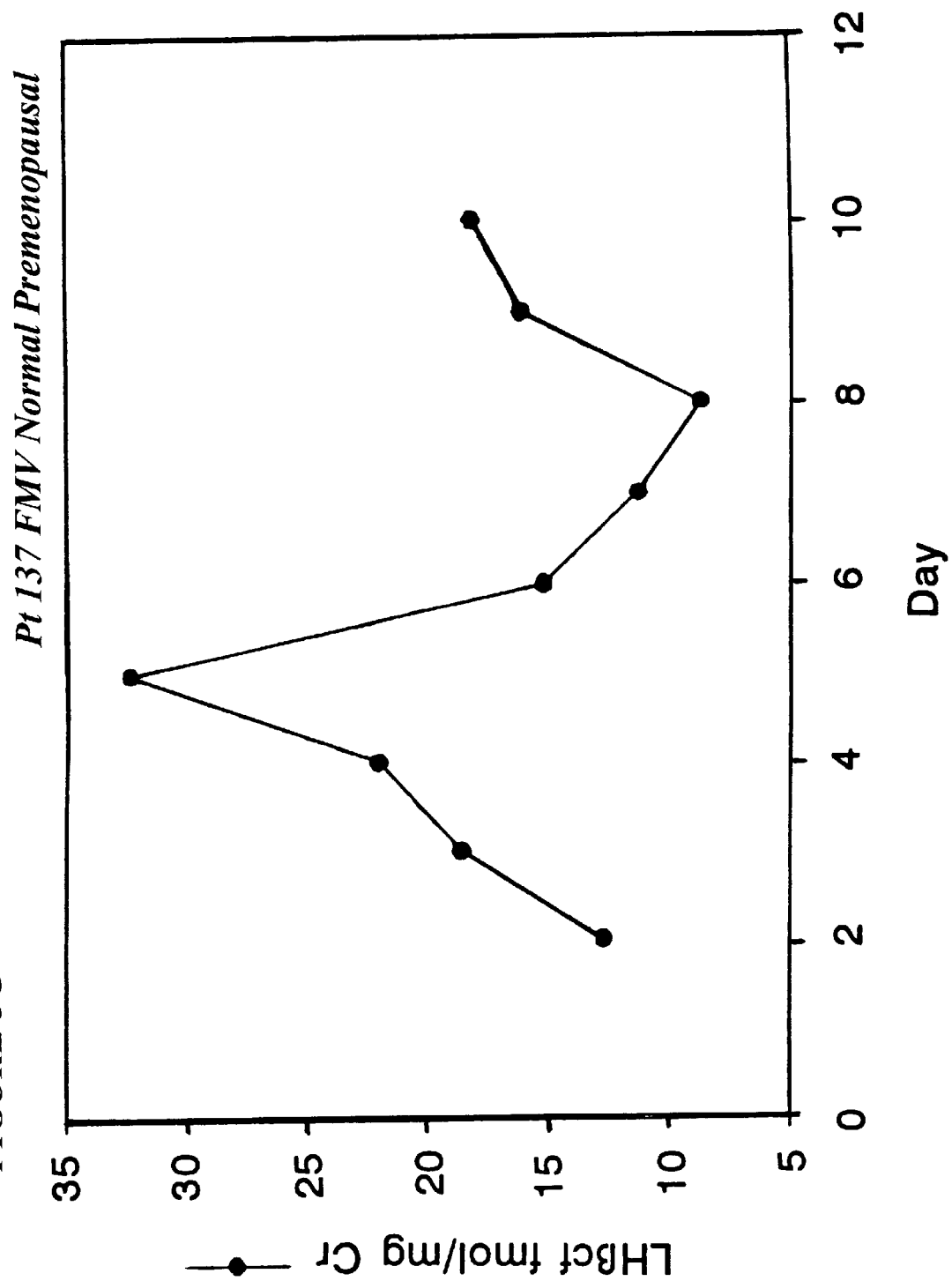
Figure 3H:
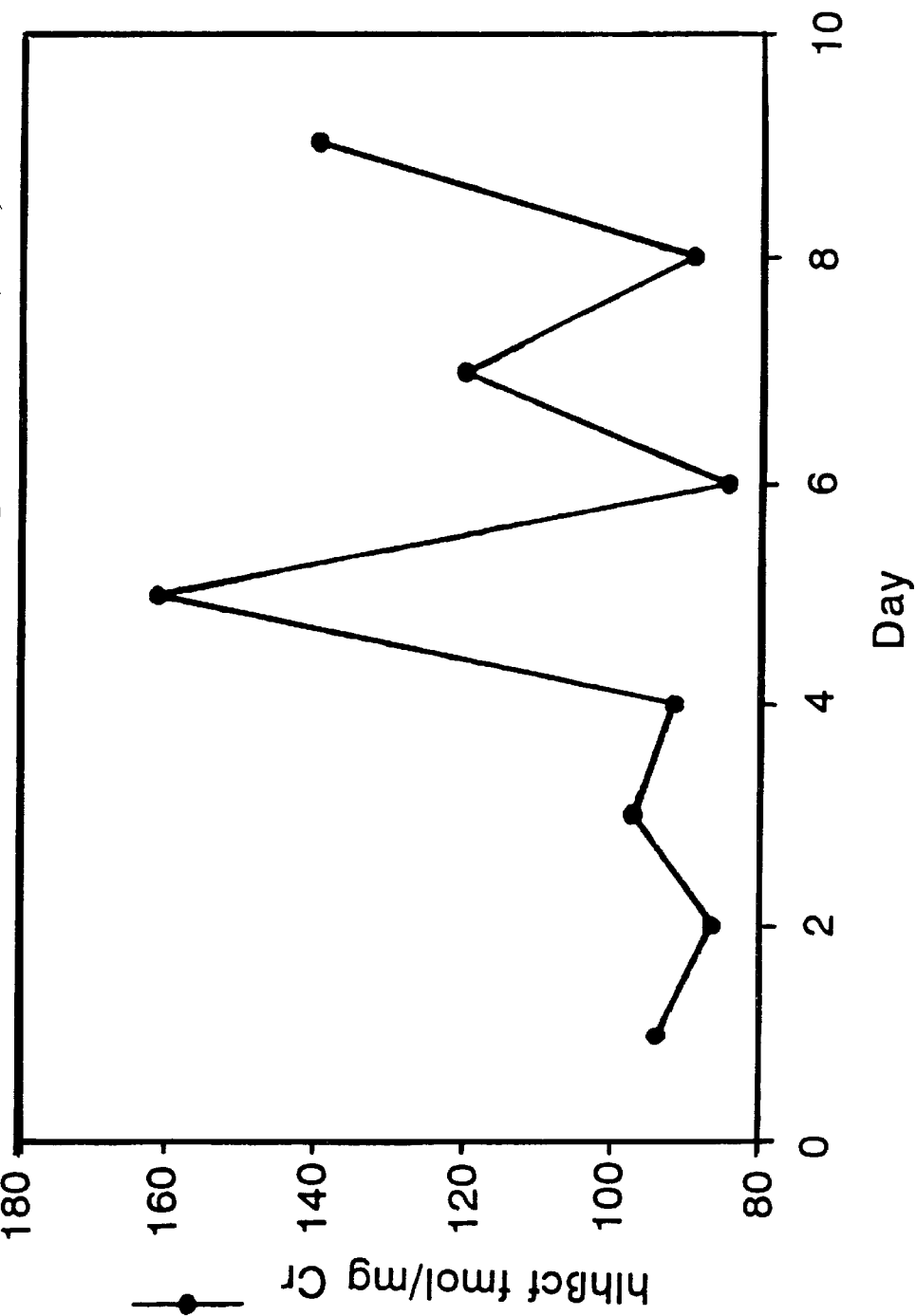
Figure 3I:
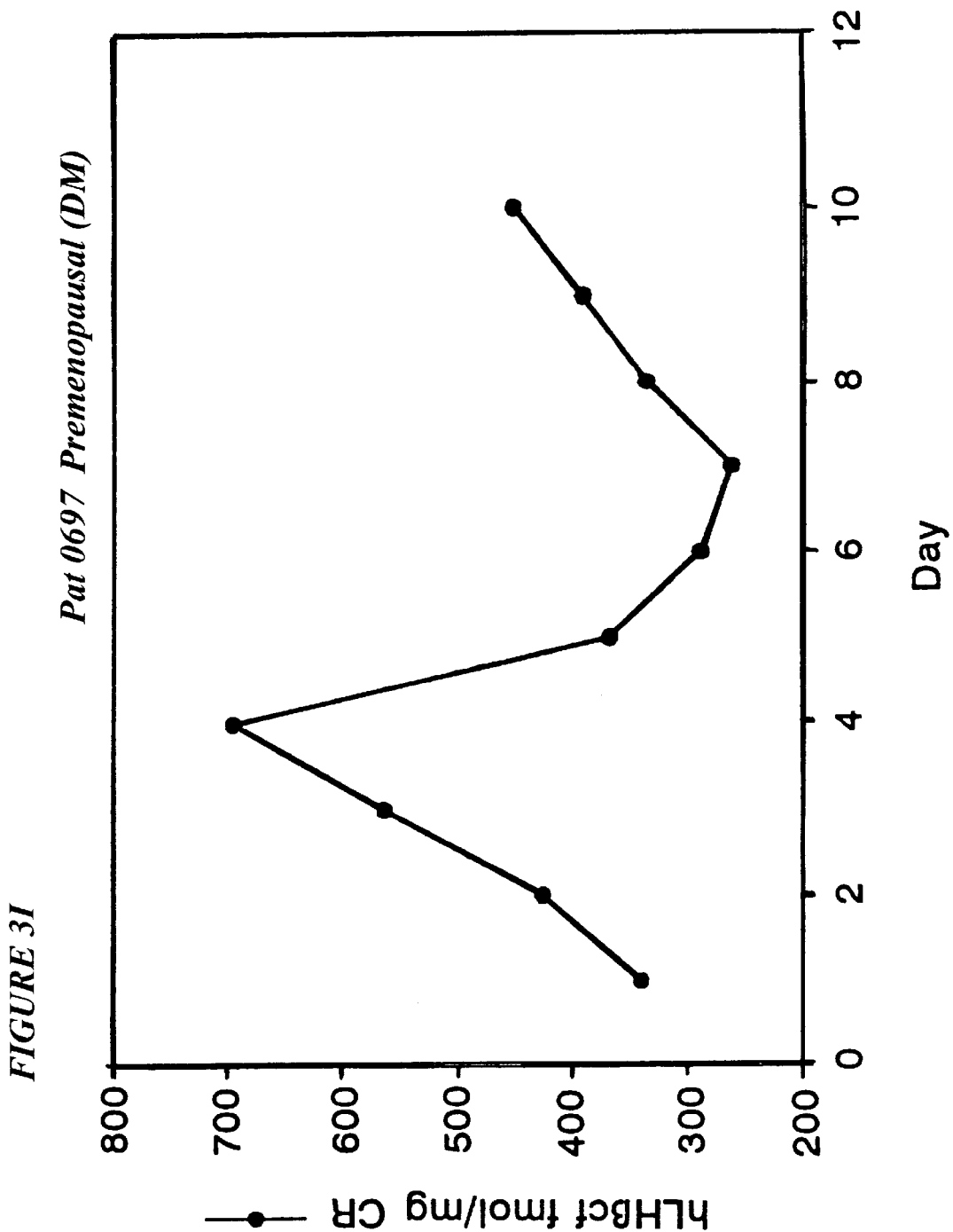
Figure 3J:
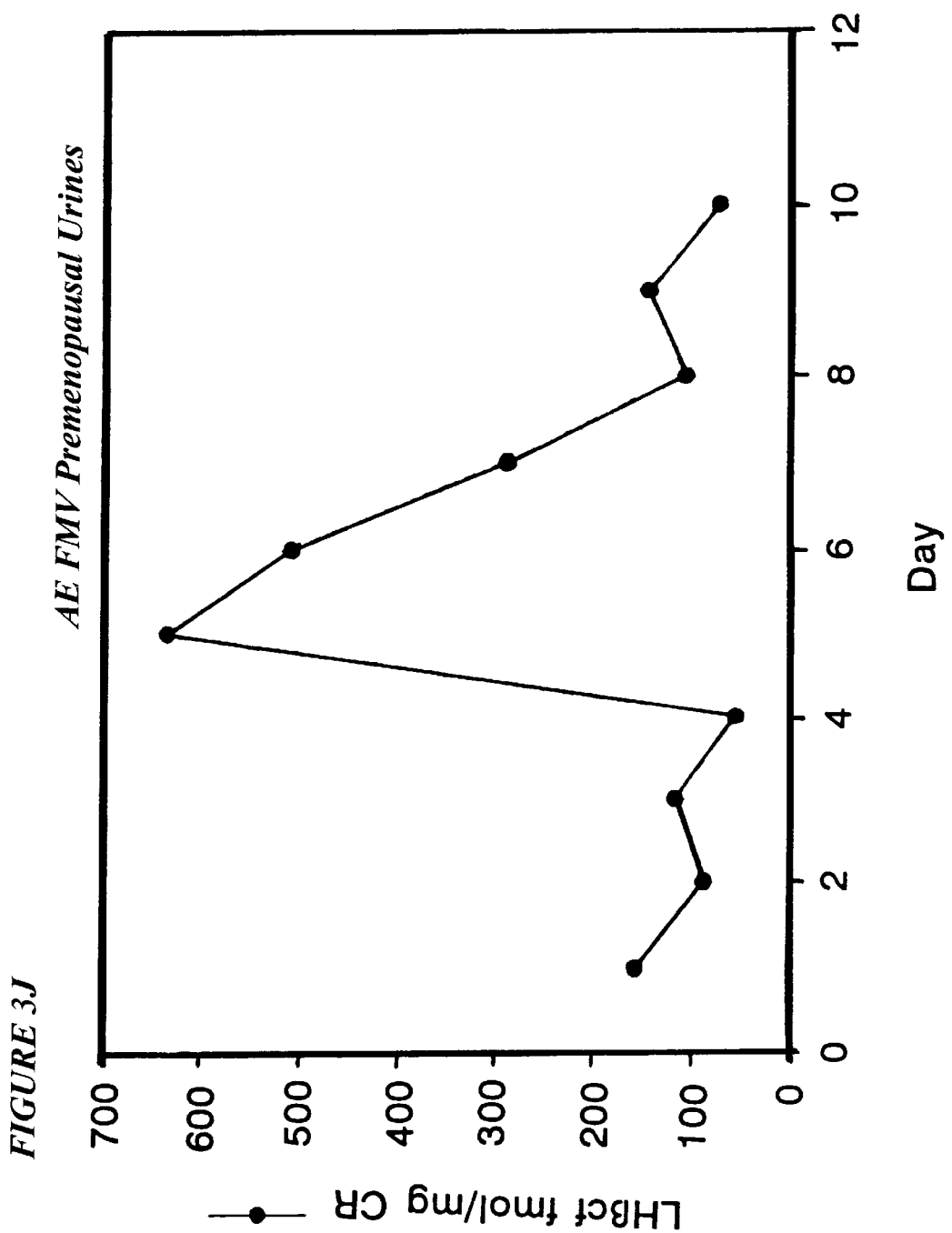
Figure 3K:
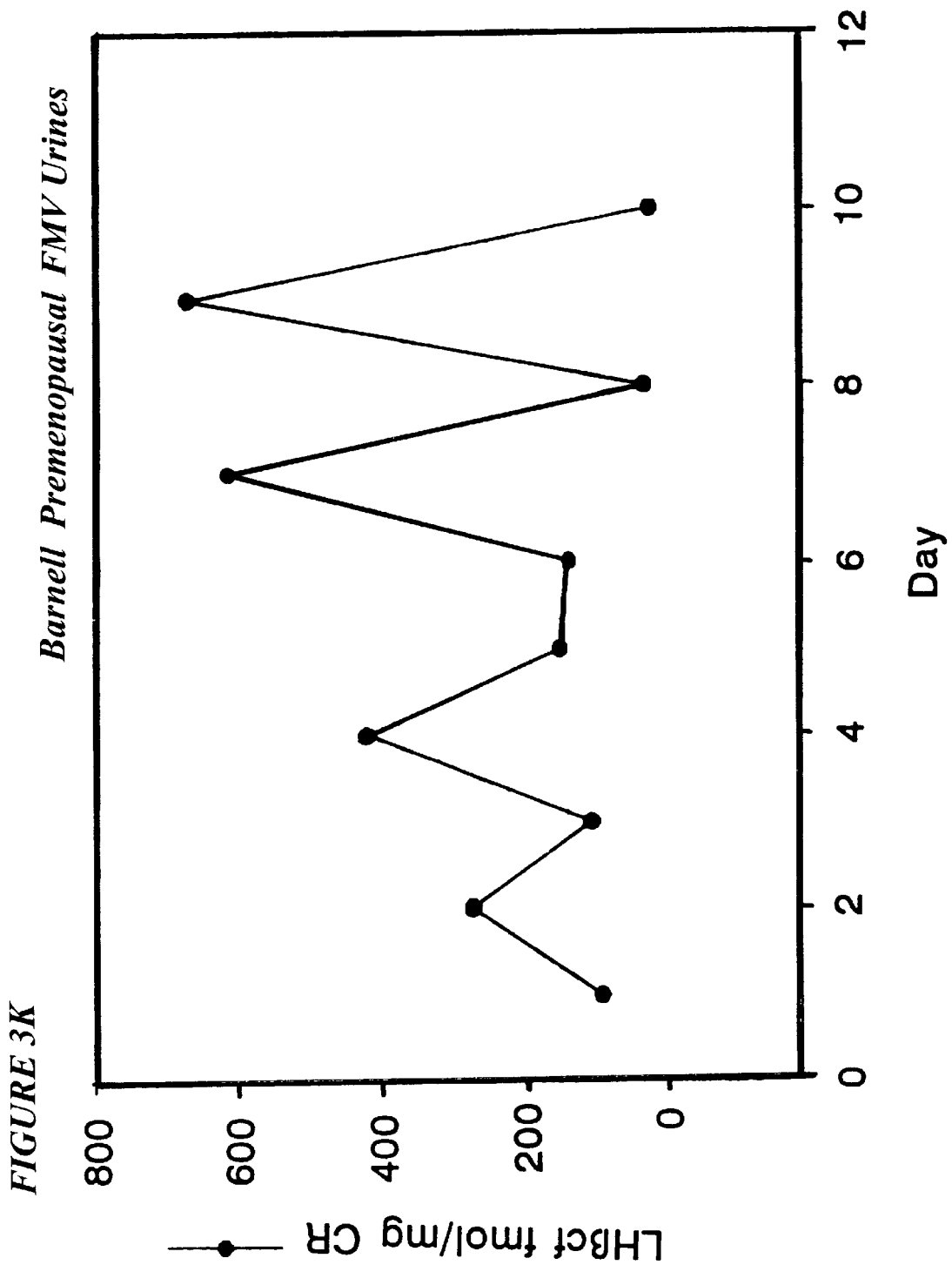

Measurements of the concentration of hLHβcf in the first morning void urine of seven premenopausal (FIGS. 3A–3G), two perimenopausal women (FIGS. 3H–3I) and two postmenopausal women (FIGS. 3J–3K). The premenopausal women were measured from the first day of menses.

FIG. 4.

Typical hLHβcf pattern observed in the first morning void urines of a postmenopausal woman analyzed for 60 days. The assay was repeated weeks later after freeze-thaws. Concentrations and patterns observed were the same as for freshly collected urine specimens. Similar collections from four patients with premature ovarian failure exhibited very similar profiles for this metabolite, except with generally higher concentrations.

FIGS. 5A–5E.

Hormone profiles in the urine of normally cycling women (n=15). Concentrations were presented as mean +/− standard error (SE), fmol/mg creatinine (fmol/mg C). hLH concentration was measured using two different IRMAs (n=8 for hLH-2 assay). Steroid hormone ratio was calculated using estrone-3-glucuronide ($E_1$-3-g) and pregnandiol-3glucuronide (Pd-3-G)×$10^3$ X. Day 0 is the day of hLH surge.

FIG. 6.

Box plot of urinary hLHβcf values in the first ten days of cycle for ten normally cycling women. Day 1 is the first day of menses. The Box extends to the 25th and 75th percentile. The upper and lower bars indicate the 90th and 10th percentile respectively. The upper and lower symbols indicate 95 and 5 percentile points respectively. The solid line inside the box marks the value of the 50th percentile. The dashed line represents the mean of concentration.

FIGS. 7A–7D.

The urinary hLH molecular forms profile in two subjects (patient π75-3, patient #67-5) who did not express measurable intact hLH in either of the hLH assays (FIGS. 7A and 7C respectively). Both hLH free β subunit and hLHβcf surges are clearly apparent. FIGS. 7B and 7D illustrate the corresponding urinary steroid metabolite patterns for the cycles. It can be inferred from the steroid profiles that the subjects experienced normal ovulatory cycles, even in the absence of detectable intact hLH. Concentrations were normalized to creatinine. Day 1 is the first day of menses.

FIG. 8.

Box plot of urinary hormone values for postmenopausal women. The box extends to the 25th and 75th percentile. The upper and lower bars indicate the 90th and 10th percentile respectively. The upper and lower symbols indicate 95 and 5 percentile points respectively. The solid line inside the box marks the value of the 50th percentile. The dashed line represents the mean of concentration (n=107). The wide range of Y values necessitated use of a log scale.

FIGS. 9A–9B.

Figure 9A:
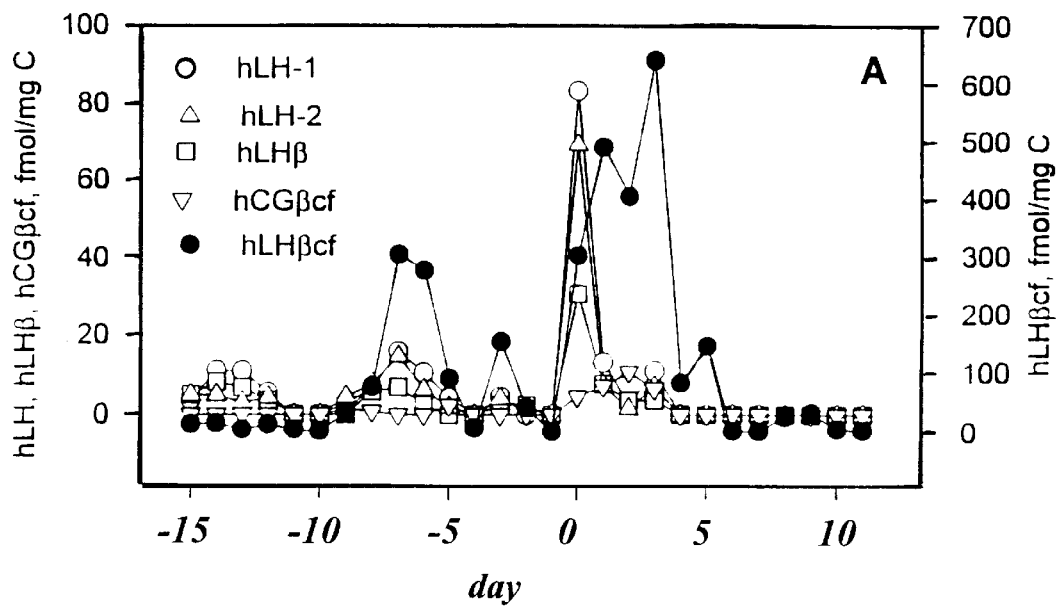
Figure 9B:
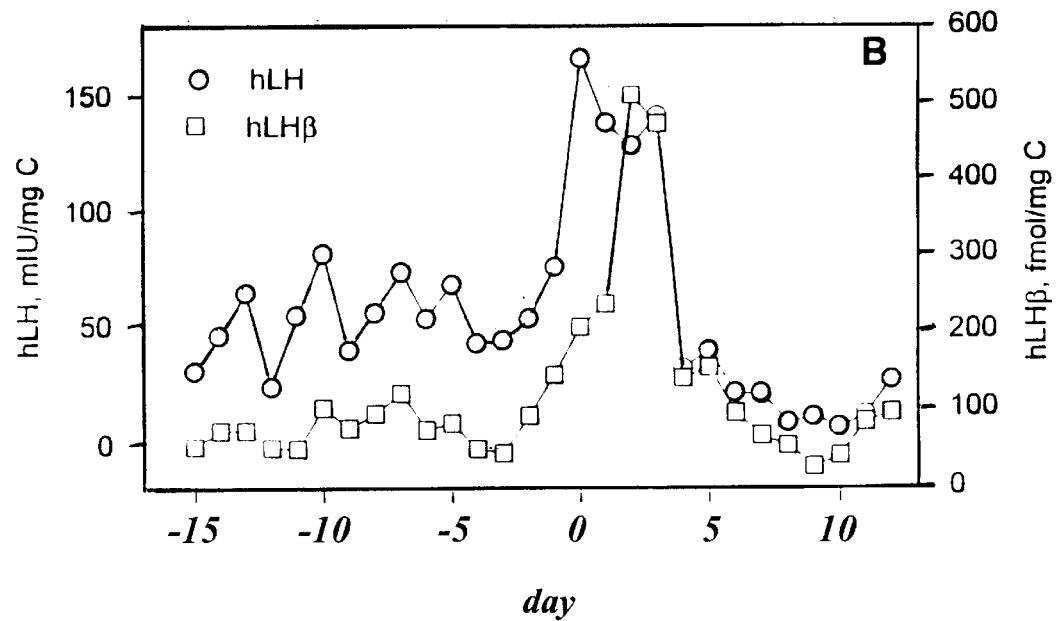

Urinary hormone profile of a patient obtained using monoclonal antibody based IRMAs (FIG. 9A) and RIA using on the base of polyclonal antibodies (provided by NIDDKD) to hLH and hLHβ (FIG. 9B). Concentrations were normalized to creatinine. Day 0 is the day of the hLH surge.

FIG. 10.

Binding of hLH and hLHβ specific antisera (NIDDKD) with hLHβcf in RIA format.

Figure 11B:
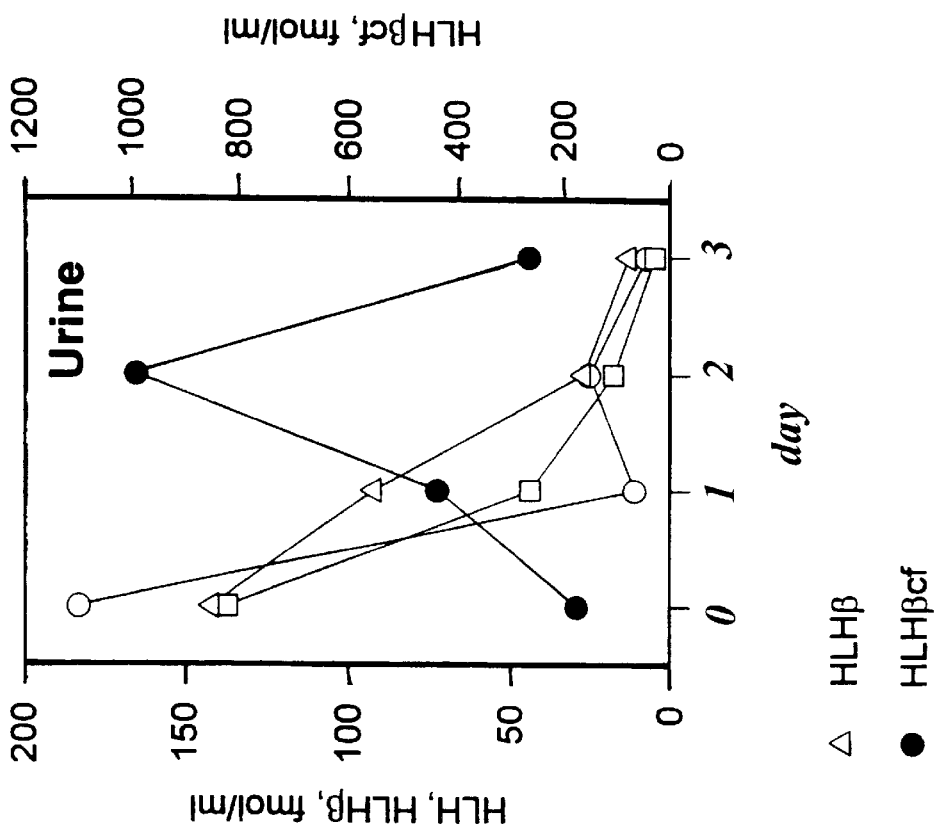
Figure 11A:
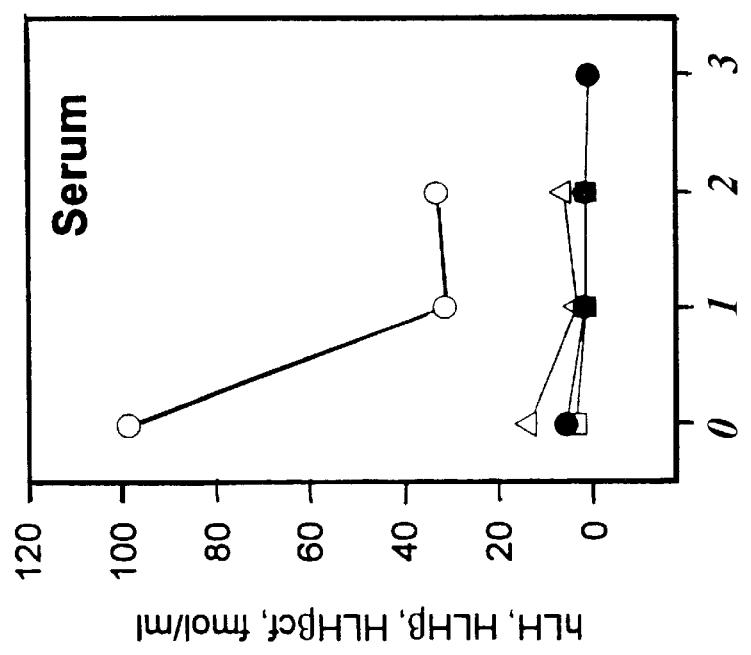

FIGS. 11A–11B.

hLH and hLHβcf in serum and urine of the same patient. The blood levels of intact hLH (open circles) and hLHβcf (closed circles) are illustrated in FIG. 11A. Not that there is an insignificant amount of the hLHβcf was detected in the blood. FIG. 11B illustrates the urinary values for hLH and hLHβcf in the urine for the same days of collection. The surge of hLH (day 0) and the surge of hLHβcf (1–2 days later) were detected in urine, but the peak of hLHβcf lags behind hat of the intact hLH by 2–3 days, suggesting that the origin of urinary hLHβcf is a consequence of the peripheral or renal metabolic processing of intact hLH.

FIGS. 12A–12C.

Profile of woman JD classified as perimenopausal and analyzed by the hLHβcf urinary assay. Consecutive first morning void urines were collected. The first day of collection was at random and not correlated to first day of menses as the ten day collections. Both patient JD and patient MJU (see FIG. 13) were over 45 yrs old but were having regular menstrual cycles. Both women have two LH surges and two ovulations as shown by the middle pattern of steroids. The women were followed over time. Patient JD who displayed a clear postmenopausal-like pattern of hLHβcf concentration in urine, began to experience irregular cycles within six months of this collection and became postmenopausal within two years.

FIGS. 13A–13C.

Patient MJU was classified as perimenopausal. FIG. 13A shows the hLHβcf pattern observed in first morning void urines collected in 1991. This pattern is similar to that observed for premenopausal women. MJU is still not postmenopausal at the present time but is experiencing irregular cycles. Conventional urinary measurements of hLH by the Delfia assay did not show differences between patient JD (see FIG. 12) and patient MJU while the hLHβcf assay of the present invention correctly predicted that JD was closer (exhibited temporal proximity) to menopause despite having regular cycles at the time or urine collection. Additional patients exhibited similar profiles.

FIGS. 14A–14F.

Figure 14A:
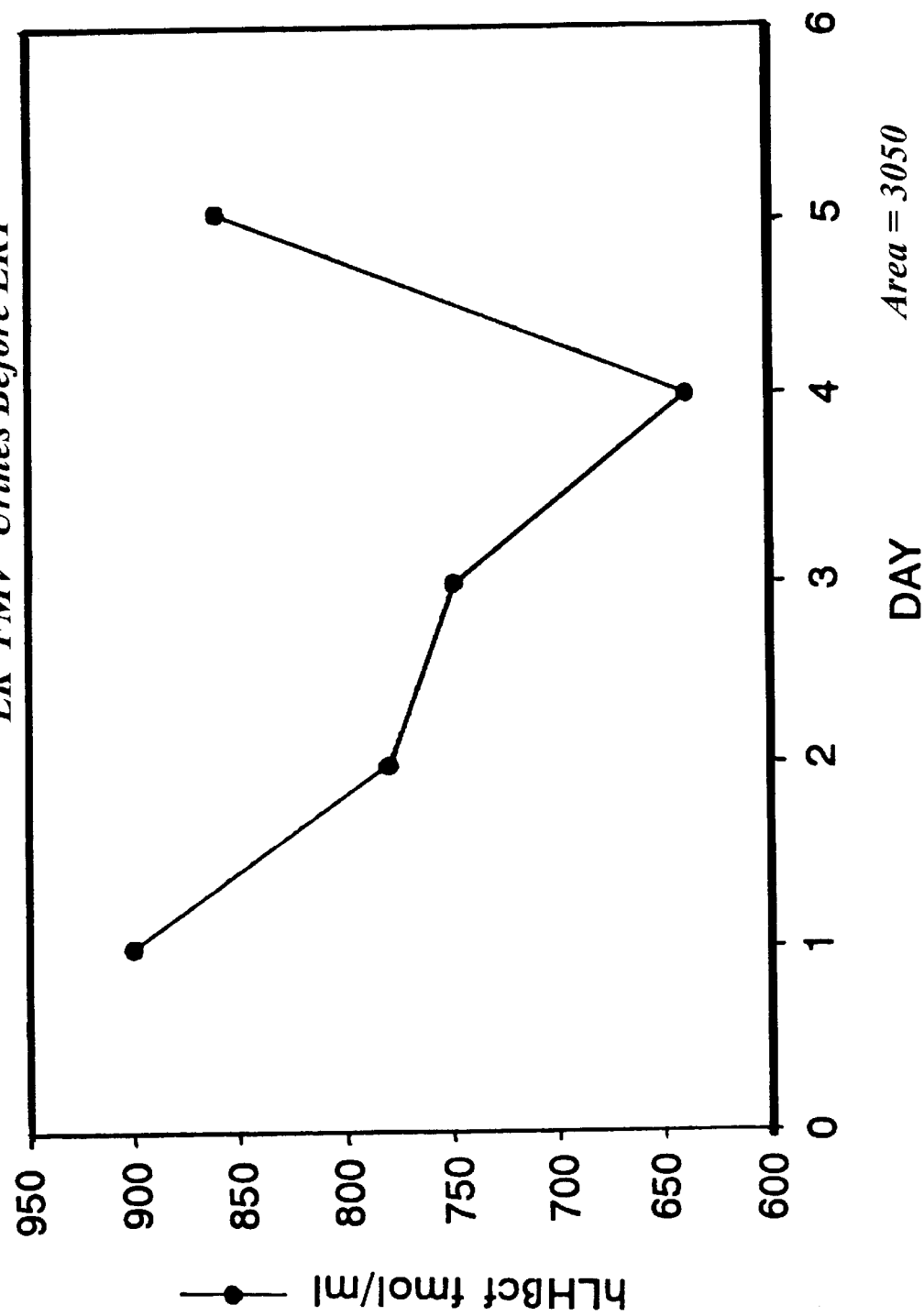
Figure 14B:
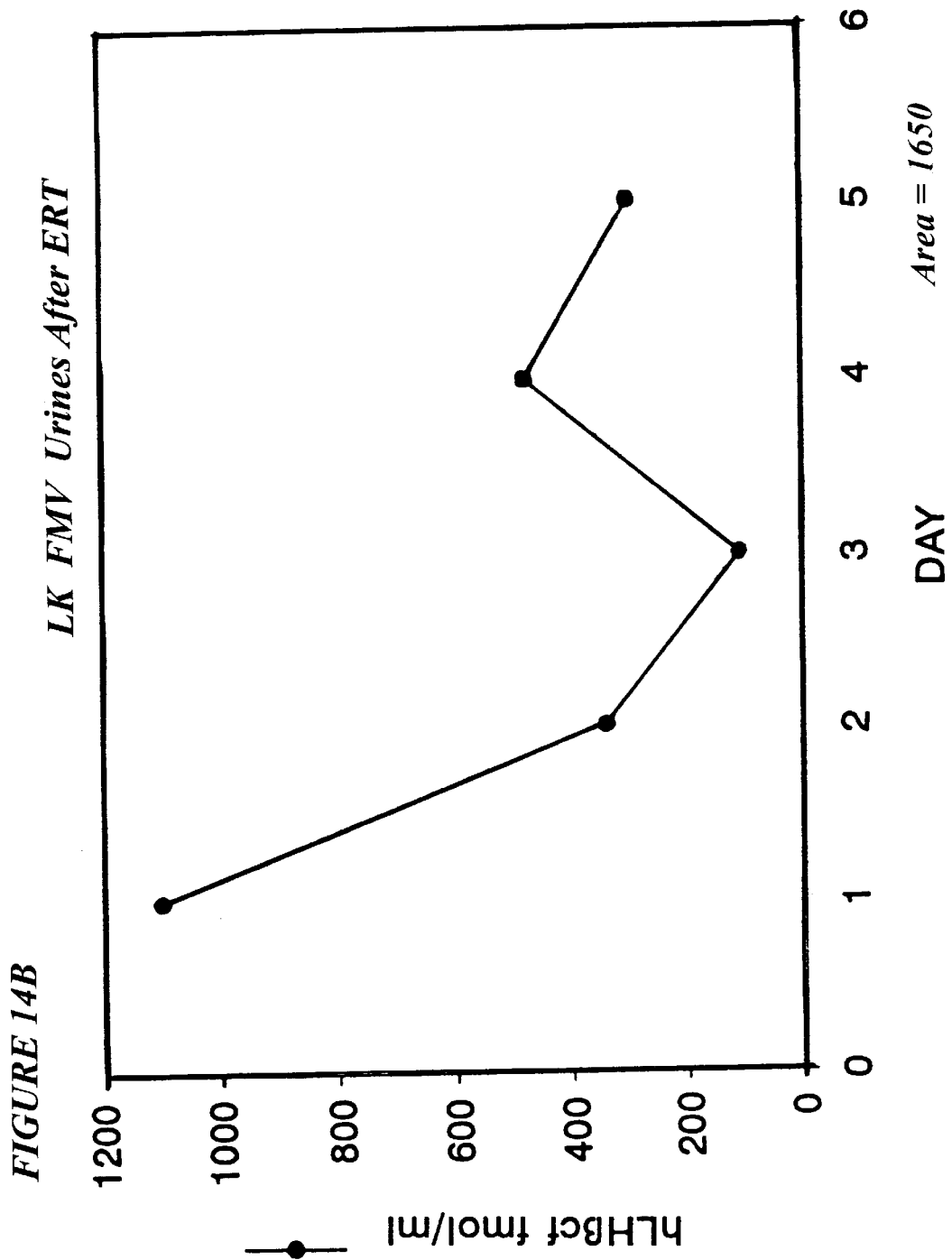
Figure 14C:
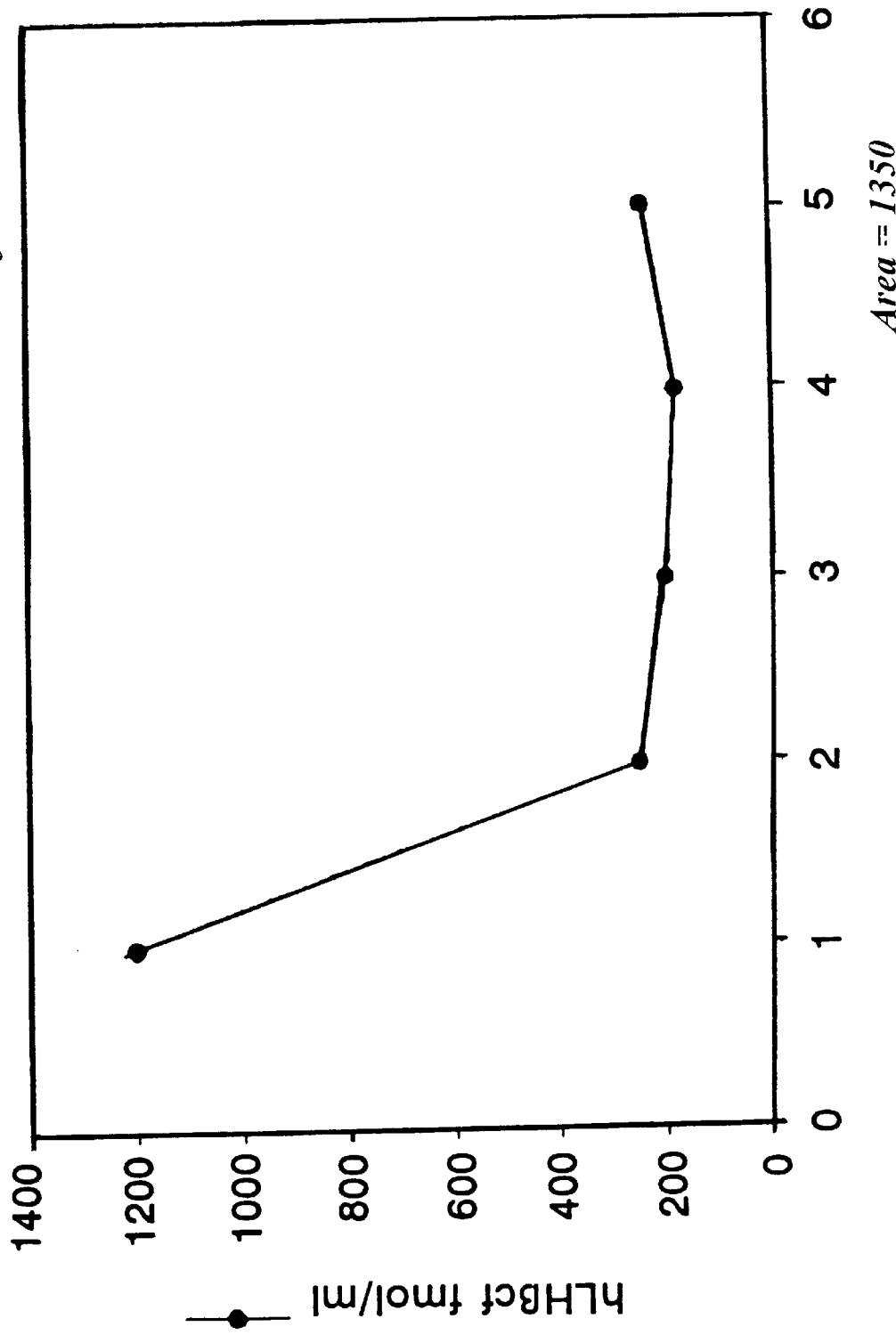
Figure 14D:
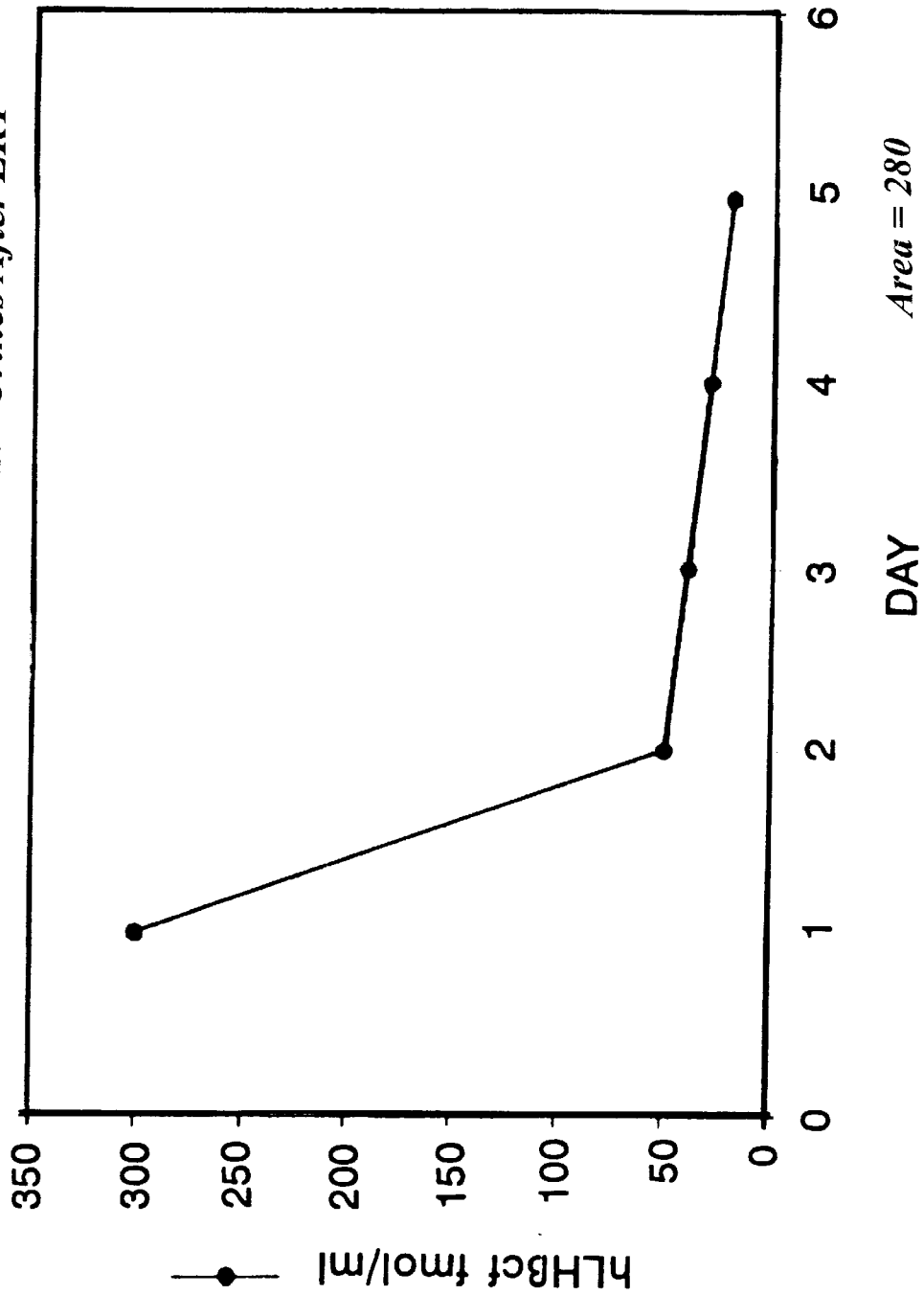
Figure 14E:
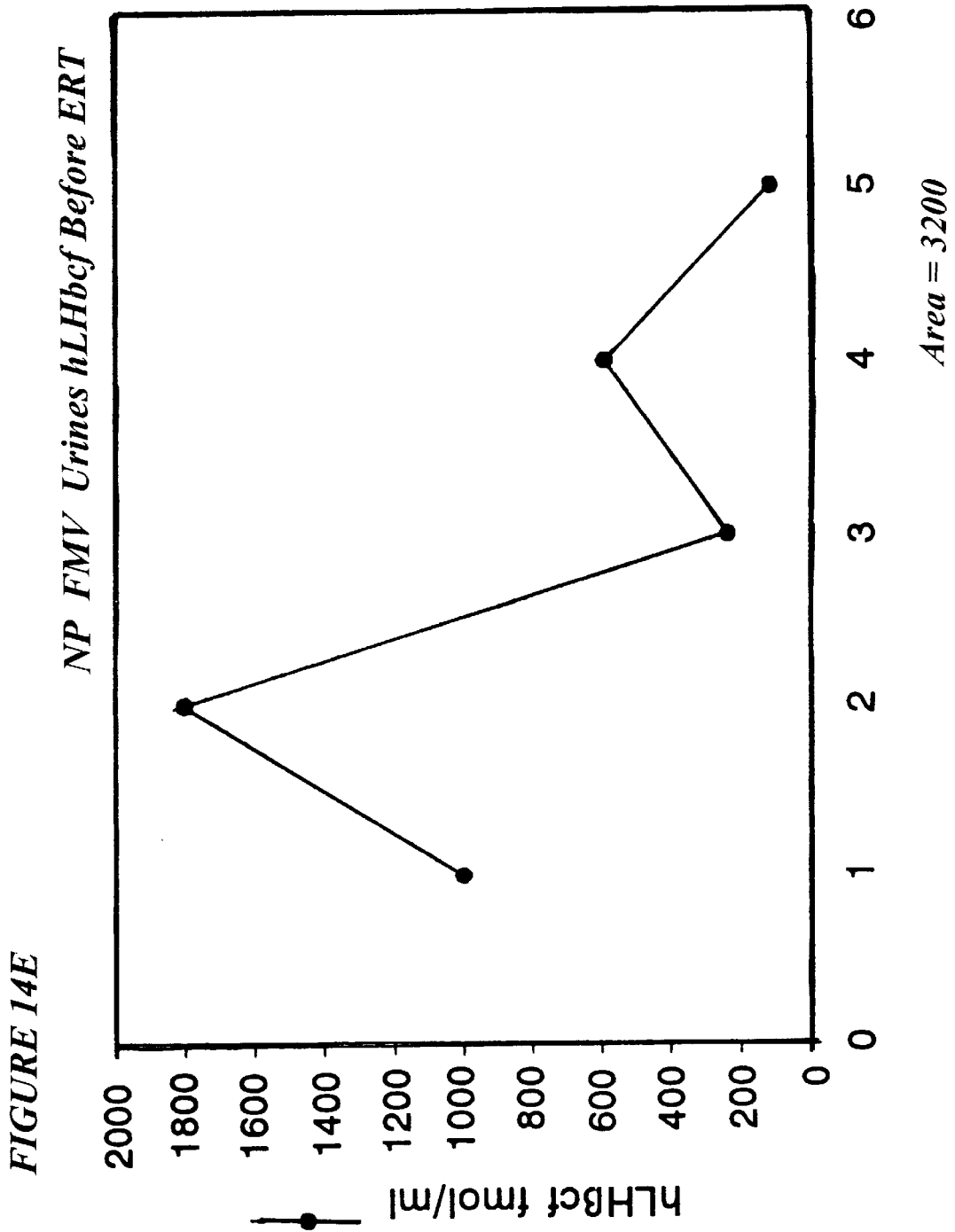
Figure 14F:
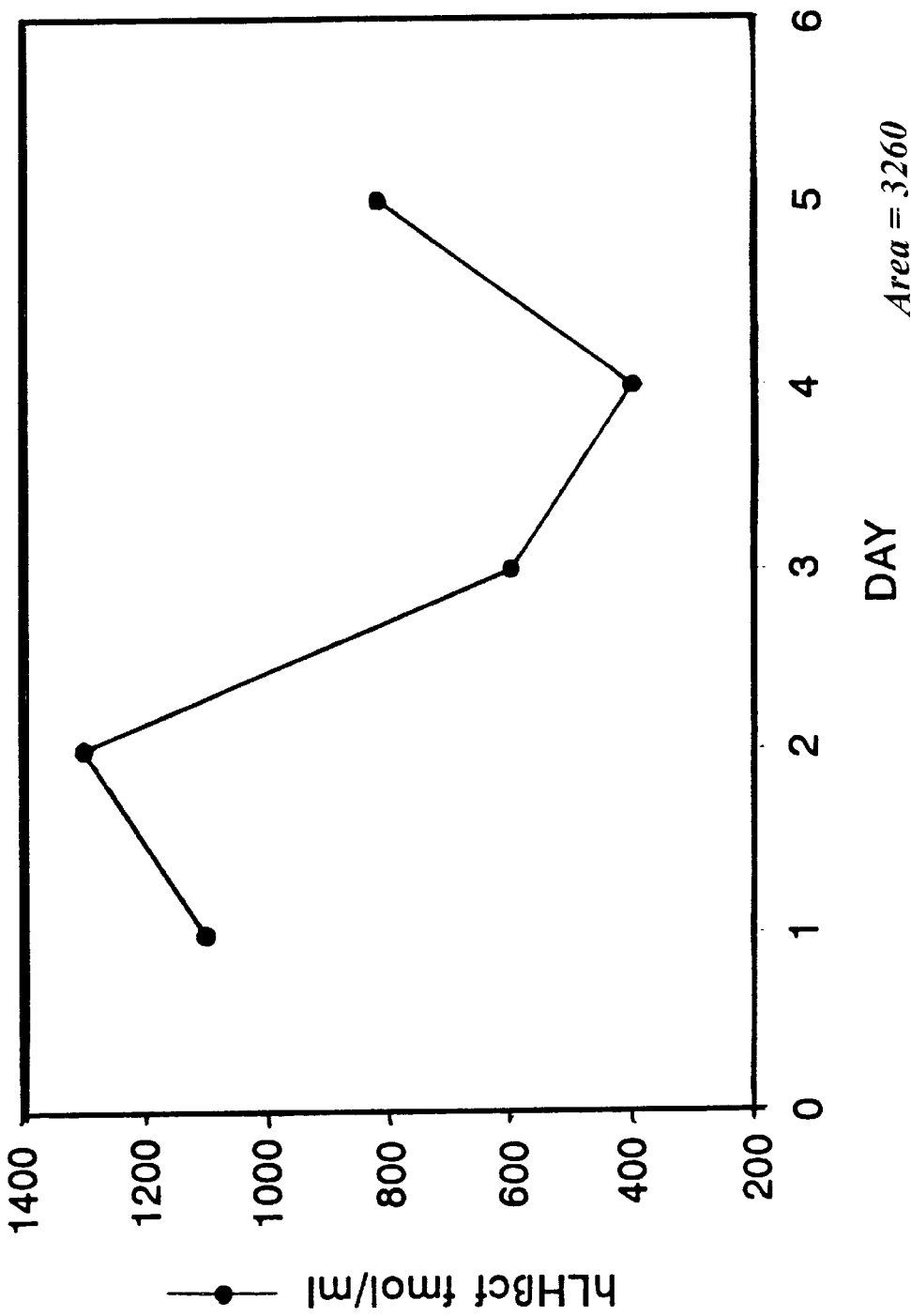

Measurements of the concentration of hLHβcf in the first morning void urine of three women before Estrogen replacement therapy (ERT) (FIGS. 14A,14C,14E) and after ERT (FIGS. 14B,14D,14F) . The area under the curve was calculated and is indicated. The profile for patient LK displays an area under the curve of 3050 before ERT and 1650 after ERT (FIGS. 14A–14B). The profile for patient VP displays an area under the curve of 1350 before ERT and 280 after ERT (FIGS. 14C–14D). The profile for patient NP displays an area under the curve of 3200 before ERT and 3260 after ERT (FIGS. 14E–14F).

FIGS. 15A–15C.

Immunochemical characterization of first morning void daily samples for a 60 day interval of a woman considered perimenopausal in 1991. The upper panel A is a graph of the hLHβcf urinary concentration each day (normalized to creatinine) while the middle panel B is that of steroid conjugates E1 and PDG. The lowest panel C shows the urinary hLH concentration as measured by DELFIA assay. This pattern resembles that of premenopausal women.

FIGS. 16A–16B.

Panel A. Pattern of hLHβcf concentration in first morning void samples of a postmenopausal woman. The assay was conducted twice ($1^{st}$ and $2^{nd}$ runs as indicated on Y-axes) with a time separation of 6 weeks. This study indicates the stability of the urinary hLHβcf measurement over time and between assays. Panel B. Urinary hLH as measured by the DELFIA assay (see methods).

FIGS. 17A–17B.

Young woman with premature ovarian failure. Panel A. Typical postmenopausal concentrations of the hLHβcf are observed in this 60 day first morning void urine collection. Panel B represents hLH measurements made by the DELFIA assay (see methods). There is no pattern match between urinary hLH and urinary hLHβcf (considering the expected 1–2 day delay in hLHβcf excretion after a surge of circulating hLH).

FIGS. 18A–18C.

Immunochemical characterization of first morning void samples of a perimenopausal woman with data presented as described in the legend to FIG. 1. Panel A show hLHβcf measurements that are similar to those in postmenopausal women. Panel 3 show patterns of urinary steroid conjugates of estriol and progesterone. Panel C illustrates measurement of urinary hLH by the DELFIA assay (see methods).

FIGS. 19A–19C.

Patterns of excretion of the hLHβcf in first morning void collections of three women. Panel A, premenopausal; Panel B, perimenopausal; Panel C, postmenopausal. Premenopausal is always easily distinguished from postmenopausal based on the concentrations of hLHβcf and the area under the peaks. The perimenopausal women fall in between. In this case, the perimenopausal woman resembles the postmenopausal pattern and is presumed to be close to menopause.

FIGS. 20A–20E.

Graphs are presented for 5 postmenopausal women who were asked to collect samples of each urination during a 2 day time period. The concentration of the hLH beta core fragment appears on the Y-axis while the time of collection, as a 24 hour clock, appears on the X-axis. It appears that collection of urine specimens during the day is quite similar in pattern to the 10 day first morning void urine collection protocol. It may be possible to conduct the sampling design in a more convenient fashion by sampling consecutive urine specimens for a 1–2 day period of time rather than over 5–10 days.

DETAILED DESCRIPTION OF THE INVENTION

This invention provides a method for predicting the likely timing of the onset of menopause for a premenopausal female subject by determining the amount of hLHβcf in a sample from the subject comprising the steps of: (a) contacting a sample from the subject with an antibody which specifically binds to hLHβcf without substantially cross-reacting with hLH, hLHβ or hCGβcf, under conditions permitting formation of a complex between the antibody and hLHβcf; (b) measuring the amount of complex formed, so as to thereby determine the amount of hLHβcf in the sample; and (c) comparing the amount of hLHβcf in the subject's sample determined in step (b) with either (i) the amount determined for known postmenopausal female subject or (ii) the amount determined for a sample from a known premenopausal female subject, wherein an amount of hLHβcf in the sample similar to the amount of hLHβcf in the known postmenopausal sample indicates temporal proximity to the onset of menopause, and an amount of hLHβcf in the sample similar to the amount of hLHβcf in the known premenopausal sample indicates temporal distance from the onset of menopause for the subject. As described herein amount is both concentration and pattern of measurement of concentrations in one or more consecutive urine specimens.

In an embodiment of this invention step (a) comprises contacting the sample with an antibody which specifically binds a region of hLHβcf comprising a protein and carbohydrate moiety.

In a further embodiment the antibody is monoclonal antibody B505 produced by hybridoma B505 (ATCC No. 12000).

In a further embodiment, step (a) the antibody is bound to a solid support and in step (b) the amount of the antibody bound to the solid support in the complex with hlHβcf is measured by contacting the complex with a second antibody which binds to the complex and which is labeled with a detectable marker.

In a further embodiment the sample is a urine sample, a first morning void urine sample, an aggregate sample of the first morning void urine samples for at least two consecutive days, an aggregate sample of the first morning void urine samples for five or more consecutive days, or a collection of all urinations consecutively with time noted for 24–48 hours.

In a further embodiment, the detectable marker is a radioactive isotope, enzyme, dye, magnetic bead, or biotin In a further embodiment the detectable marker is the radioactive isotope $I^{125}$.

This invention further provides a method for predicting the likely timing of the onset of menopause for a premenopausal female subject comprising the steps of: (a) contacting a urine sample from the subject with a capturing antibody which specifically binds to hLHβcf without substantially cross-reacting with hLH, hLHβ or hCGβcf under conditions permitting binding of the antibody with any hLHβcf present in the sample wherein the capturing antibody is bound to a matrix (b) separating hLHβcf bound to the matrix bound capturing antibody from hLHβcf not so bound; (c) contacting the hLHβcf bound matrix to the capturing antibody with a second antibody which specifically binds to hLHβcf that is bound to the capturing antibody without cross reacting with hLH, hLHβ or hCGβcf under conditions permitting binding of the second antibody to hLHβcf bound to the capturing antibody; (d) measuring the amount of the second antibody bound to the hLHβcf that is bound to the matrix bound capturing antibody so as to thereby determine the amount of hLHβcf in the sample; and (e) comparing the amount of hLHβcf in the subject's sample determined in step (d) with either (i) the amount determined for a sample from a known postmenopausal female subject or (ii) the amount determined for a sample from a known premenopausal female subject, wherein an amount of hLHβcf in the sample similar to amount of hLHβcf in the known postmenopausal sample indicates temporal proximity to the onset of menopause, and the amount of hLHβcf in the sample similar to the amount of hLHβcf in the known premenopausal sample indicates temporal distance from the onset of menopause for the subject. As described herein amount is both concentration and pattern of measurement of concentrations in one or more consecutive urine specimens.

In one embodiment the capturing antibody specifically binds a region of hLHβcf comprising a protein portion and a carbohydrate moiety In a further embodiment, the capturing antibody is monoclonal antibody B505 produced by hybridoma B505 (ATCC No. 12000).

In a further embodiment separating hLHβcf bound to the matrix bound capturing antibody from unbound hLHβcf comprises the steps of (a) removing of the sample from contact with the matrix; and (b) washing the matrix with an appropriate buffer to remove unbound hLHβcf.

In a further embodiment the sample is a urine sample, a first morning void urine sample, an aggregate sample of the first morning void urine samples for at least two consecutive days, an aggregate sample of the first morning void urine samples for five or more consecutive days, or a collection of all urinations consecutively with time noted for 24–48 hours.

In yet a further embodiment the second antibody labeled with a detectable marker is monoclonal antibody B503 or B504 produced by hybridoma B503 (ATCC No.11999) and B504 (ATCC No. 12002) respectively.

In a further embodiment a radioactive isotope, enzyme, dye, magnetic bead, or biotin.

In a further embodiment radioactive isotope is $I^{125}$.

This invention further provides a method for determining the likely timing of the onset of menopause for a perimenopausal female subject comprising: (a) obtaining a series of samples from the female subject over a period of time; and (b) determining the amount of hLHβcf in each of the samples, the presence of elevated levels of basal hLHβcf in each of the samples indicating that the onset of menopause in the subject is likely to occur in the near future. As described herein amount is both concentration and pattern of measurement of concentrations in one or more consecutive urine specimens.

In a further embodiment step (b) comprises: (a) contacting a sample from the subject with an antibody which specifically binds to hLHβcf without substantially cross-reacting with hLH, hLHβ, or hCGβcf, under conditions permitting formation of complex between the antibody and hLHβcf; and (b) measuring the amount of complex formed, so as to thereby determine the amount of hLHβcf in the samples; and (c) comparing the amount of hLHβcf in the subject's sample determined in step (b) with either (i) the amount determined for known postmenopausal female subject or (ii) the amount determined for a sample from a known premenopausal female subject, the stable presence of elevated levels of basal hLHβcf indicating temporal distance from the onset of menopause in the subject. As described herein amount is both concentration and pattern of measurement of concentrations in one or more consecutive urine specimens.

In a further embodiment in step (a) the antibody is bound to a solid support and in step (b) the amount of the antibody bound to the solid support in the complex with hlHβcf is measured by contacting the complex with a second antibody which binds to the complex and which is labeled with a detectable marker.

In a further embodiment the sample is a urine sample, a first morning void urine sample, an aggregate sample of the first morning void urine samples for at least two consecutive days an aggregate sample of the first morning void urine samples for five or more consecutive days, or a collection of all urinations consecutively with time noted for 24–48 hours.

In a further embodiment the second antibody labeled with a detectable marker is monoclonal antibody B503 or B504 produced by hybridoma B503 (ATCC No. 11999) and B504 (ATCC No. 12002) respectively.

In a further embodiment the detectable marker is a radioactive isotope, enzyme, dye, magnetic bead, or biotin.

In a further embodiment the detectable marker is the radioactive isotope is $I^{125}$.

This invention further provides a method for assessing ovarian function in a subject comprising the steps of: (a) contacting a sample from a subject with an antibody which specifically binds to hLHβcf without substantially cross-reacting with hLH, hLHβ or hCGβcf, under conditions permitting formation of a complex between the antibody and hLHβcf; (b) measuring the amount of complex formed, so as to thereby determine the amount of molecule in the sample; and (c) comparing the amount of hLHβcf in the subject's sample determined in step (b) with either (i) the amount determined for a sample from a subject with normal ovarian function or (ii) the amount determined for a sample from a subject with abnormal ovarian function, wherein an amount of hLHβcf in the sample similar to amount of hLHβcf in the sample from subjects having normal ovarian function indicates normal ovarian function, and amounts of hLHβcf in the sample similar to amounts of hLHβcf having abnormal ovarian function indicates abnormal ovarian function for the subject. As described hereon amount is both concentration and pattern of measurement of concentrations in one or more consecutive urine specimens.

In a further embodiment in step (a) the antibody is bound to a solid support and in step (b) the amount of the antibody bound to the solid support in the complex with hlHβcf is measured by contacting the complex with a second antibody which binds to the complex and which is labeled with a detectable marker.

In a further embodiment the sample is a urine sample, a first morning void urine sample, an aggregate sample of the first morning void urine samples for at least two consecutive days or an aggregate sample of the first morning void urine samples for five or more consecutive days, or a collection of all urinations consecutively with time noted for 24–48 hours.

In a further embodiment the abnormal ovarian function is hyperactivity or hypoactivity.

In a further embodiment the second antibody labeled with a detectable marker is monoclonal antibody B503 or B504 produced by hybridoma B503 (ATCC No. 11999) or B504 (ATCC No. 12002) respectively.

In a further embodiment the detectable marker is a radioactive isotope, enzyme, dye, magnetic bead, or biotin.

In a further embodiment the detectable marker is the radioactive isotope is $I^{125}$.

This invention further provides a method for determining the efficacy of hormone replacement therapy in a premenopausal female subject comprising the steps of: (a) contacting a sample from the subject with an antibody which specifically binds to hLHβcf without substantially cross-reacting with hLH, hLHβ or hCGβcf, under conditions permitting formation of a complex between the antibody and hLHβcf; (b) measuring the amount of complex formed, so as to hereby determine the amount of hLHβcf; and (c) comparing the amount of hLHβcf measured in step (b) with either (i) the amount determined for a sample from a subject taken prior to the commencement of therapy or (ii) the amount determines for a sample after a prior course of therapy (iii) the amount determined for a sample from a known premenopausal female subject or (iv) the amount determined for a sample from a known postmenopausal female, wherein differences in the amounts of hLHβcf in the sample indicate efficacy of the hormone replacement therapy for the subject; amounts of hLHβcf in the sample similar to amounts of hLHβcf samples from known premenopausal subjects indicates efficacy of the hormone replacement therapy for the subject; amounts of hLHβcf molecule in the sample similar to amounts of hLHβcf in the sample from known postmenopausal subjects indicates lack of efficacy of the hormone replacement therapy for the subject. As described herein amount is both concentration and pattern of measurement of concentrations in one or more consecutive urine specimens.

In a further embodiment in step (a) the antibody is bound to a solid support and in step (b) the amount of the antibody bound to the solid support in the complex with hlHβcf is measured by contacting the complex with a second antibody which binds to the complex and which is labeled with a detectable marker.

In a further embodiment the sample is a urine sample, a first morning void urine sample, an aggregate sample of the first morning void urine samples for at least two consecutive days, or an aggregate sample of the first morning void urine samples for five or more consecutive days, or a collection of all urinations consecutively with time noted for 24–48 hours.

In a further embodiment the replacement hormone therapy comprises therapy with estrogen and second antibody labeled with a detectable marker is monoclonal antibody B503 or B504 produced by hybridoma B503 (ATCC No. 11999) and B504 (ATCC No. 12002) respectively.

In a further embodiment detectable marker is a radioactive isotope, enzyme, dye, magnetic bead, or biotin.

In a further embodiment the detectable marker is the radioactive isotope is $I^{125}$.

Finally, this invention provides a diagnostic kit for predicting the likely timing of the onset of menopause for a premenopausal female subject by determining the amount of hLHβcf in a sample from the subject comprising: (a) a solid matrix to which an antibody which specifically binds to hLHβcf without substantially cross-reacting with hLH, hLHβ or hCGβcf, under conditions permitting formation or a complex between the antibody and hLHβcf is bound; and (a) a second antibody labeled with a detectable marker; and (a) reagents permitting the formation of a complex between the antibody and hLHβcf. As described herein amount is both concentration and pattern of measurement of concentrations in one or more consecutive urine specimens.

In a further embodiment the diagnostic kit of further comprises control sample(s) selected from the group consisting of premenopausal sample(s), perimenopausal sample (s), postmenopausal sample(s) and male sample(s).

In a further embodiment the second antibody in the diagnostic kit labeled with a detectable marker is the monoclonal antibody B503 or B504 produced by hybridomas B-503 (ATCC No. 11999) and B504 (ATCC No. 12002) respectively.

In a further embodiment the detectable marker in the diagnostic kit is a radioactive isotope, enzyme, magnetic bead, dye or biotin.

In a further embodiment detectable marker in the diagnostic kit is the radioactive isotope is $I^{125}$.

A monoclonal antibody, B-505, is produced by the hybridoma cell designated ATCC accession No. HB-12000. This hybridoma cell line was deposited on Dec. 11, 1995 with the American Type Culture Collection (ATCC), 10801 University Boulevard, Manassas, Va. 20110-2209, U.S., under the provision of the Budapest Treaty for the International Recognition of the Deposit of Microorganism for the Purpose of Patent Procedure.

hLH beta core fragment (hLHβcf), isolated from human pituitaries is homologous to the hCG beta core fragment (hCGβcf). Antibodies to the hLHβcf, have been developed which are applied in sensitive assays including immunoradiometric assays for urinary measurements. One of the antibodies recognizes an epitope on the hLHβcf, which is not present on the hCGβcf, hLH, or hLHβ. This specific hLHβcf antibody acts cooperatively with other newly-developed antibodies to produce an assay with a sensitivity of 1 fmol/ml of hLHβcf. This specificity makes it possible to measure hLHβcf in urine in the presence of hLH, hLH beta, or the hCGβcf. Although the hLHβcf used to develop specific antibodies was purified from pituitaries, the assays developed recognize this metabolite in urine. Measurements of heterodimeric hLH as compared to hLHβcf in the urine of cycling women indicated that the concentration of hLHβcf rose as high as 6–7 times the concentration of hLH starting a day after the midcycle surge. The novel measuring systems described herein allow the precise quantitation of this hLH metabolite in urine.

Three groups of women were analyzed: young cycling premenopausal, perimenopausal (as defined by current clinical and age-related criteria), and postmenopausal women. The appearance of the hLHβcf in the urine of all three groups of women was pulsatile on a daily basis when measured in first morning void urine specimens. This was unexpected since hLH was pulsatile on an hourly basis in blood. Both the pattern of pulsatility and the amplitude of the pulses differed between young cycling women and postmenopausal women. Statistical analyses indicated that the wide range of differences between postmenopausal and premenopausal women made it possible to discriminate among the three groups of women. Postmenopausal women can be sampled for any ten day interval while cycling women can be sampled during the follicular phase. Data indicates drastically different qualitative and quantitative patterns of premenopausal and perimenopausal patients closest to menopause. Perimenopausal women displayed postmenopausal patterns in many cases. Women with premature ovarian failure exhibited a pattern similar to that seen for postmenopausal women, but with a distinguishing higher levels of hLH metabolite. Treatment of women with GnRH agonist peptide appeared to expel the hLH β core fragment directly from the pituitary. This demonstrates potentially two origins of this molecular form of hLH, both directly from the pituitary and from breakdown of circulating hLH in the kidney or other peripheral tissue compartments. A chromatographic technique was developed to separate the hLHβ core fragment generated in the pituitary from that which usually appears in the urine of postmenopausal women.

This invention is illustrated in the Experimental Details section which follows. These sections are set forth to aid in an understanding of the invention but are not intended to, and should not be construed to, limit in any way the invention as set for th in the claims which follow thereafter.

EXPERIMENTAL DETAILS

EXAMPLE 1

Predicting Onset of Menopause Using a Urinary hLH B Core Fragment Assay

Measuring hLH β Core Fragment in Urine

Although immunological evidence indicated the presence of a β subunit fragment or hLH in the urine of postmenopausal women, no direct evidence that the molecules came from hLH and not from hCG was available until now (Iles, et al., 1992; Kovalevskaya, et al., 1995; Neven, et al., 1939). The presence of this approximately 10,000 M.W. molecule was apparent on gel filtration chromatography and presented a background threshold problem in the application of assays for the hCG β core fragment as a potential cancer marker in postmenopausal women (O'Connor, et al. 1994; Iles, et al., 1992; Birken, et al., 1993; Kovalevskaya, et al., 1995; Neven, et al., 1993). The specific measurement system for such a fragment from hLH differentiates it from the homologous fragment from hCG β which is known to be present at high levels in the urine of pregnant women and in patients with hCG-secreting cancers including a variety of cancers of the reproductive system (O'Connor, et al. 1994; Stenman, e. al., 1993 ; de Medeiros, and Norman, 1991; Birken, et al, 1993; Kovalevskaya, et al., 1995; Lee, et al., 1991; Krichevsky, et al., 1991). Using pituitary tissue extracts as starting material, an hLH β core fragment whose structure appears in FIG. 1 was successfully isolated. The specific measuring systems for the hLH β core fragment can be used in the presence of the hCG β core fragment as well as in the presence of hLH (Kovalevskaya, et al., 1995). The hLH β core fragment assay can measure 1.3 fmol/ml of this epitope and cross-reacts only 1% with hLH β core fragment and less than 1% with hCG β core fragment. A MALDI-TOF delayed extraction reflector mass spectrometer has been employed to visualize the sizes of the hCG and hLH β core fragments which are both broad peaks of 9500–10000 AMU. It has been possible to measure the size of the urinary form of the hLH β core fragment (also 10K in a partially purified preparation).

The β fragment of hLH from human pituitaries (see, FIG. 1, Seq.ID.No.:1) has been isolated and sensitive and specific two-site assays to this molecule have been developed (Eirken, et al., 1993; Kovalevskaya, et al., 1995). The hLH β core fragment is homologous to the hCG fragment. The hLH β core fragment, isolated from a pituitary extract and its structure is slightly heterogeneous and is composed of residues 6–40 linked to 49–93 or 55–93 (Birken, et al., 1993). The hLH β core fragment is clearly detected in postmenopausal urine at high concentrations using antibodies to the similar metabolite of hCG (Iles, et al., 1992; Neven, et al., 1993). The hLHβcf epitope in urine is highly stable as is the hCG metabolite making it a very useful urinary marker. Subunit dissociation is not a problem with stable markers.

A very important characteristic of useful urinary assays is stability of the analyte. The hLHβcf exhibits a stable profile, making it far superior to the use of heterodimeric hormones. Parent hLH tends to dissociate, especially in urine. The stability of both the pituitary and the urinary forms of the hLHβcf is illustrated in Table I.

TABLE I

Storage Conditions for Stability Testing

| Molecular Form | −80 C | 29 days, 4 C | 29 days, 22 C | 1 day 37 C | 40 freeze/ thaws |
|---|---|---|---|---|---|
| Pit. hLHβcf | 153 +/− 7.6 | 162 +/− 7.8 | 163 +− 7.8 | 183 +/− 2.4 | 155 +/− 5.6 |
| Urinary hLHβcf | 243 +/− 34 | 199 +/− 11 | 203 +/− 13 | 290 +/− 7.7 | 211 +/− 21 | values expressed as means of concentrations of fmol/ml +/− 1SD

In the urine of a normally cycling woman, hLHβcf appears starting with the LH surge and peaking generally 1–3 days after the urinary LH surge peak concentration. The urinary hLHβcf appears at concentrations 2–10 times that of hLH on a molar basis. Chromatographic separatory data based on different elution times on reverse phase high pressure liquid chromatography (HPLC) indicates that the urinary and pituitary forms of the hLHβcf differ. This difference may be within the carbohydrate moieties (see FIG. 2). The hCG β core fragment is known to contain sugar moieties trimmed down to their mannose cores while the pituitary hLH β core fragment appears to contain sulfate and resemble the structure of hLH in carbohydrate. The size of the urinary form on mass spectrometry resembles that of the pituitary homolog (10K). The urinary form of hLHβcf may have trimmed carbohydrate.

Although antibodies were developed to the pituitary form of the hLH β core fragment, the antibodies react with great sensitivity to the 10,000 M.W. fragment which is present in the urine of postmenopausal women. This fragment elutes with a midpoint of fraction 65 on the gel filtration profile of a postmenopausal urine concentrate on Superdex 200. The hLHβcf from both a human pituitary extract and postmenopausal urine would both appear at high concentration in the identical area of fraction 65.

Studies of a series of normal ovulatory cycles indicated that the measurement of the hLHβcf in urine is much easier than the hLH surge in urine because of: (1) the high concentration of fragment, (2) its stability, and (3) some monoclonal antibodies do not recognize all forms of hLH and can miss the hLH surge. The instability of hLH is illustrated by the daily urine profile of a normal cycling woman whose urine contains on detectable heterodimeric hLH but only hLHβ and hLHβcf. Studies of several ovulatory cycles shows that the hLH β core fragment is present at all times at a basal pattern level but as concentrations more than an order of magnitude lower than the hLHβcf found the urine of postmenopausal women (see FIGS. 3A–3K. This also illustrates paradigm o first morning void studies from day 1 of menses to day 10. While both premenopausal and postmenopausal women exhibit daily first morning urine hLHβcf concentrations in a pulsatile fashion, the concentrations are so dramatically different that summing areas under the peaks define non-overlapping area values allowing statistical differentiation of the two populations.

Figure 10:
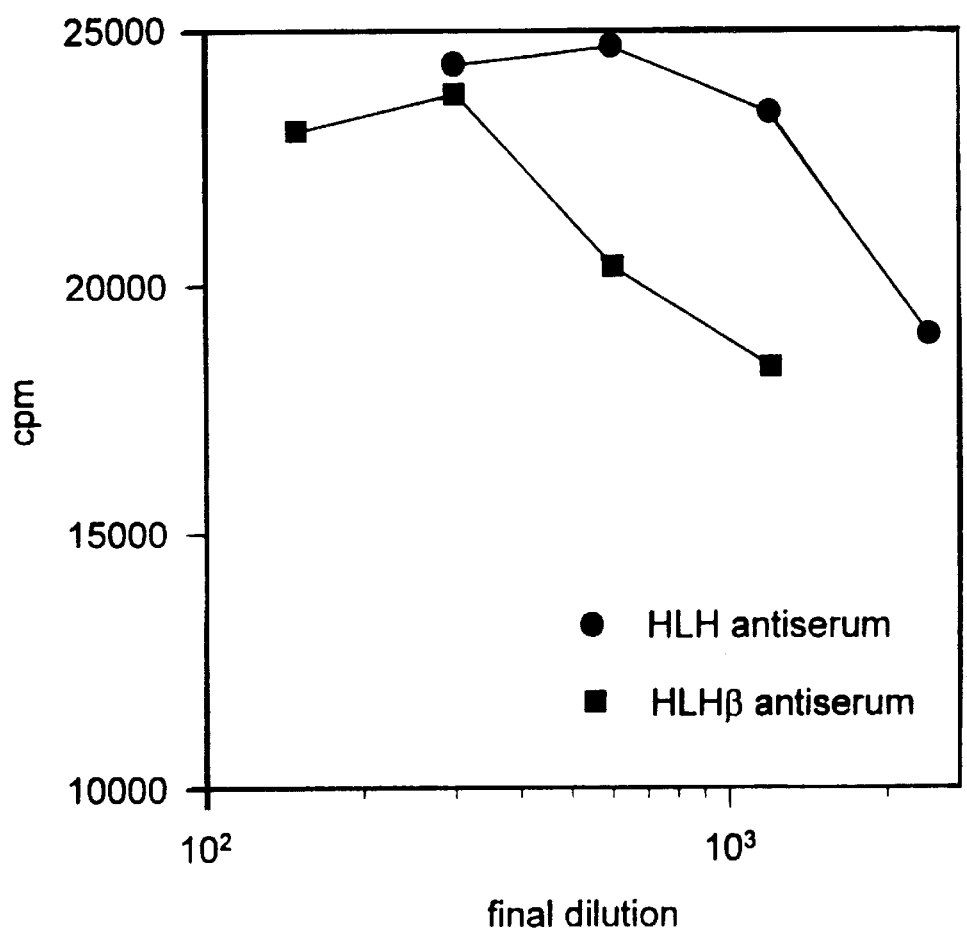

Daily first morning void urine specimens from peri menopausal and postmenopausal women for 60 consecutive days were measured urinary hLH with the Delfia FIG. 10 system as well as steroids and creatinine and validated the serum Delfia kit for urine measurements using added glycerol as a stabilizer for heterodimeric hLH (Saketos, et al., 1994). Several complete cycles from premenopausal women and a number of ten day first morning voids from postmenopausal women and follicular phase ten day collections from premenopausal women were also collected. Statistical analyses of these patterns were conducted by determining the area under the peak for a ten day interval and then performing least squares analysis of variance with pair-wise post hoc comparisons. Statistically significant differences, after Bonferroni correction was found for premenopausal/postmenopausal comparisons. Power analyses for this study, which consisted of ten consecutive first morning void urines, menstrual days 1–10 for premenopausal and perimenopausal women, required log-transformed values. The test populations consisted of 13 premenopausal women, four perimenopausal and eight postmenopausal.

Figure 4:
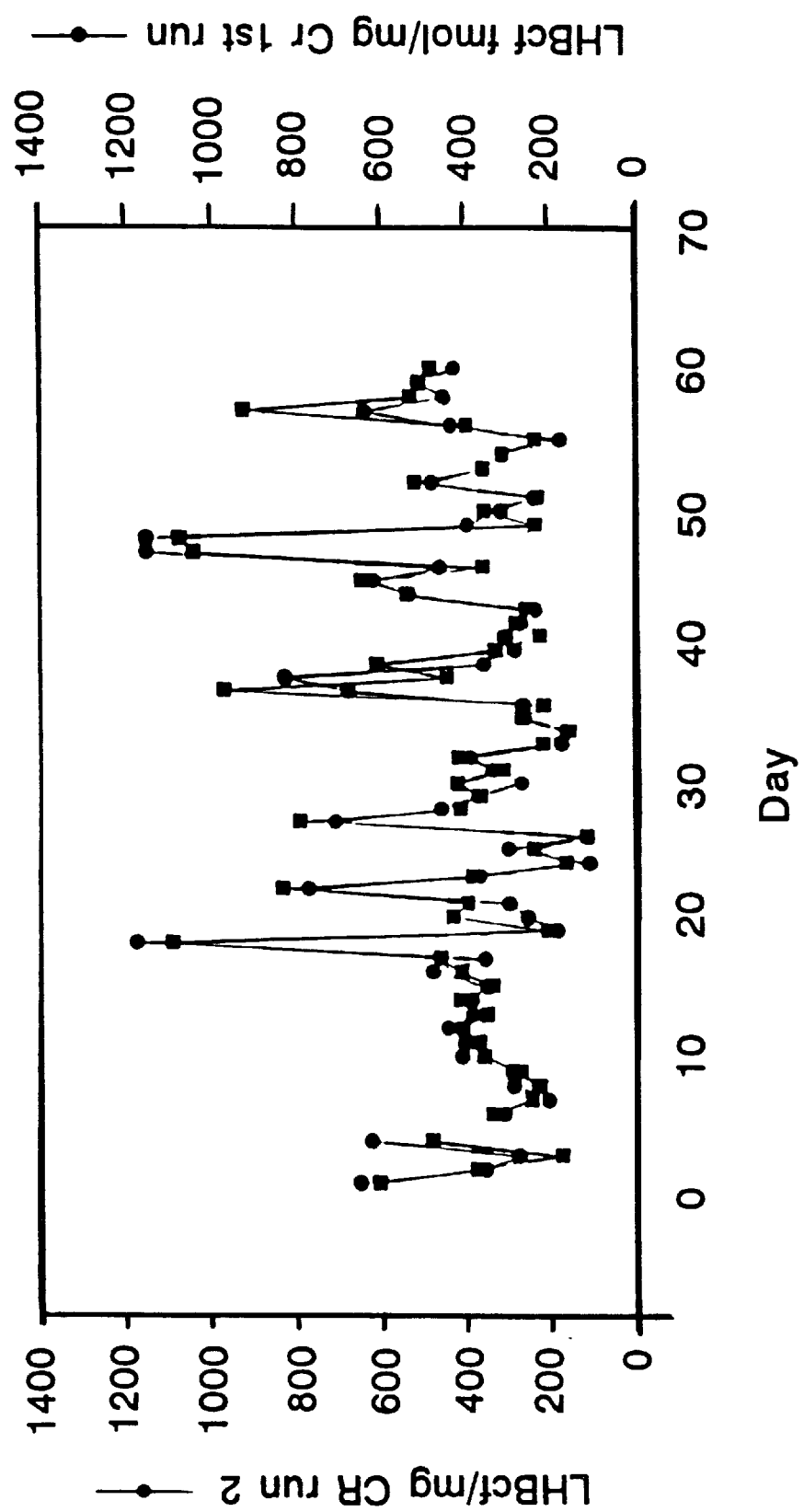
Figure 5A:
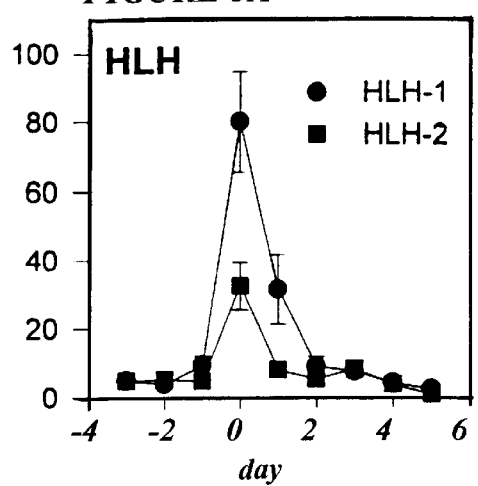
Figure 5B:
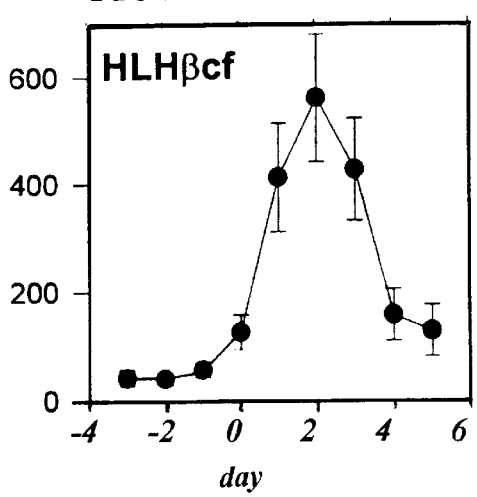
Figure 5C:
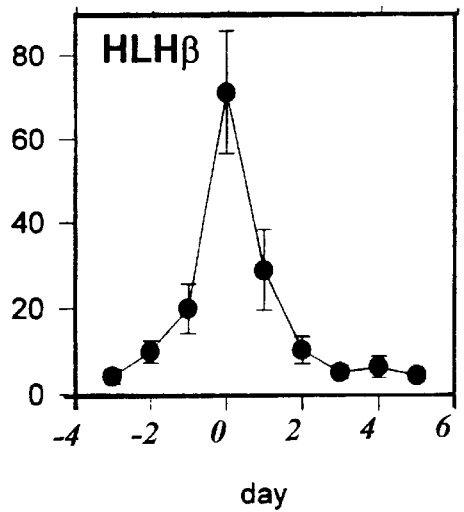
Figure 5D:
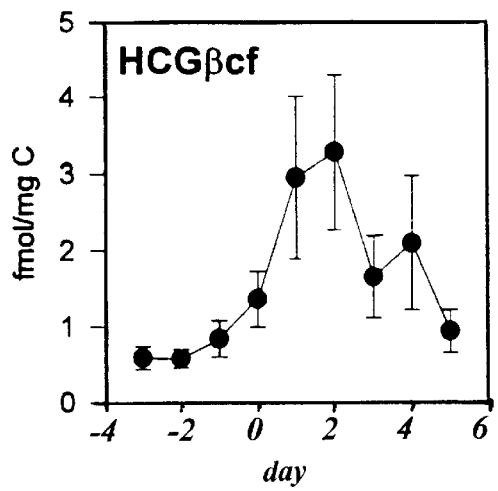
Figure 5E:
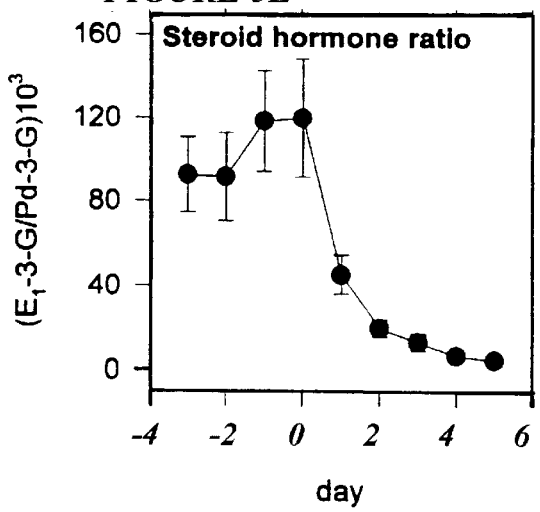

A 60 day random collection of first morning void urine from a postmenopausal woman was assayed (see FIG. 4). The assay was repeated twice on the same samples weeks later after freeze thaws. The identical pulsatile pattern with the same concentrations was observed.

Expression of Urinary hLHβcf

A cohort of women was studied (n=15). A peak of hLHβcf was observed to occur over a 3–4 day period, commencing on the day of hLH surge and reaching a maximum value of 560 (SE 119) fmo/mg creatinine at 1–3 days post urinary intact hLH peak (see FIG. 5). A peak of hLH free beta subunit (hLHβ) was observed to occur simultaneously with that of the intact molecule. Although the levels of hLHβ approximately those of the intact hormone, the levels of hLHβcf were several fold higher (see FIG. 5).

A surge of hCGβcf immunoreactivity peaked two days post intact hLH, generally coincident with the peak of hLHβcf. at levels which were 100 fold less than those for hLHβcf. Since the cross-reaction of the hCGβcf immunoassay with the pituitary hLHβcf was determined to be 1–2%, and that the true cross-reactivity with the urinary form is unknown, it may be that the total signal detected in the hCGβcf assay is in fact due to cross-reaction with hLHβcf (Birken et al. 1996).

The urinary hLH surge was detected by A407-B207 (hLH-1) antibody configuration. Eight of the 15 cycles were rerun in a different antibody configuration assay B406-A201 (hLH-2). These assays were constructed using monoclonal antibodies to different hLH epitopes (See Table III). Both hLH-1 and hLH-2 assays gave the same day of hLH surge, but the concentration of hLH in two assays differed significantly (paired t-test, P=0.0005).

This observation further illustrates that the levels of hormone detected immunologically in urine reflect the differential conservation (or stability) of hLH epitopes excreted into urine and caution that monoclonal antibodies may be too specific to provide an accurate estimation of the level of all forms co hLH in either blood or urine (Pettersson et al., 1991; Pettersson et al., 1992; Martin-Du-Pan et al., 1994; Costagliola et al., 1994; Mitchell et al., 1995; Barbe et al., 1995 Pettersson and Soderholm, 1991).

Figure 6:
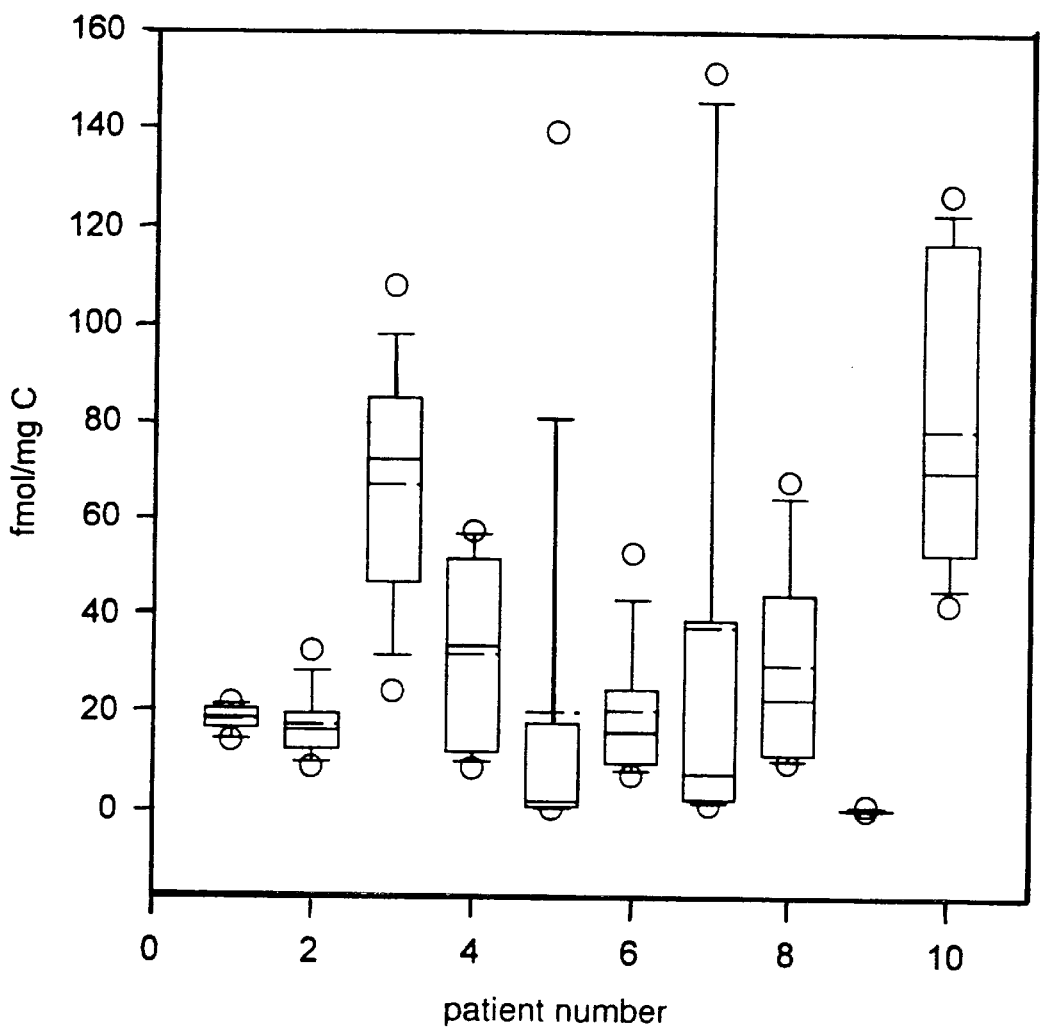

All cycles were characterized by irregular pulsations of hLHβcf. The basal level of hLHβcf in ten patients during first of the follicular phase (100 samples) was 32 (SE 4) fmo/mg creatinine, with a wide range of concentrations, reflecting the spikes of hLH occurring before the periovulatory surge of hLHβcf (FIG. 6).

Examination of daily first morning urines from four women in which the hLH assays, indicated that ovulation occurred as judged by the inversion of the urinary estrogen/progesterone metabolite ratio (Baird et al., 1991). Data from two of the four women are presented in (FIG. 7). Evidence from the urinary steroids that ovulation occurred suggested that one or more of the following occurred. The intact hormone may have been completely cleared by an alternative pathway. The intact hormone may have dissociated completely into subunits or been totally degraded into fragments prior to excretion. Alternatively, the antibodies used in these measurements, which were raised to the pituitary form of hLH, may have failed to recognize the urinary isoform of hLH present in the sample. That the lack of evidence for intact hLH was not a consequence of these subjects producing an isoform of hLH peak was found in other cycles tested from these subjects.

These cycles were characterized by the presence of a periovulatory peak of hLHβcf within the expected time interval. These results suggest that an assay incorporating the detection of all three urinary analytes would provide the most sensitive detection of periovulatory hLH. However, although hLHβ is most often observed to peak coincident with the intact molecule (FIG. 5), it appears that it can occasionally occur one day earlier (Kovalevskaya et al., 1995). On the other hand, hLHβcf, usually peaked 1–3 days later than the intact molecule (FIG. 5) and this midcycle peak of hLHβcf has been detected in all four cycles in which there was undetectable intact hLH in the urine (FIG. 7).

Figure 8:
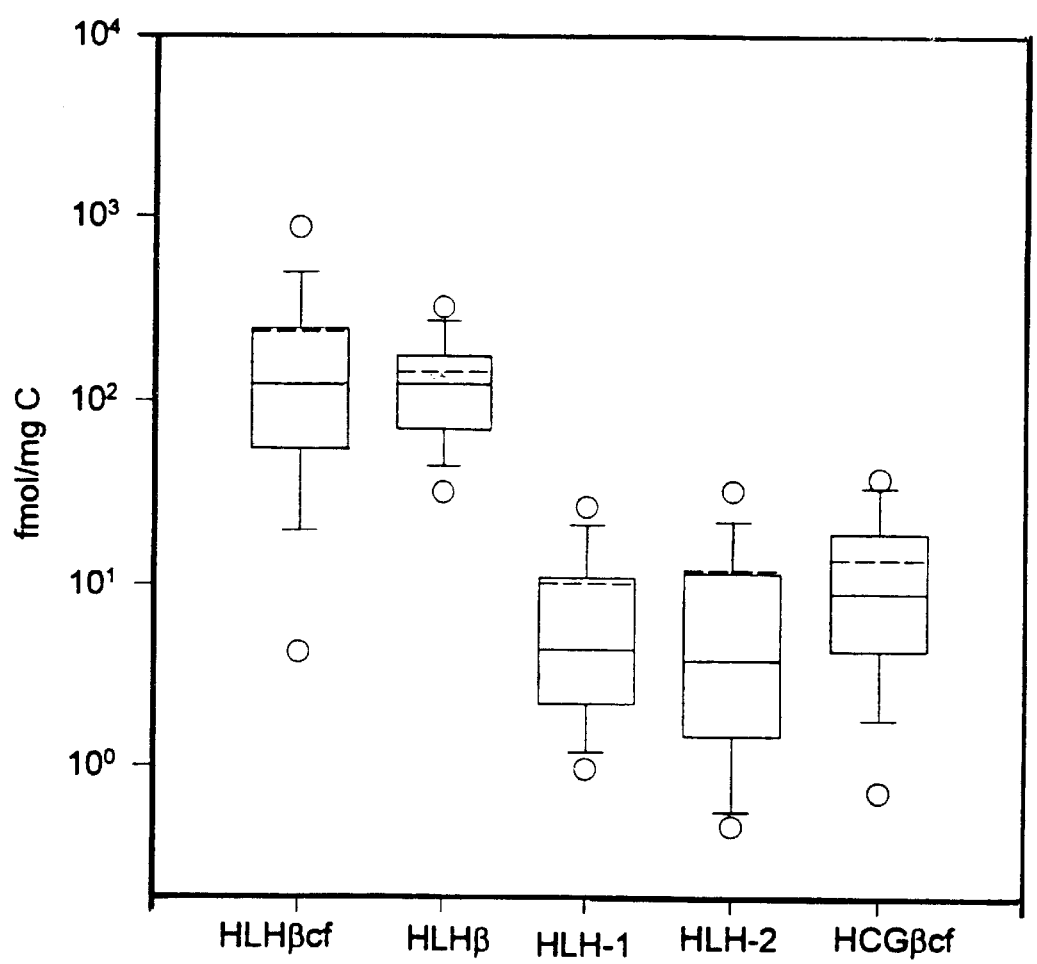

The levels of intact hLH, hLHβ, hLHβcf, and hCGβcf were evaluated in a total of 107 healthy postmenopausal women (FIG. 8). The mean concentration of hLHβcf for the 107 postmenopausal women was 236 (SE 35) fmol/mg creatinine.

Urines collected from eleven normal males (age 20–60) yield a value of 41 (SE 13) fmol/mg creatinine (See Table II).

TABLE II

Concentration of hLHβcf in Urine

| | Periovulatory urine, basal level | Periovulatory urine, surge | Post-menopausal urine | Male urine |
|---|---|---|---|---|
| Mean +/− SE, fmol/mg C | 32 +/− 4 | 560 +/− 119 | 236 +/− 35 | 41 +/− 13 |
| Size | 100* | 15 | 107 | 11 |

SE - standard error of mean; fmol/mg
C - concentration of hLHβcf normalized per mg creatinine;
* - days 1 to 10 from 10 women.

hLH and hLHβ were measured in urine using IRMA's incorporating specific monoclonal antibodies (FIG. 9A) and by RIA (FIG. 9B), using polyclonal antisera directed against either intact hLH or hLHβ, supplied by the National Hormone and Pituitary Program, NIDDKD. The RIA reagents were designed for serum assays and indicate a single day pre-ovulatory elevation of both hLH and occasionally hLHβ in blood.

When these same reagents are employed for hLH or hLHβ measurement in urine however, a broad peak for either hormone was obtained. These observations can be explained by the presence of hLHβcf in the urine (FIG. 9A). When FIGS. 9A and 9B are compared, it is apparent that the day of maximum hLHβ by IRMA is different from the RIA value, probably due to the greater cross-reactivity of the hLHβ polyclonal antiserum to hLHβcf.

The cross-reactivities of the polyclonal antisera to hLHβ and to intact hLH with hLHβcf were further evaluated in an RIA using hLHβcf labled with $I^{125}$ (FIG. 10). Both polyclonal antisera clearly recognized hLHβcf. The pituitary form of hLHβcf was used in this experiment but a similar reactivity pattern should also be observed with the urinary variant of this molecule, since the monoclonal antibodies developed to the pituitary material all appear to share epitopes present on the urinary molecule.

A comparison of the concentration of hLHβcf in blood and urine was undertaken by collecting paired samples beginning on the first day of the hLH surge in urine (detected by "First Response" kit) and continuing for three subsequent days in a single subject. The collection was repeated during a subsequent cycle. FIG. 11 illustrates corresponding values in blood and urine for hLH, hLHβ and hLHβcf. The hLH-1 assay provided a significantly stronger signal in serum than did the hLH-2 assay. The hLHβ signal appears synchronously with the intact peak in this subject in urine. However, the hLHβ surge starts to grow and is detected only in the urine.

The basal level (i.e. follicular level) of hLHβcf in normally cycling women was similar to the level which was detected for male urine (see Table II). Both of these groups differ markedly from the values obtained for postmenopausal subjects which were characterized both by much higher levels and a wider range of values (FIG. 8). Level of intact hLH were low in these subjects in both assays for hLH, but there was a substantial quantity of hLHβ, perhaps reflecting dissociation of the intact molecule. Only low values of hCGβcf were detected.

There was no significant hLHβcf surge in blood but a substantial hLHβcf surge in urine, indicating that urinary hLHβcf is a product of hLH metabolic processing. The lag time in the appearance of the fragment suggests that it may be a consequence of metabolic processing by the kidney or in some other compartment.

Two assays were used for intact hLH measurements (hLH-1 and hLH-2. The hLH-2 assay was highly specific for the intact hLH molecule, but occasionally produced a weak signal in urinary assays. The hLH-1 assay, although less specific for hLH, (some crossreactivity with hCG, (see Table III) but could detect signals of greater amplitutde, and had better detection when applied to urine specimens. The hLH-2 assay barely detected hLH in the serum of this subject but detected the urinary form as well as the hLH-1 assay, which performed equally well in both serum and urine. This probably reflects metabolic processing of the hLH which affects epitope presentation upon passage of blood to urine.

TABLE III

Assay Specificity and Sensitivity

| Antigen | LH-1 | LH-2 | LHβ | LHβcf | hCGβcf |
|---|---|---|---|---|---|
| hLH, % | 100 | 100 | 29 | 1 | <1 |
| hLHβ, % | <1 | <1 | 100 | 1 | <1 |
| hLHβcf, % | <1 | <1 | <1 | 100 | 2 |
| hCGβcf, % | 2 | <1 | <1 | <1 | 100 |
| hCG, % | 100 | <1 | <1 | <1 | 1 |
| hCGβ, % | 31 | <1 | <1 | 1 | <1 |
| LDD*, fmol/ml | 1 | 1.5 | 1.4 | 1 | 0.6 |

LDD* - least detectable dose

Predicting Onset of Menopause in Perimenopausal Women

A urinary-based assay was used which measures a highly stable metabolite of luteinizing hormone which appears in the urine of all individuals but displays different daily patterns of excretion in relation to the physiological state of the individual. The immunoassays to measure the hLH beta core fragment were developed to the form of the fragment isolated from the pituitary and described above. These assays also measure the form of the molecule that appears in urine (Burger, et al., 1995). The hLHβcf is elevated in normal premenopausal women one or two days after the mid-cycle LH surge (Burger, et al., 1995). The present invention is based on measurements during the follicular phase, usually the ten day period between day one of menses and day 10. Five to ten days of daily, first morning void urine specimens were collected, starting at day one or day two of menses. The amount of hLHβcf concentration in fmole/ml was measured and normalized to creatinine (divided by creatinine concentration in mg/ml). It was determined that premenopausal patterns are easily distinguishable from postmenopausal patterns based on the simple algorithm of area under the peak when at least 5 daily measurement are performed. The average area under the peak for premenopausal women is usually 2–3 standard deviations away from the area under the peak of postmenopausal women (their urine sampling is for 5–10 days, first morning void, at random since they do not have menstrual cycles). The test population of interest is perimenopausal women. The perimenopausal women examined exhibited a hLHβcf profile similar to the profile for premenopausal women or a hLHβcf profile similar to the profile for postmenopausal women. Two perimenopausal women with postmenopausal patterns were known to enter menopause within a year of analysis while two women showing premenopausal patterns did not enter menopause for several years. Several women were followed for a period of years.

Figure 12A:
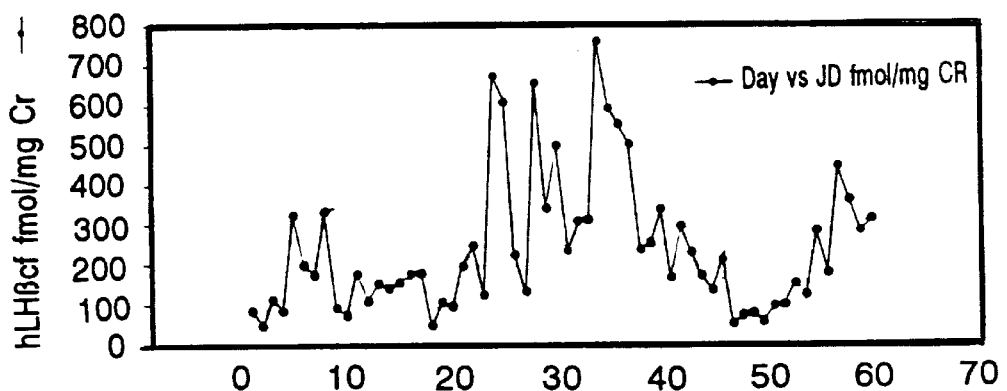
Figure 12B:
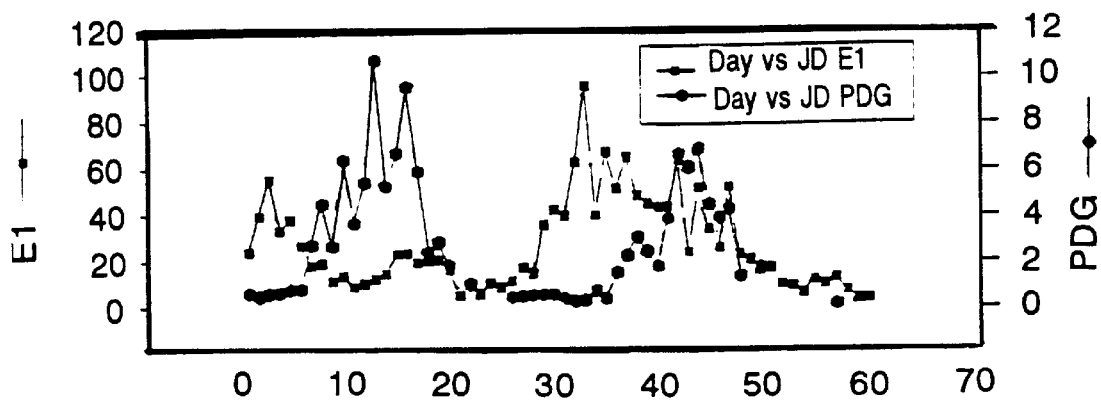
Figure 12C:
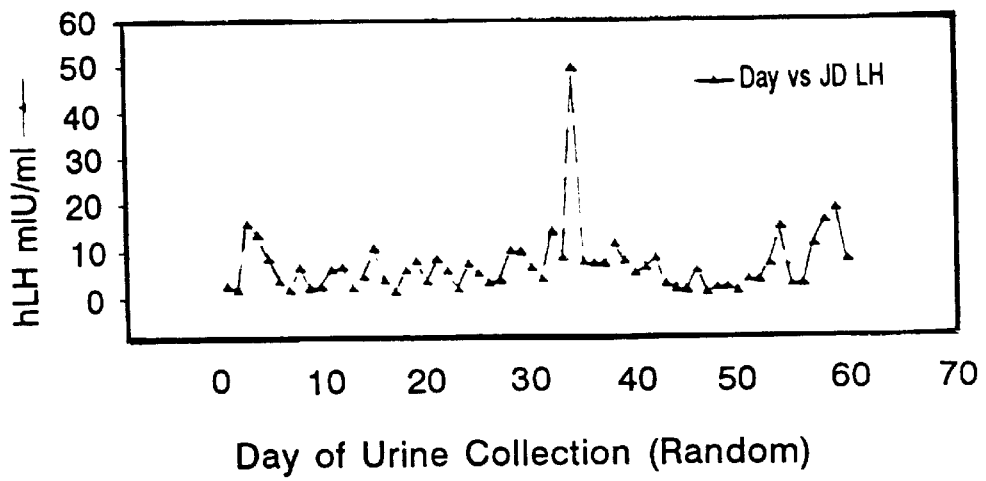
Figure 13A:
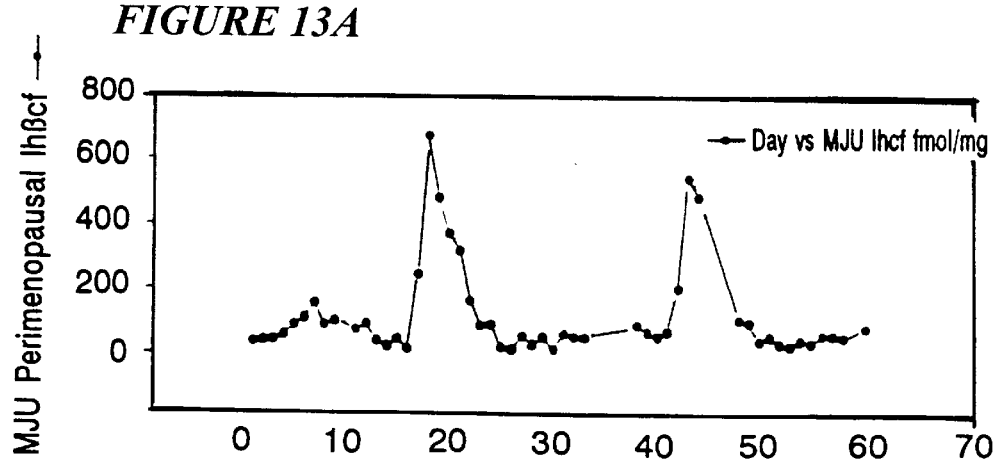
Figure 13B:
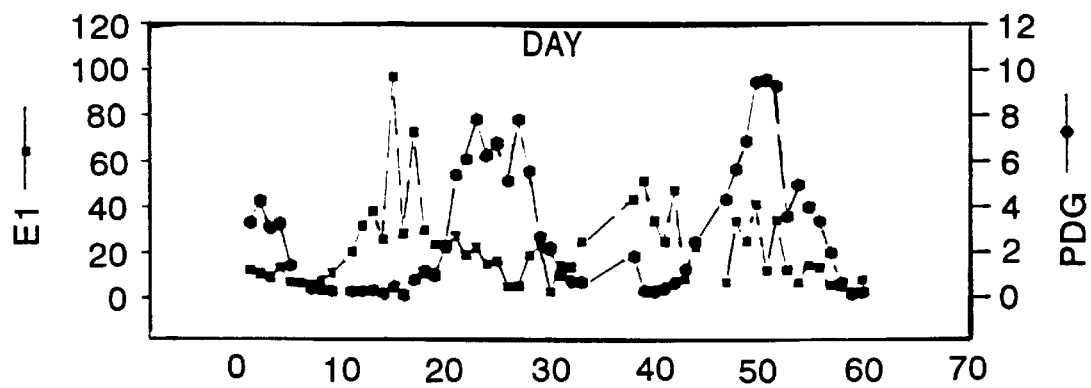
Figure 13C:
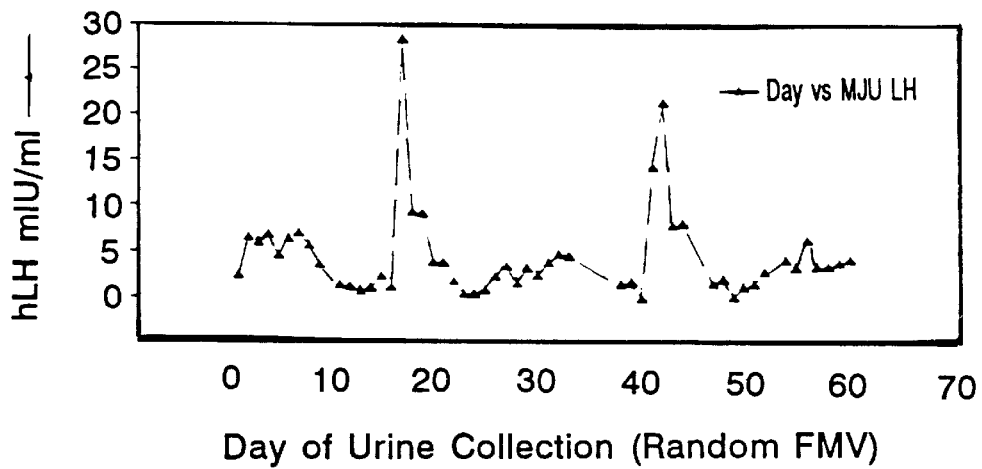

The discrimination of the urinary hLHβcf assay is shown in FIGS. 12–13. These are patients whose urines were collected for 60 days as described above. Both patients were considered to be perimenopausal but both had normal regular cycles. The hLHβcf profile of patient JD is similar to the profile of postmenopausal women while the profile of patient MJU is similar to the premenopausal profile. The assay correctly predicted which patient was closer (exhibited temporal proximity) to menopause since JD, who is now postmenopausal, began to experience irregular cycles within a year of this collection, while MJU only began to experience such irregularities, several years later than JD. JD became postmenopausal within two years.

Predicting Onset of Menopause in Perimenopausal Subjects Using the Area Under the Curve Determined for hLHβcf This experiment takes advantage of the excellent and unique assay described in detail above. The hLHβ subunit, hLHβcf, which is analogous to the hCG beta core fragment in structure and by its similar appearance chiefly in urine. The assay, described in detail above, is a two-site immunoassay to the core fragment molecule which is sensitive to less than 1 fmole/ml in urine. The hLHβcf molecule appears in urine at concentrations much higher than that of hLH 1–2 days after the LH surge in normal premenopausal women. In postmenopausal women, the urinary hLHβcf appears in a pulsatile fashion when consecutive first morning void urines are examined. The amplitude of the fluctuations in postmenopausal individuals are much greater than during the follicular phase of premenopausal individuals forming the basic design of a differentiating assay. Simply summing the area under the peak of graphs plotting day of collection versus hLHβcf in fmoles/mg Creatinine results in sets of numbers that easily distinguish premenopausal from postmenopausal subjects (see Table IV). The Lhβcf urine samples should preferably be at least 2 ml of first morning void urine. The data in Table IV suggests that in the perimenopausal group, the two subjects reflecting areas greater than 3,000 exhibit the greatest temporal proximity to menopause. In other words, of the patients presented in this experiment, the two subjects with areas greater than 3,000 are closest to menopause. Interestingly, they are still experiencing menstrual cycles; one exhibits regular cycling. The subject with an area of 344 is predicted to be temporally distant from menopause.

In this experiment, the perimenopausal group was defined by age. Women 43 years or older were included in this group if they were not already menopausal. Samples were taken from this group during the follicular phase for ten days where day 1 was menses. Samples taken from the menopausal group were from any ten days. Samples were taken from the premenopausal group during the follicular phase for ten days where day 1 was menses.

Interestingly, for these data, the mean Area value for the premenopausal group (n=13) is 237, while the mean value for the postmenopausal group (n=8) is 2267.5, a value nearly 10-fold increased as compared with the premenopausal group. Of the six perimenopausal samples, two Area values (3095 and 3735) exceed the mean Area value for the postmenopausal group; one (344) is less than twice the mean Area value for the premenopausal group; two (614 and 684) are between two and three times the mean Area value for the premenopausal group; and one (849) is between three and four times the mean Area value for the premenopausal group.

Of course, mean Area value is not the only measure or method of analysis of the data, in order to determine similarity of a perimenopausal sample with she premenopausal or postmenopausal groups. Median values are also important, as is regression analysis, pattern analysis and multiplex analyses.

TABLE IV

Area under the Curve for hLHβcf Determined in Samples Taken from Subjects

| Premenopause | Perimenopause | Postmenopause |
|---|---|---|
| 190 | 344 | 2764 |
| 53 | 3095 | 4597 |
| 613 | 684 | 2501 |
| 321 | 614 | 2070 |
| 148 | 849 | 1688 |
| 73 | 3735 | 1168 |
| 251 | | 2181 |
| 378 | | 1171 |
| 6 | | |

TABLE IV-continued

Area under the Curve for hLHβcf Determined in Samples Taken from Subjects

| Premenopause | Perimenopause | Postmenopause |
|---|---|---|
| | 129 | |
| | 603 | |
| | 165 | |
| | 158 | |

Predicting Onset of Menopause in Perimenopausal Subjects Using Subject-described Symptoms and the Area Under the Curve Determined for hLHβcf In this experiment, a questionnaire was used to assess if women had regular cycles and if they thought they had menopause symptoms. In this experiment, the "menopause symptoms" was the subject's subjective answer which may not truly indicate menopause symptoms. Additionally, self-defined menopause symptoms may vary from subject to subject. Further, accurate description of symptoms may result, no from onset of menopause, but from other unidentified causes.

"Cycles" indicate the presence of regular menstrual cycles as described by the subject. This should be an objective measure of a change, though not necessarily an accurate measure of menopausal status for the reasons as described above. Under the heading of "comments" prediction is: (1) far (indicating temporal distance from menopause by Area value); (2) closer (indicating approaching or increasing temporal proximity to menopause by Area value); (3) very close (high temporal proximity to menopause by Area value); and (4) n.c. (indicating a result that is not consistent with the Area value based on a woman's report of symptoms or cycle regularity).

Collection of urine samples from the subjects and measurements of hLHβcf were performed as described above. The data was plotted and area under the curve (Area) was calculated as described above. The data are presented together with the corresponding questionnaire data in Table V below:

TABLE V

Symptoms and Prediction of Onset of Menopause

| Patient | Age | Symptom | Regular Cycle | Area | Comment |
|---|---|---|---|---|---|
| 1 | 46 | no | yes | 737 | closer |
| 2 | 47 | yes | no | 166 | n.c. |
| 3 | 45 | no | yes | 317 | far |
| 4 | 48 | yes | yes | 26 | n.c. |
| 5 | 47 | no | yes | 48 | far |
| 6 | 45 | yes | yes | 1518 | very close |
| 7 | 46 | no | yes | 89 | far |
| 8 | 47 | no | yes | 22 | far |
| 9 | 47 | yes | no | 1518 | very close |
| 10 | 47 | no | yes | 62 | far |
| 11 | 43 | no | yes | 249 | far |
| 12 | 46 | slight | yes | 13 | far |
| 13 | 48 | yes | yes | 752 | close |
| 14 | 50 | no | yes | 866 | close |
| 15 | 43 | no | yes | 101 | far |
| 16 | 43 | yes | no | 849 | close |

Experimental Procedures

Hormones hLH(AFP-4261-A), hLHβ (AFP-3477A), anti-human LH-2 antisera and anti-human LH beta-1 antisera for RIA were provided by the National Hormone and Pituitary Program, NOTCHED. Standards used in the IRMA's were hLH (AFP-8270B), hLHβ (AFP-3282) (all from the same source). HCGβcf were prepared as described by Birken (Birken et al., 1988; Birken et al., 1993).

Iodination of hLHβcf, hLH, hLHβ, purification and iodination of monoclonal antibodies: iodination and separation of monoclonal antibodies and hormones were performed as previously described (Kovalevskaya et al., 1995).

Liquid Phase RIA with $^{125}$I-hLHβcf

The liquid phase radioimmunoassay (RIA) procedure was conducted as follows: 0.1 ml serial dilutions of rabbit antiserum to hLH or hLHβ in phosphate buffered saline (PBS) containing normal rabbit serum (Sigma) and 0.1% sodium azide were added to 0.2 ml $^{125}$I-hLHβcf (30,000 cpm) in PBS with 0.1% BSA (Sigma). The mixture was then incubated overnight at 4° C. Then 0.2 ml sheep anti-rabbit serum was added and this solution was incubated overnight at 4° C. The precipitate containing radioactive hLHβcf was separated by centrifugation and $^{125}$I-content determined by gamma counting (Packard Cobra).

Liquid Phase RIA for hLH and hLHβ

Liquid phase radioimmunoassays (RIA) were conducted as recommended in NHPP instructions. In brief, the binding buffer (buffer A) consisted of PBS supplemented with 0.1% BSA and 0.1% sodium azide. 0.1 ml hLH- or hLHβ-antiserum in PBS 1% normal rabbit serum was also added. Both antisera were prepared in rabbits. This solution was mixed with 0.1 ml of radiolabeled hLH or hLHβ (30,000–40,000 cpm) in buffer A and incubated overnight at 4° C. Then 0.2 ml of a sheep anti-rabbit serum was added and mixture was incubated overnight at 4° C. The precipitate containing bound radioactive hLHβ or hLH was separated by centrifugation and counted in a gamma counter.

IRMA

The methodology for the construction and validation of Immunometric assays has been fully described (O'Connor et al., 1988). Briefly, the specificity of the antibody pairs and their capacity for simultaneous binding to antigen are determined as follows. The analytes tested for potential cross reaction with the hLHβcf monoclonal antibodies included hCGβcf, hLH (AFP 8270B), hLH free β subunit (AFP 3282B), intact hCG (CR 127) and hCG free β subunit (CR129). The range of the β core LH standards was 3.9 to 1000 fmol/ml. The range of cross reactants encompassed 39 to 278000 fmol/ml, depending on the analyte.

The capture antibody was adsorbed onto the wells of microtiter plates by incubating a 20 μg/ml solution of the antibody in coating buffer (0.2 M bicarbonate, pH 9.5) overnight at 4° C. The coating antibody solution was aspirated, the plates were washed (wash solution 0.9% NaCl, 0.05% Tween 20) and blocked with a 1% solution of BSA in PBS. Following incubation with the BSA solution (minimum 3 hours at room temperature) the blocking solution was removed, the wells were again washed with wash solution and 200 ml/well of the appropriate hLHβcf standards or potential cross-reacting molecules were added in phosphate buffer B (0.05M phosphate with 0.1% bovine gamma globulin, 0.15M NaCl and 0.1% NaN$_3$). After overnight incubation at 4° C., the plates were again aspirated and washed. The 200 ml (50,000 cpm–100,000 cpm) of appropriate $^{125}$I-labeled detection antibody (listed with double asterisks in Table 2) was added to the wells which were again incubated for 24 h at 4° C. The tracer was aspirated, the plates washed with water, the individual well placed in glass tubes and the radioactivity determined in a Packard Cobra gamma counter. Doses were determined by interpolation from a smoothed spline transformation of the data points.

In addition to hLHβcf assays, three other assays, described earlier, were used for hLH and hLHβ (Krichevsky et. al., 1994) and for the hCGβcf (Krichevsky et al., 1991).

For the assay of urinary hLH and its metabolic forms, the following antibody pairs were employed: For intact hLH, B406*-A201**; for the hLH free beta subunit, B408*-B409**; and for the hLHβcf B505*-B503**. Prior to assay, the urines are thawed, the pH is adjusted with 1.0M Tris (pH 9.5), 50 µl/ml urine, centrifuged and aliquoted (200 µl/well) into 96 well microtiter plates which had beer previously coated with capture antibody and blocked with BSA. A serially diluted standard curve of the appropriate analyte (intact hLH, hLH free beta subunit or hLHβcf) is added in buffer B to the wells and the plate is incubated overnight at 4° C. The assay is performed from that point identically to that described for antibody characterization.

Antibody Characteristics and Assay Construction

The development and validation of immunometric assays for intact hLH, hLH free beta subunit (Krichevsky et al., 1994), hLHβcf (Kovalevskaya et al., 1995) have been described previously. Briefly, microtiter wells (Immulon II, Dynatech, Chantilly Va.) were coated (200 µl/well) with the appropriate, pretitered solution of the capture antibody in sodium bicarbonate buffer (pH 9.5, 0.2M) by overnight incubation at 40° C. The coating antibody solution was then aspirated, and after blocking the plates with 1% BSA in PBS (overnight 4° C.) the plates washed 5 times with wash solution. Urine specimens, after pH adjustment to approximately 7.5 (1.0M TrisHCl, pH 9, 50 µl/ml), or standards in PBS/0.1% sodium azide/0.1% bovine IgG buffer (Buffer B) and urine controls were then applied to the wells (200 µl/well) and incubated overnight at 4° C. The wells were aspirated, washed five times with wash solution and the appropriate radioiodinated detection antibody (tracer) (50,000 cpm–100,000 cpm in buffer B) was added to the wells (200 µl/well). After an additional overnight incubation at 4° C., the wells were aspirated, the plates washed with deionized water 5 times and the wells were separated and counted in a gamma counter (Packard Cobra). Values for the samples and controls were interpolated from a smoothed spline transformation of the standard curve.

hLH was measured by A407(capture)-B207(tracer) (hLH-1 assay, and B406-A201(hLH-2) (Krichevsky et al., 1994). HLHβ was measured by the B408-B405 assay (Krichevsky et al., 1994) hLHβcf was detected by the B505-B503 assay (Kovalevskaya et al., 1995) and hCGβcf- by the B210-B108 assay (Krichevsky et al., 1991). The sensitivities of assays (least detectable dose, LDD) were calculated as plus two standard deviations (SD) of the standard 'zero'.

For hLHβcf, hCGcf, hLHβ, hLH-1 and hLH-2, intra-assay coefficients of variation were 9%, 4%, 6%, 13% and 10% respectively. interassay coefficients of variation were 9%, 10%, 15%, 21% and 10% for hLHβ, hCGβcf, hLGB, hLH-1 and hLH-2 respectively.

Sample Collection

A) First Morning Void Urine (FMV)

Specimens were collected from normally cycling women, ranging in age from 20 to 42 years. The specimens were stored in the subject's home freezer until delivered to the laboratory.

B) Large Scale Periovulatory Urine Collection

Five subjects were provided with a home ovulation detection kit ("First Response", Carter Wallace, Inc.). Starting with the first day of a positive hLH test signal, daily 24 hour urine collections were made for the succeeding seven days.

C) Cycles Without a Detectable Urinary Intact hLH Signal

Four subjects were selected from a population of women who recruited as normal controls for an investigation of hormone metabolism in premenstrual syndrome subjects. They were between the ages of 18–40 years, and were not pregnant or planning pregnancy. They had regular menstrual cycles and were not using any medication, drug or vitamin known to perturb the menstrual cycle.

D) Male Urine (FMV)

First morning void male urine was collected from 11 subjects between the ages of 18–60.

E) Postmenopausal Urine, Large Volume Collection

Postmenopausal urine was collected from one subject (age 66) by pooling daily collection urine for 40 days. 500 ml of this pool was processed in the same manner as the periovulatory urine pool.

F) Postmenopausal Urine Random Collection

Postmenopausal no urine was collected from 107 subjects enrolled in a study of baseline CA-125 levels in postmenopausal women (Westhoff et al., 1992). The women were recruited from patients at a general medical clinic or a screening mammography appointment. No woman was enrolled who was receiving treatment for any gynecological condition. The subjects ranged in age from 43 to 74 years.

G) Matched Blood and Urine Collection

Matched blood and urine were obtained at the same time from a single person on two occasions, starting with the first day of a positive hLH test signal in urine according to "First Respone" kit and continuing for a total of four days.

Characterization of Urinary hLHβcf

Aliquots of the morning urine from ovulating women were assayed for hLHβcf and collections of the sequential 24 hour urines for days which tested positive were pooled, the pH adjusted to 7.5 using 1.0M Tris HCl and sodium azide (0.1%) was added. One half of this pool was filtered through a 0.45µ membrane (Nalgene, Rochester, N.Y.) and concentrated in an Amicon Cell using a YM-3 membrane (Amicon, Danvers, Mass.). The concentrate was desalted and delpidated on a Sephadex G-15 column (Pharmacia, Piscataway, N.J.) . The eluate was lyophilized and dissolved in 0.1M ammonium bicarbonate buffer, and half of it was gel filtered on double tandem colums of superose 12 (Pharmacia). The entire amount was used in the case of postmenopausal urine.

Column fractions containing hLHβcf immunoreactivity were pooled, lyophilized and then dissolved in 4M guanidine HCl containing 0.1% TFA (pH4). This solution (1.2 ml) was applied to a Vydac C-4 Column (22×4.0 cm). A binary linear gradinet was run. Solution A was 0.1% TFA in water, Solution B was 0.1% TFA in acetonitrile. The flow rate was 1.0 ml/min; gradient 10 min 10% B to 70 min 40% B.

Pituitary hLHβcf was chromatographed under the same conditions as the urinary concentrates.

Urinary Steroid Metabolite Assays

The solid phase microtiter plate-based ELISA's for estrone-3-glucuronide ($E_1$-3-G) and pregnanediol-3-glucuronide (Pd-3-G) were performed with monoclonal antibodies provided by Carter Wallace, Inc. The enzyme-conjugated steroids were provided by Dr. Bill Lasley, and the assays performed according ot the procedure of Munro et al., 1991).

hLHβcf Stability

Midcycle urine, encompassing the hLH urinary metabolite peaks, was collected from five subjects, pooled; pH was adjusted to 7.5 using 1.0M Tris HCl and sodium azide (0.1%) added. Aliquots of the urinary midcycle peak (endogenous urinary hLHβcf) and blank urine (B105 immunoextracted to remove hCG- and hLH-associated urinary metabolites from the urine and thus reduce the background) were stored at −80° C. (control samples). Replicate samples (plus blank) were stored at 4° C., 22° C., and 37° C. for extended time periods. After each time period the samples were returned to the −80° C. freezer. The freeze/thaw specimens were removed from the −80° C. freezer from one to five times/day and thawed either at room temperature or in a water bath at ambient temperature. After the indicated number of freeze/thaw cycles the samples were returned to the −80° C. freezer. At the completion of the stability study, all of the specimens were analyzed in the same assay, in order to avoid interassay variation.

The B105 immunoextracted urine exhibited the same blank value as buffer B.

Statistical Analysis

Data were analyzed using the SigmatStat Program,, version 1.01 (Jandel Corporation, San Rafael, Calif.). One-way analysis of variance with Bonferroni adjustment was used to evaluate stability studies. A comparison with a P-value less than 0.05 was considered significant.

Creatinine

Creatinine determinations were performed in a 96-well microtiter plate format by a procedure adapted from Taussky (Taussky, 1954).

Mass-spectrometry

Mass-spectrometry was performed on a Perceptive Biosystems Voyager DE RP instrument run in linear mode using a matrix of sinapinic acid or DHB.

Sialic Acid and Sulfate Analysis

Sialic acid and sulfate analysis were performed using a Bionex PAD as described (Birken et al., 1996).

EXAMPLE 2

Assessing Hormone Replacement Therapy (HRT)

Clinicians caring for women must make judgements as to he ovarian state or the patient without a clear guide for classification of the patient as pre, peri or postmenopausal. Currently, decisions about estrogen replacement therapy (ERT) are usually made in response to the patient's symptoms (hot flashes, mood disorders, etc.) and chronological age rather than any objective diagnostic tests (Burger, et al., 1995; Burger, 1994a; Burger, 1994b; Hee, et al. 1993). Supplementing estradiol on an unknown background (single tests) may be hazardous to the patient. It may promote a cancer or lead to uterine hyderplasia. Detailed menstrual histories are probably the best current criteria of perimenopause (Burger, 1996;. Burger, 1994b; Metcalf, 1988; Metcalf, et al. 1981b). It is possible that the patient's symptoms are associated with other underlying problems which may be overlooked if they are attributed to early menopause. The high cost and inconvenience of multiple venipunctures for a complete serum estrogen or serum LH profile of a menstrual cycle is prohibitive as a diagnostic route. There are no good markers of the effectiveness of the doses used in estrogen replacement therapy. New markers of the effectiveness of the estrogen replacement therapy will enable proper adjustment of the dosage. Monitoring estrogen therapy would benefit from the discovery of new markers of the effectiveness of the therapy. New markers of menopause are needed since symptoms may be associated with an existing disorder. Symptoms may be associated with another existing disorder. Currently, serum gonadotropins, as well as serum inhibins are markers of limited use. In addition, it is not possible to perform complete LH and FSH serum assays along with urinary steroids for one or two cycles for definitive staging of perimenopause. Further, gametogenic failure precedes estrogen failure by several years and has no good chemical marker.

A test, described herein was devised which is performed using the same daily measurements of hLH beta core fragment as described above for postmenopausal women, specifically, five consecutive days of first morning void urine were collected. Using three patients (specimens that were coded and blinded to the investigators) who received various doses of estrogen, it was determined that one woman exhibited a hLHβcf profile similar to the profile for premenopausal women. One woman exhibited a hLHβcf profile similar to the profile for postmenopausal woman and one was intermediate. This may be interpret ted as meaning that one woman was not setting an adequate estrogen dose, since she remained in a postmenopausal pattern while a second woman was receiving an adequate dose since her hLHβcf profile returned to a premenopausal profile (see FIGS. 14A–14F).

The profile for patient LK (see FIGS. 14A–14B) revealed an area under the curve of 3050 before ERT and 1650 after ERT. The pre-ERT hLHβcf profile is similar to that observed for postmenopausal women. The reduction following treatment indicates that the ERT is somewhat effective. Patient LK exhibits an intermediate pattern after ERT treatment. The profile for paitent VP (see FIGS. 14A–14B) displays an area under the curve of 1350 before ERT and 280 after ERT. This indicates ERT treatment was effective in reducing the amount of hLHβcf to an amount similar to the premenopausal pattern. The profile for patient NP (see FIGS. 14E–14F) revealed an area under the curve of 3200 before ERT and 3260 after ERT. This indicates that the ERT treatment was not effective in altering the amount of hLHβcf. Patient NP continues to exhibit a profile similar to the the postmenopausal profile.

EXAMPLE 3

Assessing Ovarian Function: Polycystic Ovarian Disease

Blood samples were taken from women with polycystic ovarian disease (PCO). hLHβcf was detected in the blood of some of these patients. Furthermore, upon treatment with GnRH a rise in hLHβcf in the blood was measured. This could suggest a release of core fragment from the pituitary although a cross reaction might occur if the hLH concentration is very high. Thus hLHβcf which is not usually measureable in blood, can be detected in plasma after ethanol fractionation.

When PCO patients were treated with single injections of GnRH, Luprolite acetate (1 mg/dose), hLHβcf appeared in the serum. Thus, hLHβcf may have two origins, one directly from the pituitary and a second from peripheral degradation of circulating hLH (see Table VI). Unlike normal controls, some women with PCO have detectable hLH β core fragment in serum.

TABLE VI

| Patients' Serum Concentration of hLHβcf/time after GnRH treatment | | | | | | | | |
|---|---|---|---|---|---|---|---|---|
| pat. # | Urine. | 0 h | 1 h | 2 h | 4 h | 8 h | 12 h | 24 h |
| 001a | 44[a] | 0[b] | ? | 4.6 | 12 | 10 | 14 | 6.8 |
| 001b | 38 | 0 | 4 | 6 | 10 | 12 | 8 | 4.8 |
| 002 | 30/32[c] | 0 | | | | | | |
| 003 | 26/26 | 0 | | | | | | |
| 004 | 260/280 | 0 | 0 | 0 | 8 | 12 | 10 | 0 |
| 006 | 360/320 | 0 | 0 | 0 | 4 | 6 | 4 | 0 |
| 007 | 76/80 | 0 | 0 | 0 | 0 | 0 | 0 | 0 |
| 008 | 50/40 | 0 | | | | | | |
| 009 | 240 | 14 | | | | | | |

[a]fmol/mg creatinine in urine;
[b]fmol/ml in serum c.

These studies are further supported by work with plasmapheresis fluid. The plasma of two postmenopausal patients undergoing this treatment was tested directly and found to exhibit no measurable levels of hLHβcf. However, after ethanol fractionation of the plasma and concentration (10×), high levels of the fragment was observed. In both patients, the fractionated plasma was gel filtered and the hLHβcf immunoreactivity appeared at its expected size of 10,000 M.W. Thus, at least some of this metabolite of hLH circulates in postmenopausal women, perhaps in a form complexed to another protein and only visible after dissociation by organic solvents.

This hLH fragment may circulate in blood, unlike the homologous hCG fragment which exists at very low levels in blood. Chromatographic separation of the pituitary hLHβcf as compared to the urinary molecule with the epitope recognized by our hLHβcf assay indicated that the urinary material eluted in a different position on reverse phase HPLC than did the pituitary form.

EXAMPLE 4

Development of Markers of Menopause

Different Patterns of excretion of the hLH beta core fragment in daily urines of premenopausal as compared to postmenopausal women Objective As part of a long-term effort to develop new objective biochemical assays to stage women during the perimenopausal transition, the patterns of urinary excretion of a metabolite of hLH in premenopausal, perimenopausal and postmenopausal women have been examined. This metabolite is an ideal urinary analyte, highly stable, and easily measured due to its high molar content, and suffering from none of the multiple isoforms and subunit dissociation problems entailed with LH urinary measurements.

Design

The concentration of the hLH beta core fragment in 10 consecutive first morning void urine specimens from premenopausal, perimenopausal and postmenopausal women was measured. Day one of collection was the first day of menses in the cycling women.

Results

Postmenopausal women exhibited a widely fluctuating pattern of fragment excretion which is not correlated with hLH measured in urine considering the 1–2 day delay in metabolite excretion. The postmenopausal group was easily distinguished from premenopausal women based on an area-under-the-curve concentration function. Perimenopausal women displayed intermediate hLH beta core fragment concentrations some being clearly in postmenopausal ranges.

Conclusion

The pattern of excretion and concentrations of the hLH beta core fragment is significantly different between pre-menopausal and postmenopausal women. Perimenopausal women exhibited intermediate changes. Further study of a larger perimenopausal population should permit development of a discriminant function to distinguish those women closest to menopause.

The physical, social and psychological correlates of transition of women into menopause are currently the subject of major research initiatives in woman's health. (1). This initiative is hampered by a lack of biochemical tools that demonstrate the natural history of menopause (2). Although elevated FSH concentrations during menses (day 3 of cycle is sometimes employed to confirm that a woman is close to menopause wide quantitative variations in such measurements among women and even from cycle to cycle or an individual woman limit the utility of such tests (2–7). Consequently, clinical decisions for treatment of perimenopausal women today are based chiefly upon subjective symptoms rather than objective diagnostic tests. The capability to better define objective criteria for stages of the menopausal transition would be an important advance for both the research and clinical settings. Objective tests would improve patient treatment based upon knowledge of where the woman was in the menopausal transition. For example, preventive therapy to avoid osteoporosis may be undertaken earlier if studies showed this problem begins before the final menses.

The use of urinary assays of gonadotropin degradation products as stable, easily measured markers which may more precisely define the phases of perimenopause and possibly predict the time to cessation of menstrual cycles are being explored. These degradation fragments provide the long term stability necessary in a urinary marker molecule, unlike LM itself which may dissociate into its subunits upon prolonged storage and multiple freeze-thaw cycles. In addition, urinary metabolites can be measured in large scale epidemiological studies where it is not possible to collect multiple blood samples.

The hLH beta core fragment (hLHβcf), presumed to be a degradation product of circulating LH, is a highly stable metabolite in urine (8, 9). An analog of this molecule also exists in pituitary tissue, which was in fact the source of the immunogen used to develop a specific and sensitive immunometric assay for its measurement (10). The elevated urinary concentration of this molecule which occurs 1–2 days after the LH surge in normally cycling women as well as in random samples of postmenopausal urine ha been prebiously described (8, 9). The long-term hypothesis which is being tested is that measurement of the concentration of this urinary metabolite of hLH will provide part of an objective assay to determine how far a woman is from menopause. In this report it is demonstrated that its daily pattern in postmenopausal women and the change in its quantitative and qualitative pattern from that of women still experiencing menstrual cycles.

Materials and Methods

Subject Populations Studied

Patient Descriptions

For the three classes of subjects studied, the following criteria of classification were used:

Premenopausal women (10 subjects were studied) were defined as 1) having regular menses with intermenses-intervals between 25 and 45 days and no missed menses or a reported change in flow in the past 12 months and not taking birth control pills. Ages of subjects were 20–42.

Perimenopausal women (18 subjects were studied) were defined as: 1) age 43 or older; 2) a history of regular menstrual cycles 25–35 days in length; 3) non-smoking status; 4) no excessive exercise (>1 hour/day) or aggressive dieting (loss of >1 lb per week) ; 5) no diseases affecting gonadotropin or sex steroid secretion, clearance, or excretion; 6) no hormonal therapy within 3 months of the study; 7) no period or amenorrhea exceeding 3 months in the past year.

Prematurely menopausal women (4 subjects were studied) were less than 40 years of age and met criteria 3–6 above as well as the following additional criteria: 1) at least 90% normal weight for height (Metropolitan Life Tables); 2) normal menarche at age 10–15 with normal menses 25–35 days in length prior to onset of their disorder; 3) serum FSH>40 mIU/ml and estradiol less than 40 pg/ml, 4) at least 1 year of amenorrhea prior to study or no unscheduled menses while on hormone replacement therapy; 5) onset of amenorrhea prior to age 35; 6) 46, XX karyotype on 50 cells; 7) no evidence of autoimmune polyglandular failure, with normal findings of an SMA-18, CBC, negative antithyroglobulin, antimicrosomal, antimitochondrial and antiadrenal antibodies, negative ANA, and a normal 1-hour cortisol response to 250 μg exogenous cosyntropin.

Postmenopausal women (8 subjects were studied) had menopause at age 50 or later and met criteria 2–6 for perimenopausal women, and criteria 1–4 for the prematurely menopausal women.

All participants in this study gave their informed consent prior to entry. The patients contributing samples for 30 or 60 day intervals were studied under protocols approved by the Institutional Review Board at the New Jersey Medical School. These patients have been studied earlier using other assays (11, 12). Additional patients were recruited at Columbia University and at the University of Pennsylvania each of which had their respective studies approved by their own institutional Review Boards.

Assays

The immunometric assay for the hLHβcf has been described in detail elsewhere (13). This assay displays intra and inter assay coefficients of variation of 10%. Earlier studies of stability of the hLHβcf demonstrated that its immunoreactivity remains unchanged after 40 freeze-thaw cycles and two weeks at 37 C. (8). Creatinine content of urine was determined by use of a Beckmann II creatinine analyzer or by using a modification of the method of Taussky (14) and has been previously reported (15).

LH was measured using a fluroimmunometric assay previously validated for use in urine (DELFIA; Pharmacia, Gaithersburg, Md.; (15). Glycerol preservation of the urine was essential for the maintenance of gonadotropin immunoreactivity (16), (15). The interassay coefficient of variation for the LH assay was 18% and the intra-assay CV was 8%. This assay has been demonstrated to be sensitive to 0.1 mIU/mg creatinine (15)

Statistical Analyses and Graphics

Statistical analysis was performed using Graphpad InStat (version 3.00 for Windows, Graphpad software, San Diego, Calif., graphpad.com). Descriptive statistics of each group as well as unpaired t test with Welch correction was performed to test capability to distinguish grouped data using this program. Drawing of graphs as well as calculations of areas under the peaks were performed using Sigmaplot 4.01 for Windows (SPSS, Inc., San Rafael, Calif.)

Results

Premenopausal Pattern of hLHβcf

Figure 15A:
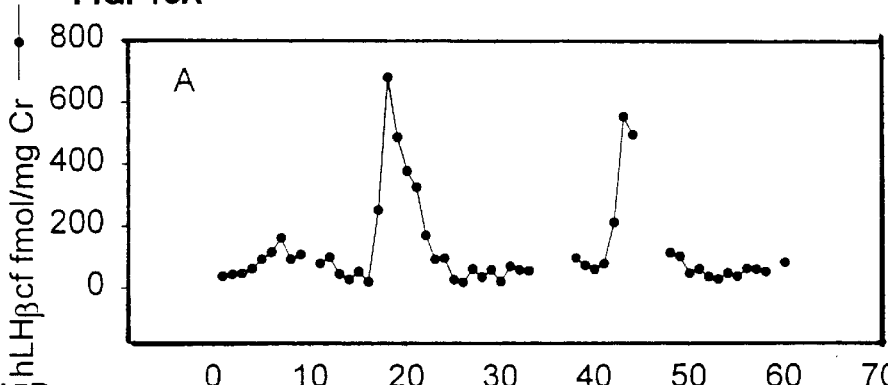
Figure 15B:
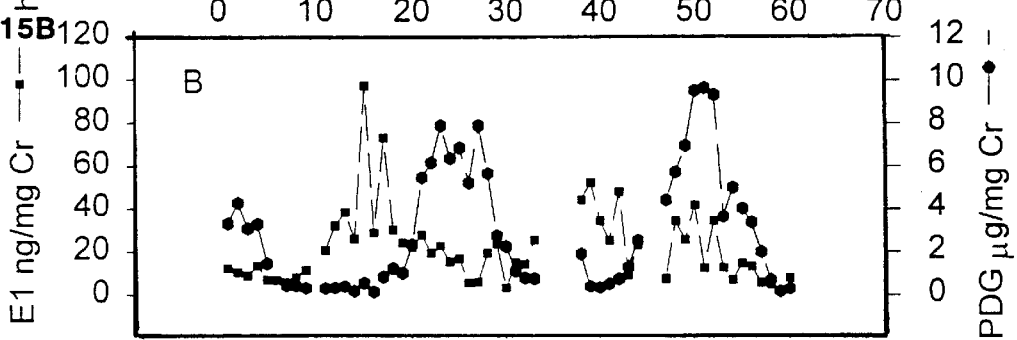
Figure 15C:
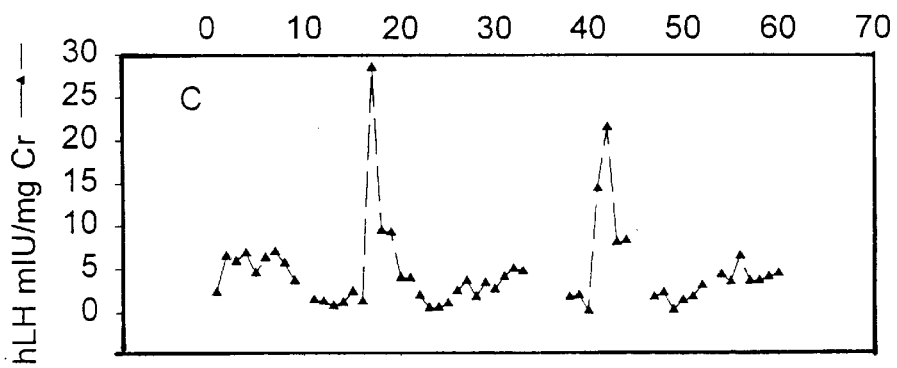
Figure 20A:
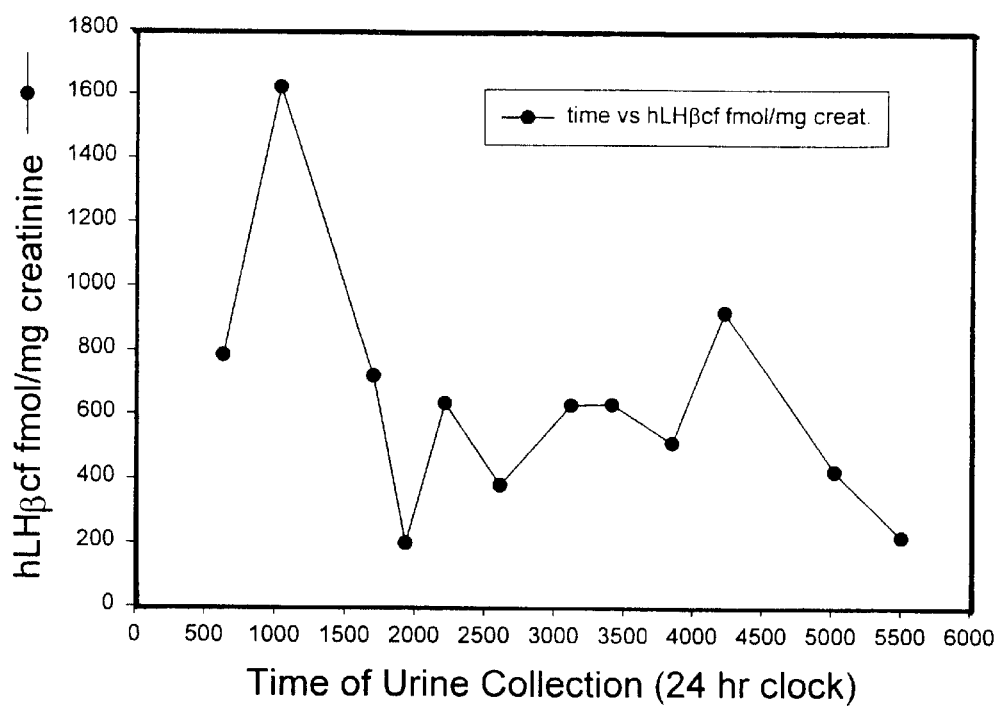
Figure 20B:
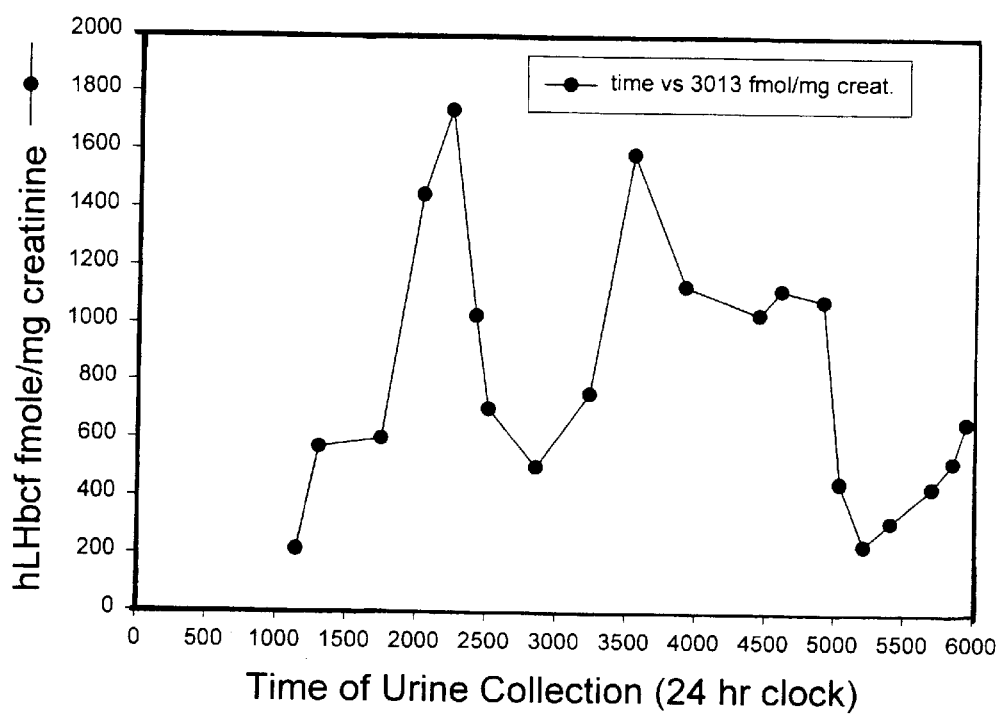
Figure 20C:
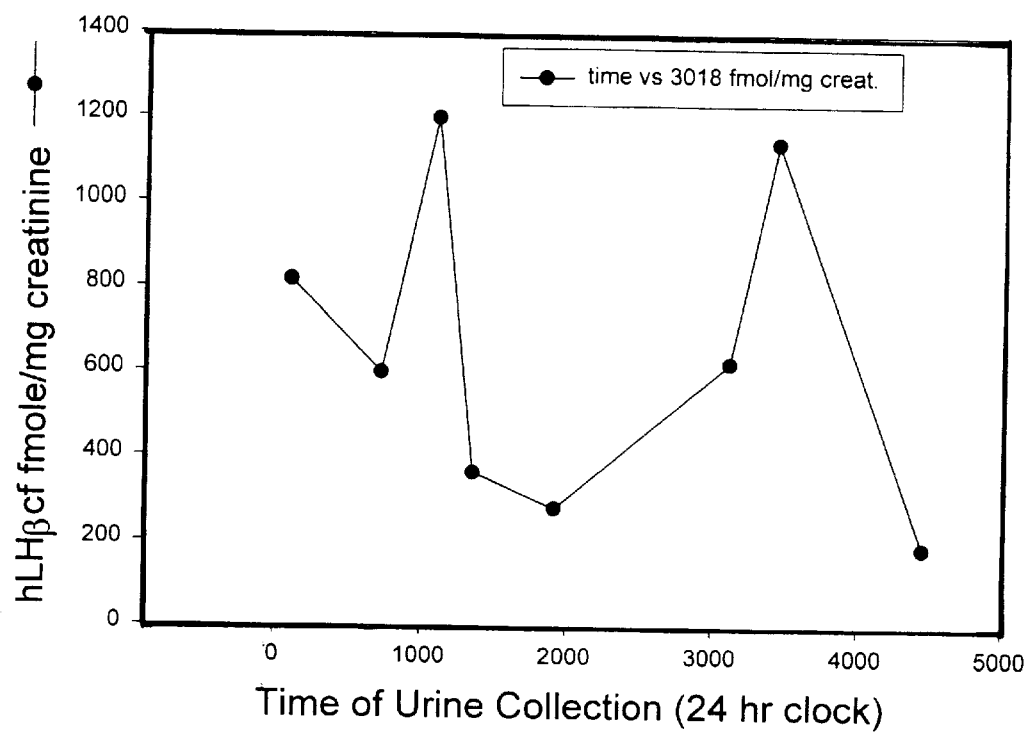
Figure 20D:
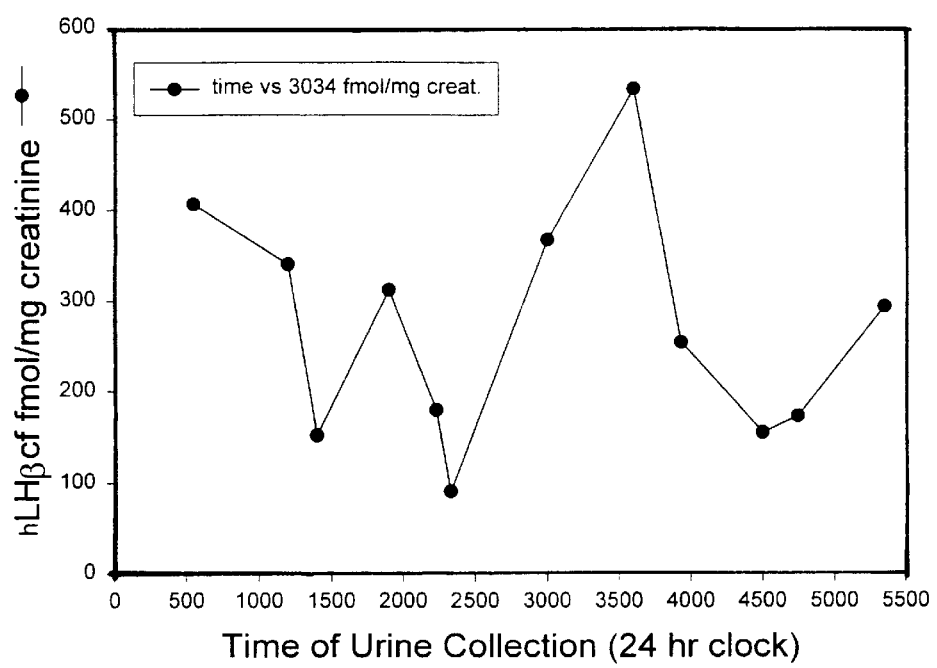
Figure 20E:
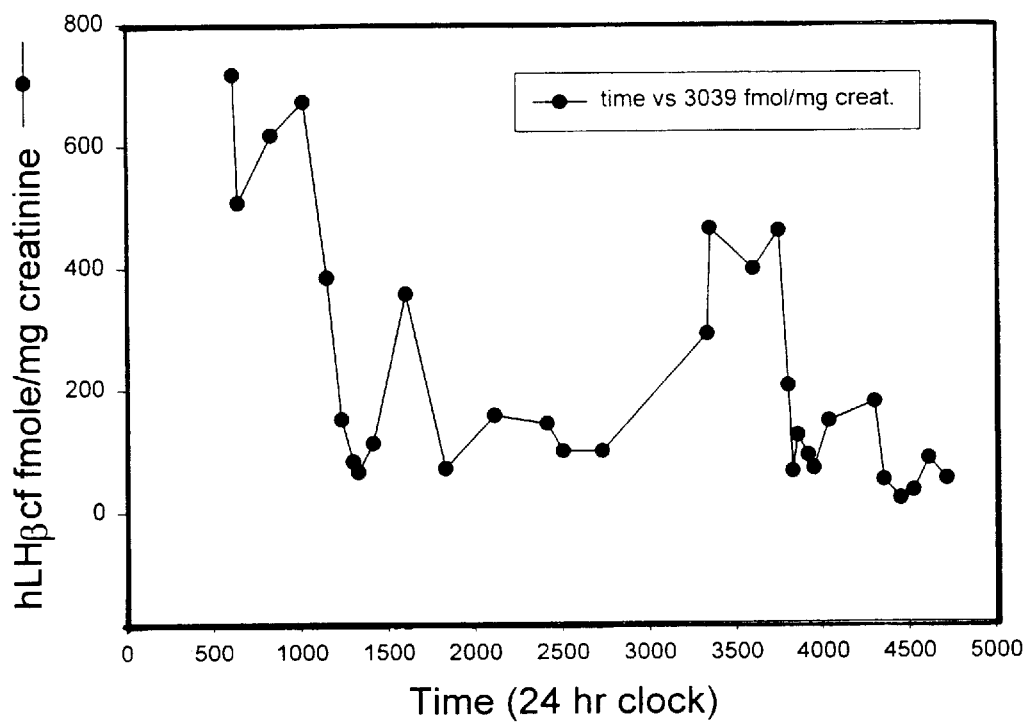

The premenopausal pattern of excretion of this molecule has been detailed in our earlier study (8) and displays mainly one major and broad hLHβcf peak 1–2 days after the LH surge and characterized by a higher molar concentration than hLH in urine. One set of first morning void urine specimens from a woman over 40 but still experiencing regular cycles, still exhibits a typical premenopausal pattern as shown in FIG. 15A. The urinary LH pattern (as measured in the earlier study of Santoro (11)) is shown in FIG. 15C. During the follicular phase, there are relatively small pulses or the hLHβcf but the major hLHβcf peak which follows the LH surge predominates the pattern.

Postmenopausal Pattern of Excretion of the hLHβcf

While hLHβcf was shown as beginning to rise in concentration on the day of the LH surge and to peak 1 or 2 days after the LH surge in urine from women with normal menstrual cycles, the hLHβcf pattern in postmenopausal urine displayed wide daily fluctuations. FIG. 16 (upper panel) shows a typical postmenopausal pattern of hLHβcf measurements in first morning void urine specimens. This 60 day collection shows the large amplitude fluctuations in hLHβcf excretion. The amplitudes range between 100 and 1200 fmoles/mg creatinine and display wide fluctuations with sharp peak amplitudes every few days. These measurements were repeated again after freeze thawing several weeks later and a nearly identical pattern was obtained as shown on FIG. 16A as $1^{st}$ and $2^{nd}$. FIG. 16B shows urinary measurements of hLH. While the LH values also fluctuate in amplitude, the LH peaks do not appear to correspond to hLHβcf peaks, considering the 1–2 day delay in expected fragment appearance after an LH surge (see FIG. 15C). Examination of women who experienced premature ovarian failure and were also considered postmenopausal resulted in a similar profile of large amplitude fluctuations as shown in FIG. 17A. FIG. 17B shows the urinary LH measurements which do not correspond to the LHβcf pattern neither in amplitude nor in the 1–2 day post LH peak delay observed in FIG. 15.

One approach to comparing such pulsatile patterns is to calculate the area under the peaks of these curves that plot day of collection versus concentrations in fmol/mg creatinine. Ten day intervals were selected as a convenient set which could be fairly easily collected by volunteer subjects and stored frozen until samples were brought to the laboratory. When samples are analyzed from women still experiencing regular menstrual cycles, the 10 day interval collection provides a convenient starting point within the cycle and encompasses the follicular phase which most closely corresponds to the postmenopausal state of relatively low circulating steroids. Table 7 shows the area under the peaks of plots of day of collection versus the concentration of hLHβcf expressed as fmol/mg creatinine for regularly cycling women. The mean of the areas of these 10 subjects were 278 with a median area of 169. Using specimens studied earlier by Santoro (11), 60 consecutive early morning urine specimens were available from 6 postmenopausal women. Since there is no starting day for women with no cycles, we examined 10 day area data from each of these women to assess if each 10 day interval for a single woman was comparable to the other 10 day intervals from the same woman. It was found that there was not major variability among the six 10 day intervals in each of the six subjects (see Table 8). Table 8 shows the average areas under the peaks for these six consecutive 10 day collection intervals for each woman. The standard deviations and standard errors of the means are fairly consistent showing that the data is not disparate within each subject. The mean of the areas ranged between 995–3905 with medians between 932–3134 for these postmenopausal subjects. The area data of the postmenopausal subjects differed significantly from the population of normal cycling women by the amplitude and area under the peaks of the daily fluctuations of this fragment. Since postmenopausal women vary in concentration of the hLHβcf and have no cycle start point for collection, as described earlier, in order to determine if any set of randomly collected consecutive postmenopausal areas can be distinguished from premenopausal areas, the worst case scenario was examined. The lowest 10 day area values were chosen from each of the 60 day collections of the 6 postmenopausal women shown in table 8 and compared these areas to the premenopausal areas of table 7 by independent T-test. The mean areas of the lowest 10 day collection for postmenopausal women (1594+/−751) was significantly higher ($T_{(df=5)}$=4.196, p<0.01) than that for premenopausal women (277+/−215). There was no overlap in the two distributions: highest premenopausal area of 700 compared to the lowest postmenopausal area of 727.

TABLE VII

Ten Day Areas Under the Peak from Regularly Cycling Women

| Patient Number | Age | Area |
| --- | --- | --- |
| 137 | 34 | 140 |
| 144 | 23 | 589 |
| 169 | 35 | 307 |
| 100 | 20 | 129 |
| 104 | 37 | 169 |
| 42 | 30 | 700 |
| 75 | 29 | 165 |
| 106 | 41 | 302 |
| 379 | 42 | 6 |
| 110 | 25 | 259 |

Mean: 278; S.E.M. 76; Median: 169

This data represents the areas under the peak of a plot of hLH beta core fmol/mg creatinine versus day of first morning void collections for 10 regularly cycling women.

TABLE VIII

Comparison of Ten Day Areas Segments from each of six 60 Day Daily Collections of First Morning Void Urines of Postmenopausal Women *

| Subject | Mean | S.D. | S.E.M. | Median |
| --- | --- | --- | --- | --- |
| 1 | 995 | 220 | 90 | 932 |
| 2 | 2160 | 588 | 240 | 1987 |
| 3 | 3905 | 583 | 238 | 3934 |
| 4 | 2049 | 524 | 214 | 2125 |
| 5 | 3116 | 530 | 531 | 2878 |
| 6 | 1885 | 406 | 115 | 1042 |

* This data represents areas under 10 day segments (6 segments for each subject) of a 60 day plot of the concentration of the hLHβcf as fmol/mg creatinine in the first morning void urines of 6 postmenopausal women.

Perimenopausal to Postmenopausal Patterns

One overall goal of these studies is to be able to locate a subject within the menopausal transition and develop a discriminant function which would predict the time remaining before cessation of menstrual cycles. FIG. 18 illustrates a woman who was classified as perimenopausal, by criteria described in the methods section, but more closely resembles our postmenopausal women. This subject did experience irregularity of cycles and mild hot flushes. She completed the transition into menopause approximately 3 years after the urine samples were collected. The urinary LH pattern shown in FIG. 18C does not correspond to the hLHβcf pattern in urine (FIG. 18A). Table 9 shows preliminary data on 16 women classified as perimenopausal. The area data is scattered and most exhibit premenopausal areas. The women were asked about regularity of their cycles and queried about any menopausal symptoms. Of the six subjects who reported symptoms which may be associated with menopause, two exhibited high areas (>1500), two exhibited intermediate areas (>750) and two exhibited low areas (<500). Subject 2208 reported the beginning of cycle irregularity a year after an area value of 866 was determined by the 10 day sampling.

TABLE IX

Single 10 day urine collections from first day of menses of perimenopausal women (see methods for definition of perimenopausal group) with hLHβcf areas under the peak and other subject information.

| Patient | Age | Symptom? | Reg. Cycle? | Area |
| --- | --- | --- | --- | --- |
| 23 | 46 | no | Yes | 737 |
| 110 | 47 | yes | No | 166 |
| 126 | 45 | no | Yes | 317 |
| 167 | 48 | yes | Yes | 26 |
| 253 | 47 | no | Yes | 48 |
| 275 | 45 | yes | Yes | 1518 |
| 290 | 46 | no | Yes | 89 |
| 314 | 47 | no | Yes | 22 |
| 0697 | 47 | yes | No | 1518 |
| 2212 | 47 | no | Yes | 62 |
| 2202 | 43 | no | Yes | 249 |
| 2203 | 46 | slight | Yes | 13 |
| 2205 | 48 | yes | Yes | 752 |
| 2208 | 50 | no | Yes | 866 |
| 2209 | 43 | no | Yes | 101 |
| 2222 | 43 | yes | No | 849 |

Mean: 458; S.E.M.: 129; Median: 207

This table presents areas under the curve for plots of the day of first morning void urine collection and the concentration of the hLHβcf as fmol/mg creatinine for 10 days, with day 1 being first day of menses.

Graphic Presentation of Ten Day Urine Collections

As discussed earlier, the paradigm of collection of urine for 10 consecutive days has been applied, day one being the first day of menses, essentially the follicular phase of the cycle. FIG. 19 compares typical 10 day urine collections from a premenopausal women (5A), a perimenopausal woman (5E) and a postmenopausal woman (5C). The most stroking differences are the amplitudes or the hLHβcf spikes. Tables 7–9 display the results of this analysis in terms of comparative areas under the peaks or a variety of samples. While premenopausal and postmenopausal women can be very clearly distinguished, perimenopausal women display a gradation of such changes as would be expected.

Discussion

The transition into the postmenopausal period is characterized by a variety of physical and psychological symptoms which are presumed to be due to the changes in their endocrine milieu consequent to ovarian failure (1, 4, 17–19). The capability to better define the location in the menopausal transition rather than a year or more after cycling has ceased would provide a means of conducting research into the relationship between serious health problems associated with menopause and the temporal aspects of these problems as related to the endocrine state of the woman. For example, it would be possible to determine if bone loss and atherosclerosis problems begin very early or late in the perimenopausal period. If it were possible to objectively assign a patient to a stage then conclusions as to when to initiate hormone therapy would rely more on an objective chemical basis. Some investigators declare that all current biochemical measurements have little predictive value during the menopausal transition due to wide variations in steroid and gonadotropin concentrations (2–5). Although FSH is usually assumed to change in circulating concentration earlier than LH in the perimenopause, a recent report shows age-related increases in LH in women in the early 40s age group (6).

Current data indicates that during some of the perimenopausal period estrogen levels are actually higher than those of young cycling women (11, 2).

A luteinizing hormone metabolite as a possible urinary biochemical marker was focused on first since the immunometric tools have been developed to measure a stable LH metabolite in urine, namely the hLHβcf. This LH degradation product, based on the pituitary analog isolated, is highly homologous to the hCG beta core fragment both in structure and stability (10). It consists of approxmately half of the beta subunit held together by disulfide bridges. The immunochemically detected urinary form of the hLHβcf is stable in urine for at least 2–4 weeks at room temperature if a microbial inhibitor is present and is stable indefinitely in the freezer and to at least 40 freeze-thaw cycles (8). It is a much superior urinary analyte as compared to the heterodimeric gonadotropins, such as hLH itself, which may dissociate upon prolonged storage or multiple freeze thaw cycles. Measurements of urinary LH frequently suffer from problems such as wide variety of isoforms, some of which are not measured by various specific immunoassays, variable molar quantities in urine due to metabolic degradation prior to excretion an instability due to subunit dissociation (8, 13). The hLHβcf as a terminal degradation product suffers from none of these limitations and should be stable for years in frozen specimens.

The widely fluctuating patterns of excretion of the hLHβcf as monitored by first morning void urine sampling differed from our original hypothesis that little variability would be observed in a single subject. Since the hLHβcf is a metabolite of circulating LH, as shown by its appearance as a broad peak after the LH surge (see FIG. 16) (13), it was assumed that postmenopausal women who exhibit a high circulating concentration of LH would exhibit a high plateau of hLHβcf excretion in urine. Essentially, the hypothesis was that the hLHβcf metabolite which takes 24 hr or more to reach its peak concentration in urine following a surge of LH would tend to represent an integration of the many small and large hourly pulses in circulating LH. Circulating LF is presumed to be taken up by a body compartment such as the kidney and released back into the circulation after proteolysis and then rapidly cleared into the urine. Instead of a plateau concentration, sharp peaks of LH core molecules appear in first morning void urines. These peaks are frequently quite independent of LH measured in the urine as shown in FIG. 16. The LH measurements in urine were conducted much earlier by Santoro under conditions in which LH stability during the time of measurement was demonstrated (glycerol added) (11). A number of postmenopausal urine specimens collected at random from 107 subjects had been measured earlier and it had been determined that the mean concentration of hLHβcf was 236 fmol/mg creatinine with a standard error of 35. (8). Although it appeared that there was an expected variability of hLHβcf among women since circulating hLH varies among women, it was assumed that much less variability would be observed in a single individual. The lack of correspondence between the hLHβcf measurement and immunofluorometric LH measurements was striking. The stability of LH core upon prolonged storage is excellent as detailed earlier(8, 13). Therefore, variability in core concentration due to instability is not a problem. At the present time, the reason for the pattern of excretion of hLHβcf is not known. The LH measurements observed in the peri- and postmenopausal women were irregular and erratic and differed greatly from those of the cycling midreproductive aged women. Similar irregular patterns of LH were noted in prematurely menopausal women. In the case of regularly cycling women, the correspondence was quite good in terms of a 1–2 day delay after the large LH surge before appearance of the hLHβcf. The qualitative appearance of the patterns were essentially superimposable.

Several possibilities could explain these findings. Firstly, although good correspondence between serum and urine LH has been clearly demonstrated in cycling and perimenopausal (11, 15), postmenopausal women have not been subjected to the same level of scrutiny. It is possible that in non-cycling peri- and postmenopausal women that LH secretion is altered in a way that leads to a different ability to detect it in urine. Some evidence of this phenomenon using the DELFIA immunofluorometric assay has been previously published (11). Sometimes LH is not detected at all in urine samples due either to an isoform which is non-reactive in the immunoassay or due to complete dissociation into subunits (8). Failure to obtain corresponding 'peaks and valleys' of hLHβcf suggest that differential clearance or processing of hLHβcf occurs relative to the intact molecule which appears to be the moiety measured by the immunometric (DELFIA) assay (15). Furthermore, positional (related to recumbency) or circadian effects may alter the pattern of LH that is secreted in the high-output states of overt ovarian failure. It appears as if the hLHβcf metabolite is sequestered in a tissue compartment and released into the circulation in sharp bursts which are rapidly cleared into the urine. The pulses of hLHβcf in the urine of postmenopausal women are much larger in amplitude than the pulses of LH measured by rapid sampling techniques (every 10 minutes) in the blood of postmenopausal women (20). At any rate, hLHβcf assay appeared to have greater sensitivity to detect these erratic patterns of LH and may therefore prove to be predictive of the onset of the menopausal transition.

The hLHβcf excretory pattern of postmenopausal women is easily distinguished from premenopausal women. Comparing the area under the peak for 10 day intervals, it was shown that studies of 60 day first morning daily collections of postmenopausal women's urine were fairly consistent with each other. The lowest area under the peak segments of such 10 day sampling of postmenopausal women with similar areas of premenopausal women were then compared and showed that the two groups can be very easily distinguished by such criteria. The perimenopausal group will require a larger population base in order to develop a discriminant function.

Since the hLHβcf used to produce the monoclonal antibodies that constitute our immunometric measurement system were generated to molecules purified from the pituitary and not from the urine, it is clear that these molecules exist in the pituitary and may be secreted by the pituitary. This would imply two possible origins of the hLHβcf in urine, perhaps the major component deriving from degradation of LH as it passes through the kidney, similar to the origin of the hCG beta core fragment from circulating hCG, or directly from the pituitary. If secreted directly from the pituitary, its clearance rate would be quite rapid (minutes) since the core is relatively small (10,000 Da). The hCG beta core is cleared quickly into the urine (21). It has been shown that the pituitary form of the hLHβcf is somewhat different than the urinary form based on different elution positions on reverse phase HPLC (13). However, at the present time, there is no facile means of distinguishing the presence of some hLHβcf of pituitary origin from that of urinary origin. Recent reports support a partial placental origin of the hCGβcf directly from placental tissue (22). It is conceivable that some pituitary hLHβcf may be secreted and modified in transit through the kidney to result in the different form observed on HPLC. Alternatively, LH can be accumulated in a tissue compartment and released in spurts after proteolysis to the hLHβcf.

In conclusion, the evaluation cf measurement of a stable urinary gonadotropin metabolite, hLHβcf, as a marker of the transition to menopause has commenced. Preliminary data in this report demonstrate that postmenopausal women have much higher concentrations of this hLH metabolite than do premenopausal women. The metabolite also appears to be released from its tissue of origin in a broad, pulsatile manner which may also be indicative of proximity to menopause. Application of an area-under-the-peak algorithm indicated that postmenopausal patterns of this metabolite were easily discriminated from those of premenopausal women. A larger study is being undertaken to evaluate the application of this urinary marker to derive a discriminant function to distinguish women early in perimenopause from those later in the transition.

EXAMPLE 5

A new sampling strategy was explored. The paradigm previously detailed was a collection of 10 first morning urine specimens during the follicular phase with day 1 being the first day of menses. The new collection strategy undergoing testing is to collect spot urine specimens, that is samples of urine whenever the woman urinates during a 1–2 day time frame. The woman is asked to record date and time of urination. We found that such collections exhibit similar pulsatile fluctuations to those seen during the 10 day collections. This opens the possibility that testing can be done within a single day by just collecting urinations during that day. This would make the sampling protocol simpler for women being tested. It may be that 2 days are needed but this has not yet been determined. Some of the 2 day spot urine patterns of the hLH beta core fragment are shown graphically.

EXAMPLE 6

The Expression of the Urinary Forms of hLH Beta Fragment in Various Populations as Assessed by a Specific Immunoradiometric Assay Abstract Human gonadotropins undergo metabolic transformations which result in the presence of several smaller, structurally and immunologically related forms in the urine. For hLH, a beta core fragment (hLHbcf) has been isolated from the pituitary and characterized. The corresponding urinary fragment is inferred from mass spectral and immunochemical analysis of chromatographically separated urinary forms. Physico-chemical characteristics, primarily mass spectral and chromatographic, indicate that the pituitary and urinary forms of hLHbcf have a different structure, probably in the carbohydrate moieties. This communication characterizes the expression of hLHbcf in the urine of both reproductive and postreproductive age women and in men, employing assays highly specific for the pituitary form of the fragment. It was found that hLHbcf is the predominant hLH associated molecular form in the urine during periovulatory period, peaking over 1–3 days later then intact hLH and reaching a concentration of about 600 fmol/mg creatinine, seven fold higher than either hLH or hLH free beta subunit. Corresponding levels of hCGbcf were less then 1% that of HLHbcf. HLHbcf cross-reaction with some hLH or hLHb monoclonal antibodies may well interfere with the accurate estimation of the day of the hLH surge when urinary tests are utilized.

Introduction

Metabolic processing of circulating gonadotropins includes renal excretion, presumably preceeded by some form of partial hormone degradation within the kidney as well as in other tissue compartments. A major form of urinary hCG-associated immunoreactivity as an epitope on a molecule smaller than heterodimeric hCG (Schroeder and Halter, 1983; O'Connor et al., 1994; Birken et al., 1996a). This molecule has been identified as an hCG beta core fragment (Birken et al., 1988; Blithe et at., 1988). It has been shown that in normal pregnancy, the core fragment constitutes a major mole fraction of urinary hCG excretion (Kato and Braunstein, 1988). Accumulating evidence has suggested that a similar hLH fragment appears in the urine. Iles (Iles et al., 1992) and Neven (Neven et al., 1993) demonstrated that, using polyclonal antisera raised against hCG beta core fragment (hCGbcf), immunoreactive beta core like activity could be detected in both postmenopausal women and in the periovulatory period of the normal menstrual cycle. Both of these investigative teams ascribed this immunoreactivity to an hLHbcf, which their polyclonal hCGbcf antibodies were detecting as a consequence of cross-reaction. Recently Birken (Birken et al., 1993) described the isolation and structural determination of an hLHbcf from human pituitaries. Employing this material as an immunogen, Kovalevskaya (Kovalevskaya et al., 1995) developed a panel of monoclonal antibodies with which specific immunometric assays for this molecule were developed. Although the urinary hLHbcf has not yet been isolated, and appears to have a somewhat different structure than its pituitary counterpart, its essential identity with pituitary hLHbcf in based on the observations that the urinary molecule shares at least two epitopes with the pituitary form; it has a similar size on gel chromatography and it appears in urine 1–3 days subsequent to the intact hLH surge, suggesting that it originated from the intact hLH molecule or its free beta subunit. This is the first communication in which a specific immunometric assay is employed to report the levels of expression of this new hLH molecular form in men and women at different stages of their reproductive history.

Since urinary analyte stability, particularly for hLH and hFSH, has been reported to be a problem (Livesey et at., 1980; Livesey et al., 1983; Saketos et al. 1994), we also report on our studies concerning the thermal and freeze/thaw cycle stability of urinary hLHbcf.

Materials and Methods

Hormones

HLH (AFP-4261-A), hLHb (AFP-3477A), anti-human LH-2 antisera and anti-human LH beta-1 antisera for RIA were kindly provided by the National Hormone and Pituitary Program, NIDDKD. Standards used in the IRMA's were hLH (AFP-8270B), hLHb (AFP-3282) (all from the same source). HCGbcf and hLHbcf were prepared as described by Birken (Birken et al., 1988; Birken et al., 1993).

Iodination of hLHβcf, hLH, hLHb, and purification and iodination of monoclonal antibodies Iodination and separation of monoclonal antibodies and hormones were performed as previously described (Kovalevskaya et al., 1995).

Liquid Phase RIA with $^{125}$I-hLHbcf

The liquid phase RIA procedure was conducted as follows: 0.1 ml serial dilutions of rabbit antiserum to hLH or hLHb in PBS containing 1% normal rabbit serum (Sigma) and 0.1% sodium azide were added to 0.2 ml $^{125}$I-hLHbcf (30 000 cpm) in PBS with 0.1% BSA (Sigma). The mixture was then incubated overnight at 4° C. Then 0.2 ml sheep anti-rabbit serum was added and this solution was incubated overnight at 4° C. The precipitate containing bound radioactive hLHβcf was separated by centrifugation and $^{125}$I-content determined by gamma counting (Packard Cobra).

Liquid Phase RIA for hLH and hLHb

Liquid phase radioimmunoassays were conducted as recommended in NHPP instructions. In brief, the binding buffer (buffer A) consisted of PES supplemented with 0.1% BSA and 0.1% sodium, azide. A 0.1 ml solution containing standards or unknown sample was added to 0.1 ml buffer A and 0.1 ml hLH- or hLHb-antiserum (both antisera were prepared in rabbits) in PBS containing 1% normal rabbit serum was also added. This solution was mixed with 0.1 ml of radiolabeled hLH or hLHb (30 000–40 000 cpm) in buffer A and incubated overnight at 4° C. Then 0.2 ml of a sheep anti-rabbit serum was added and mixture was incubated overnight at 4° C. The precipitate containing bound radioactive hLHβ or hLH was separated by centrifugation and counted in a gamma counter.

Antibody Characteristics and Assay Construction

The development and validation of immunometric assays for intact hLH, hLH free beta subunit (Krichevsky et al., 1994), hCGbcf (Krichevsky et al., 1991) and hLHbcf (Kovalevskaya et al., 1995) have been described previously.

Briefly, microtiter wells (Immulon II, Dynatech, Chantilly Va.) were coated (200 ml/well) with the appropriate, pretitered solution of the capture antibody in sodium bicarbonate buffer (pH 9.5, 0.2M) by overnight incubation at 4° C. The coating antibody solution was then aspirated, and after blocking the plates with 1% BSA in PBS (overnight 4° C.) the plates were washed 5 times with deionized water. Urine specimens, after pH adjustment to approximately 7.5 (1.0M Tris HCl, pH 9, 50 ml/ml), or standards in PBS/0.1% sodium azide/0.1% bovine IgG buffer (Buffer B) and urine controls were then applied to the wells (200 ml/well) and incubated overnight at 4° C. The wells were aspirated, washed five times with deionized water and the appropriate radioiodinated detection antibody (tracer) was added to the wells (200 ml/well). After an additional overnight incubation at 4° C., the tracer was aspirated, the plates were washed with deionized water 5 times and the wells were separated and counted in a gamma counter (Packard Cobra). Values for the samples and controls were interpolated from a smoothed spline transformation of the standard curve.

HLH was measured by A407(capture)-B207(tracer) (hLH-1 assay) and B406-A201(hLH-2) (Krichevsky et al., 1994). HLHb was measured by the B408-B409 assay (Krichevsky et al., 1994), hLHbcf was detected by the B505-B503 assay (Kovalevskaya et al., 1995) and hCGbcf by the B210-B108 assay (Krichevsky et al., 1991). The sensitivity and specificity of these assays are detailed in Table 3. The sensitivities of assays (least detectable dose, LDD) were calculated as plus two standard deviations (SD) of the standard 'zero' (i.e. NSB).

For hLHbcf, hCGbcf, hLHb, hLH-1 and hLH-2, intra-assay coefficients of variation were 9%, 4%, 6%, 13% and 10% respectively. Interassay coefficients of variation were 9%, 10%, 15%, 21% and 10% for hLHbcf, hCGbcf, hLHb, hLH-1 and hLH-2 respectively.

Sample Collection

A) First Morning Void Urine

These specimens were collected from 15 normally cycling women, ranging in age from 20 to 42 years. The specimens were stored in the subject's home freezer until delivered to the laboratory.

B) Large Scale Periovulatory Urine Collection

Five subjects were provided with a home ovulation detection kit ("First Response", Carter Wallace, Inc). Starting with the first day of a positive hLH test signal, daily 24 hour urine collections were made for the succeeding seven days.

C) cycles Without a Detectable Urinary Intact hLH Signal

Four subjects were selected from a population so women who were recruited as normal controls for an investigation of hormone metabolism in premenstrual syndrome subjects. They were between the ages of 18–40 years, and were not pregnant or planning pregnancy. They had regular menstrual cycles and were not using any medication, drug or vitamin known to perturb the menstrual cycle.

D) Male Urine

First morning void male urine was collected from 11 subjects between the ages of 18–60.

E) Postmenopausal Urine, Large Volume Collection

Postmenopausal urine was collected from one subject (age 66) by pooling daily collection urine for 40 days. 500 ml of this pool was processed in the same manner as the periovulatory urine pool.

F) Postmenopausal Urine Random Collection

Postmenopausal urine was collected from 107 subjects enrolled in a study of baseline CA-125 levels in postmenopausal women (Westhoff et al., 1992). The women were recruited from patients at a general medical clinic or a screening mammography appointment. No woman was enrolled who was receiving treatment for any gynecological condition. They ranged in age from 43 to 74 years.

G) Matched Blood and Urine Collection

Matched blood and urine were obtained at the same time from a single person on two occasions, starting with the first day of a positive hLH test signal in urine according to "First Response" kit and continuing for a total of 4 days.

All collection protocols were approved by the CPMC Institutional Review Board.

Characterization of Urinary hLHbcf

Aliquots of the morning urine from ovulating women were assayed for hLHbcf and collections of the sequential 24 hour urines for days which tested positive were cooled, the pH adjusted to 7.5 using 1.0M Tris HCl and sodium azide (0.1%) was added. One half liter of this pool was filtered through in 0.45 m membrane (Nalgene, Rochester, N.Y.) and concentrated in an Amicon Cell using a YM-3 membrane (Amicon, Danvers, Mass.). The concentrate was desalted and delipidated on a Sephadex G-15 column (40× 2.5 cm, Pharmacia, Piscataway, N.J.). The eluate was lyophilized and dissolved in 0.1M ammonium bicarbonate buffer, and half of it was gel filtered on double tandem columns of Superose 12 (30×1 cm, Pharmacia). The entire amount has been used in the case of postmenopausal urine. Those column fractions containing hLHbcf immunoreactivity were pooled, lyophilized and then dissolved in 4M guanidine HCl containing 0.1% TFA (pH 4). This solution (1.2 ml) was applied to a Vydac C-4 Column (22×4.6 cm). A binary linear gradient was run. Solution A was 0.1% TFA in water, Solution B was 0.1% TFA in acetonitrile. Flow rate 1.0 ml/min; gradient 10 min 10% B to 70 min 40% B. Pituitary hLHbcf was chromatographed under the same conditions as the urinary concentrates.

Urinary Steroid Metabolite Assays

The solid phase microtiter plate-based ELISA's for estrone-3-glucuronide ($E_1$-3-G) and pregnanediol-3-glucuronide (Pd-3-G) were performed with monoclonal antibodies kindly provided by Carter Wallace, Inc. The enzyme-conjugated steroids were provided by Dr. Bill Lasley, and the assays performed according to the procedure of Munro (Munro et al., 1991).

hLHbcf Stability

Midcycle urine, encompassing the hLH urinary metabolite peaks, was collected from five subjects, pooled; pH was adjusted to 7.5 using 1.0M Tris HCl and sodium azide (0.1%) added. Aliquots of the urinary midcycle peak (endogenous urinary hLHbcf) and blank urine (B105 immunoextracted to remove hCG- and hLH-associated urinary metabolites from the urine and thus reduce the background) were stored at −80° C. (control samples). Replicate samples (plus blank) were stored at 4° C., 22° C., and 37° C. for extended time periods. After each time period the samples were returned to the −80° C. freezer. The freeze/thaw specimens were removed from the −80° C. freezer from one to five times/day and thawed either at room temperature or in a water bath at ambient temperature. After the indicated number of freeze/thaw cycles the samples were returned to the −80° C. freezer. At the completion of the stability study, all of the specimens were analysed in the same assay, in order to avoid interassay variation.

The B105 immunoextracted urine exhibited the same blank value as buffer B.

Statistical Analysis

Data were analyzed using the SigmaStat Program, version 1.01 (Jandel Corporation, San Rafael, Calif.). One-way analysis of variance with Bonferroni adjustment was used to evaluate stability studies. A comparison with a P-value less than 0.05 was considered significant.

Creatinine

Creatinine determinations were performed in a 96-well microtiter plate format by a procedure adapted from Taussky (Taussky, 1954).

Mass Spectrometry

Mass spectrometry was performed on a Perceptive Biosystems Voyager DE RP instrument run in linear mode using a matrix of sinapinic acid or DHB.

Sialic Acid and Sulfate Analysis

Sialic acid and sulfate analysis were performed using a Bionex PAD as described (Birken et al., 1996b)

Results

HLHbcf and hCGbcf in Periovulatory Urine

In the cohort of women studied (n=15), a peak of hLHbcf was observed to occur over a 3–4 day period, commencing on the day of hLH surge and reaching a maximum value of 560 (SE119) fmol/mg creatinine at 1–3 days post urinary intact hLH peak (FIG. 9). A peak of hLH free beta subunit (hLHb) was observed to occur simultaneously with that of the intact molecule. Although the levels of hLHb approximated those of the intact hormone, the levels of hLHbcf were several fold higher (FIG. 9).

A surge of hCGbcf immunoreactivity peaked two days post intact hLH, generally coincident with the peak of hLHbcf but at levels which were 1:100 of those for hLHbcf. Since the cross-reaction of the hCGbcf immunoassay with the pituitary hLHbcf was determined to be 1–2%, and since the true cross-reactivity with the urinary form is unknown, it may be that the total signal detected in the hCGbcf assay is in fact due to cross-reaction with hLHbcf (Birken et al. 1996a).

The urinary hLH surge was detected by A407-B207 (hLH-1) antibody configuration. Additionally, eight of the 15 cycles were rerun in a different antibody configuration assay B406-A201 (hLH-2). These assays were constructed using monoclonal antibodies to different hLH epitopes (Table 3). Both hLH-1 and hLH-2 assays gave the same day of hLH surge, but the concentration of hLH in the two assays differed significantly (paired t-test, P=0.0005).

This observation further illustrates that the levels of hormone detected immunologically in urine reflect the differential conservation (or stability) of hLH epitopes excreted into urine and confirm the cautionary observations of others that monoclonal antibodies may in fact be too specific to provide an accurate estimation of the level of all forms of hLH in either blood or urine (Pettersson et al., 1991; Pettersson et al., 1992; Martin-Du-Pan et al., 1994; Costa-gliola et al., 1994; Mitchell et al., 1995; Barbe et al., 1995; Pettersson and Soderholm, 1991).

All cycles were characterized by irregular pulsations of hLHbcf. The basal level of hLHbcf in 10 patients during first 10 days of the follicular phase (100 samples) was 32 (SE 4) fmol/mg creatinine, with a wide range of concentrations, reflecting the spikes or hLHbcf occurring before the periovulatory surge of hLHbcf (FIG. 10).

HLHbcf in Subjects Without a Detectable Rise in Periovulatory Intact hLH

Examination of daily first morning urines from four women in which the hLH periovulatory surge was minimal or undetectable, as measured by either of our intact hLH assays, indicated that ovulation occurred as judged by the inversion of the urinary estrogen/progesterone metabolite ratio (Baird et al., 1991). Data from two of the four women are presented in FIGS. 7a–7d. Evidence from the urinary steroids that ovulation occured suggested that one or more of the following occured. The intact hormone may have been completely cleared by an alternative pathway. The alternative pathway would be clearance through the liver, which has receptors for asialoglycoproteins and sulfated glycoproteins (Flete et al., 1991; Weiss and Ashwell, 1989; Steer and Ashwell, 1986; Kawasaki and Ashwell, 1976). The intact hormone may have dissociated completely into subunits or been totally degraded into fragments prior to excretion, as is the case with hCG, i.e. administration of the intact hCG molecule to either men or non-pregnant women results in the appearence of hCGbcf in the urine (Nisula et al., 1989). Finally, the antibodies used in these measurements, which were raised to the pituitary form of hLH, may have failed to recognize the urinary isoform of hLH present in the sample. That the lack of evidence for intact hLH was not a consequence of these subjects producing an isoform of hLH which was not recognized by these antibody combinations was supported by the fact that a clear hLH peak was found in other cycles tested from these subjects (data not presented).

These cycles however were characterized by the presence of a periovulatory peak of hLHb and a substantial secretion of hLHbcf within the expected time interval (FIGS. 7a–7d).

HLHbcf Expression in the Urine of Postmenopausal Women

The levels of intact hLH, hLHb, hLHbcf, and hCGbcf were evaluated in a total of 107 healthy postmenopausal women (FIG. 8). The mean concentration of hLHbcf for the 107 postmenopausal women was 236 (SE 35) fmol/mg creatinine.

HLHbcf Expression in the Urine of Males

Urines collected from eleven normal males (age 20–60) yield a value of 41 (SE 13) fmol/mg creatinine.

Comparison of hLH or hLHb Measurement in Urine Using IRMA and RIA

HLH and hLHb were measured in urine using IRMA's incorporating specific monoclonal antibodies (FIG. 9A) and by RIA (FIG. 9B), using polyclonal antisera directed against either intact hLH or hLHb, supplied by the National Hormone and Pituitary Program, NIDDKD. The RIA reagents were designed for serum assays and usually clearly provide a single day pre-ovulatory elevation of both hLH and occasionally hLHb in blood.

When these same reagents are employed for hLH or hLHb measurement in urine however, a broad peak for either hormone was obtained. These observations can be explained by the presence of hLHbcf in the urine (FIG. 9A). If panels A and B are compared, it is apparent that the day of maximum hLHb by IRMA is different from the RIA value, probably due to the greater cross-reactivity of the hLHb polyclonal antiserum to hLHbcf.

The cross-reactivities of the polyclonal antisera to hLHb and to intact hLH with hLHbcf were further evaluated in an RIA using hLHbcf labeled with I-125 (FIG. 10). Both polyclonal antisera clearly recognized hLHbcf. The pituitary form of hLHbcf was used in this experiment but a similar reactivity pattern should also be observed with the urinary variant of this molecule, since the monoclonal antibodies developed to the pituitary material all appear to share epitopes present on the urinary molecule.

HLHbcf in Blood and Urine

A comparison of the concentration of hLHbcf in blood and urine was undertaken by collecting paired samples begining on the first day of the hLH surge in urine (detected by "First Response" kit) and continuing for three subsequent days in a single subject. The collection was repeated during a subsequent cycle. FIG. 11 illustrates corresponding values in blood and urine for hLH, hLHb, and hLHbcf. The hLH-1 assay provided a significantly stronger signal in serum than did the hLH-2 assay. The hLHb signal appears synchronously with the intact peak in this subject in urine. However, the hLHbcf surge commences a day later and is detected only in the urine.

HPLC Analysis of hLHbcf of Pituitary and Urinary Origins

Figure 2:
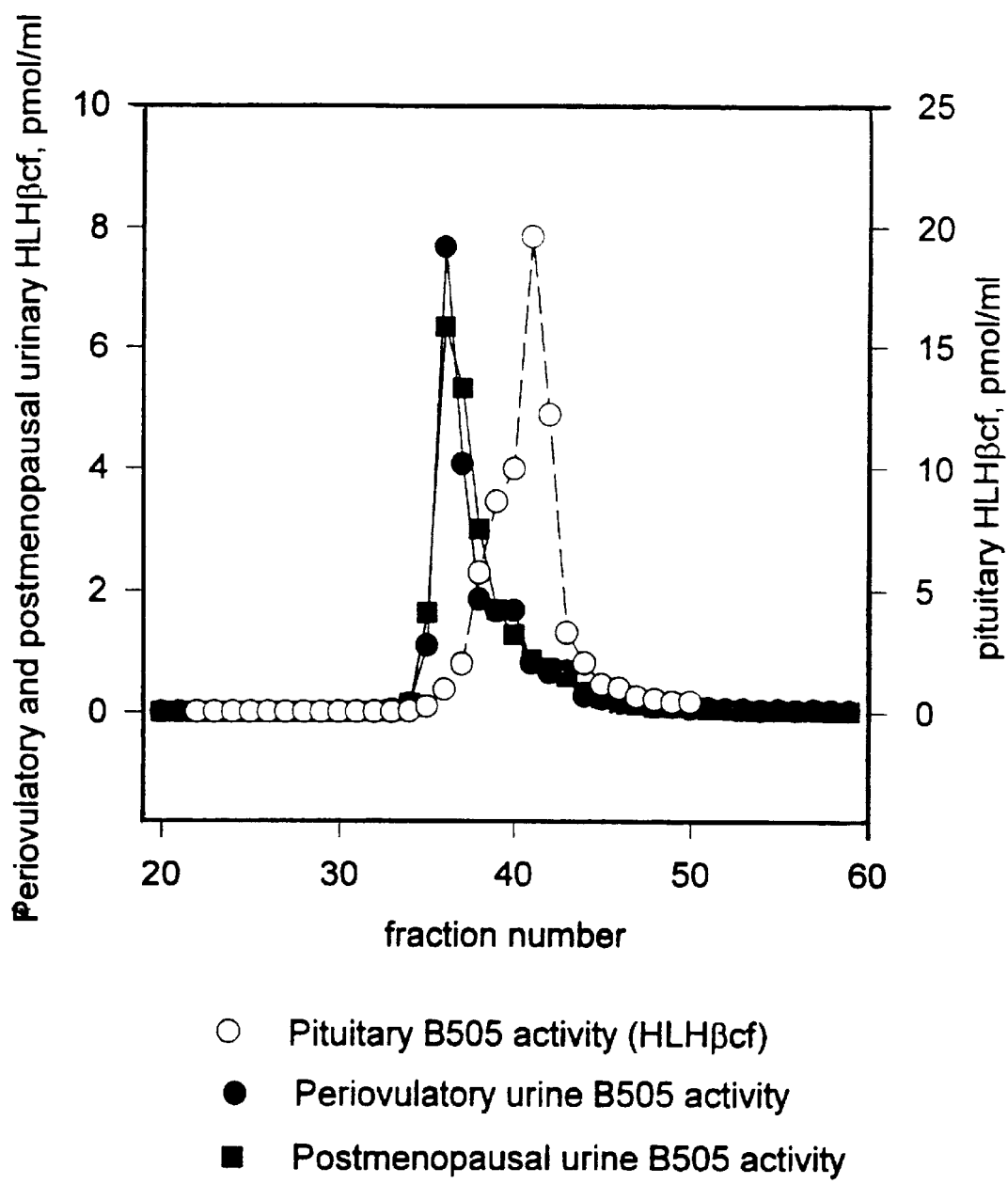

Analysis of urine fractions after gel filtration on the Superose 12 column using the B505-B503 assay indicated What all hLHbcf activity appeared in one low molecular weight peak (10 000 Da). Upon reverse phase chromatography of the gel filtered hLHbcf-containing pooled fractions on a Vydac C-4 column, the elution position of both periovulatory and postmenopausal hLHbcf immunoreactivity were identical, while that of the pituitary-derived material appeared 4 fractions later (FIG. 2). This indicates that the structure of the pituitary-derived hLHbcf is likely to be different from the material present in the urine of both pre and postmenopausal women and that the urinary form of the hLHbcf is substantially the same in women of any age.

Mass Spectrometric Analysis of the Pituitary hLHbcf

The pituitary form of hLHbcf was the immunogen for the antibodies used in these studies and was our reference standard. Understanding how its structure may differ from the urinary form being measured is important. The difference in reverse phase elution profile of the pituitary and urinary forms of the hLHβcf led us to explore such differences in structure between the pituitary and urinary forms of this molecule. We have not yet isolated the urinary form and so, concentrated on the pituitary isoform. We subjected the pituitary material to reduction and carboxymethylation (RCM) and separated the constituent polypeptide chains by reverse phase HPLC as described earlier for the hCGβcf (Birken et al., 1988). A combination of Edman amino terminal sequence analysis and mass spectrometry permitted unequivocal assignment of the constituent non-glycosylated peptide chains of the pituitary hLHβcf: one RCM chain began at residue 55, as reported earlier (Birken et al., 1993), but was measured as 4 546 Da by mass spectrometry indicating that it terminates at residue 93, CYS. This polypeptide has a theoretical mass of 4 544.83 Da for the RCM form measures. The second non-glycosylated RCM peptide exhibited an amino terminus starting at residue 49 and a size of 5188 Da which corresponds again with a COOH-terminus of CYS 93 with a theoretical mass of 5190 Da. This is in sharp contrast to the structure of the hCGbcf which does not include CYS 93. The glycosylated peptide, previously determined to be residues 6–40, was not subjected to mass spectrometry because of its carbohydrate heterogeneity and difficulty in isolation of its RCM form. Mass spectrometry was also performed on the native pituitary form of the hLHβcf as compared to the hCGβcf and both displayed similar sizes in the range of 9 000–10 000 Da. Theoretical calculation of the mass of each fragment indicates that both should be about 10 000 Da only if the hLHβcf single carbohydrate chain is essentially intact while the two carbohydrate groups of the hCGβcf are known to be trimmed down to the mannose cores (Blithe et al., 1988): hLHβcf is composed of 6–40 (3927 Da)+49–93 (4896 Da) or +55–93 (4249 Da)+full carbohydrate group with sulfate (2093 Da) The theoretical sizes of the hLHβcf are 10 916 Da for the form with the longer non-glycosylated peptide and 10 269 Da for the form with the shorter peptide. The hCGβcf is theoretically 10 347 Da. The actual mass spectrometry results yielded slightly smaller forms of both fragments but proved that the pituitary hLHβcf is likely to contain close to a complete carbohydrate group and not the trimmed down groups of the urinary hCGβcf. In fact, the hLHbcf was predominantly one broad peak on mass-spectrometry while the hCGbcf appears as two distinct broad peaks, reflecting variation in trimming of its carbohydrate group. Further evidence that the pituitary hLHβcf contains a carbohydrate group similar to its parent hLHβ subunit was provided by the sialic and sulfate analysis which indicated that both were present in the core. Therefore, we can conclude that within the pituitary, roteolytic enzymes exist to produce the hLHβcf, but glycosidases are not active in this metabolism as they are in the case of the hCGbcf. However, the different HPLC position of the urinary form of this molecule may be due to such carbohydrate modification. Definitive proof of the structure of the urinary form of the hLHβcf awaits its isolation.

Stability of Urinary hLHbcf

The results obtained from the repeated freeze/thaw cycles indicated no statistically significant change from control for up to 40 freeze/thaw cycles (P=0.214) . There was no statistically significant change from control in immunodetectable hLHbcf at either 4° C. or room temperature for up for 29 days. At 37° C., the molecule was stable for 14 days but showed a statistically reliable change after 29 days (P<0.05).

Discussion

There is a considerable literature documenting the difficulty in obtaining accurate measurements, or even detecting at all, circulating hLH by immunoassay, although normal levels may be detected by bioassay in the same subjects (Pettersson et al., 1991; Martin-Du-Pan et al., 1994; Barbe et al., 1995; Pettersson and Soderholm, 1991). The causes of this phenomenon are thought to include genetic variants of the hLH molecule, leading to loss of expression of an epitope, or to the well documented existence of multiple circulating isoforms of hLH, which may have differential recognition by the monoclonal antibodies employed in the assay, as is the case with nicking of the hCG beta subunit, which results in nearly complete ablation of binding to many monoclonal antibodies specific for the intact hCG molecule.

An analogous situation can exist in urine, in cases in which antibodies that are used for hLH detection in urine cross-react with free beta subunit and/or hLHbcf. This cross-reactivity results in obscuring the real hLH surge, even when urinary steroid measurements indicate that ovulation has occured (Wilcox et al., 1987).

Although hLHbcf, a stable hLH related molecule, is not capable of accurately segmenting the menstrual cycle because of its variable day peak occurrence, nevertheless it appears capable of confirming that the midcycle surge of hLH has in fact occurred.

This communication describes the behavior or hLHbcf, a molecule presumably derived from hLH free beta subunit, which we show to be present in both men and women, sometimes at high levels, and describes how it can confound the interpretation of hLH measurements in urine.

In a first publication concerning pituitary hLHbcf antibodies a large peak of immunoreactivity in urine which followed the hLH surge by 1–3 days was reported (Kovalevskaya et al., 1995). It was observed that monoclonal antibodies to pituitary hLHbcf shared at least 2 epitopes with the analogous protein in urine. This immunologically similar urinary molecule has been called urinary hLHbcf.

In the present study 15 cycles of normally ovulating women have been investigated. Data presented in FIG. 9 show the position and concentration of urinary hLHbcf as compared with the appearance of hLH and hLHb in the urine. Additionally we measured hCGbcf, because the first evidence of hLHbcf had been obtained using a polyclonal antibody with primary specificity to hCGbcf (Iles et al., 1992; Neven et al., 1993). Using monoclonal antibodies specific to hCGbcf, we found that there is very low peak of hCGbcf exactly coincident with hLHbcf (FIG. 9). This signal may be accounted for by the 1–2% hLHbcf cross-reactivity in the assay for hCGbcf (Birken et al., 1996a). Antibodies to hCGbcf which were used by Neven (Neven et al., 1993) and Iles (Iles et al., 1992) cross-react with hLHbcf to an extent which allowed these investigators to detect hLHbcf. The lag time between the appearance of intact hLH or hLHb and hLHbcf suggests that, analogously with hCGbcf, hLHbcf is a degradation product of the intact hormone or of its free beta subunit.

Irregular pulsations of urine hLHbcf outside of the main periovulatory surge (FIG. 10) probably reflect spikes of hLH in blood, which are a consequence of the pulsatile release of GnRH (Knobil, 1988; Van Dieten and De Koning, 1995; Shoham et al., 1995). Spikes or hLH are also observed in urine, but at a much lower amplitude, than those of hLHbcf.

Problems associated with the detection of a discrete hLH surge in urine have been reported by Edwards (Edwards et al., 1980). They found an intact hLH surge in 68/79 patients employing a hemagglutination assay and confirming in some cases with a hLH radioimmunoassay. In eleven cases a satisfactory hLH surge was not obtained These investigators also noted a diurnal variation in the timing of the hLH surge, demonstrating that an inadequately timed collection protocol might be implicated in this difficulty. In the course of the present investigation, we also observed several cycles which did not produce a detectable intact hLH signal even though urinary steroid profiles indicated that ovulation had occurred. Two representative cycles are presented in FIGS. 7a–7d. They illustrate the same pattern of hLHbcf as seen in cycles with a measurable intact hLH value. This surge commenced on the day following ovulation as judged by urinary steroid metabolites (Baird et al., 1991), and it peaked over the succeeding one to three days indicating that a normal midcycle surge of intact hLH can be confirmed by urinary hLHbcf measurements. Our results suggest that an assay incorporating the detection of all three urinary analytes would provide the most sensitive detection of periovulatory hLH. However, although hLHb is most often observed to peak coincident with the intact molecule (FIG. 9), it appears that it can occasionally occur one day earlier (FIG. 8 in Kovalevskaya et al., 1995). On the other hand, hLHbcf, usually peaked over 1–3 days later than the intact molecule (FIG. 5) and this midcycle peak of hLHbcf has beer, detected in all four cycles in which there was undetectable intact hLH in the urine (FIG. 7). The intact hormone may have been completely cleared by an alternative pathway. The alternative pathway would be clearance through the liver, which has receptors or asialoglycoproteins and sulphated glycoproteins (Kawasaki and Ashwell, 1976; Steer and Ashwell, 1986; Weiss and Ashwell, 1989; Flete et al., 1991). The intact hormone may have dissociated completely into subunits or have been totally degraded into fragment prior to excretion as is the case with HCG, i.e. administration of the intact HCG mo9lecule to either men or non-pregnant women results in the appearance of HCGβcf in the urine (Nisula et al., 1989). Finally, the antibodies used in these measurements, which were raised to tthe pituitary form of LH, may have failed to recognize the urinary isoform of LH present in the sample.

Some further insight into this issue is provided by the comparison of hormone profiles in blood and urine for two cycles from the same patient (one cycle is presented in FIG. 11). Although our lack of an adequate number of serum samples did not permit us to confirm the synchrony of serum and urine hLH secretion as reported by Cano and Aliada (Cano et al., 1995), our data is nevertheless supportive of their observation that intact hLH in blood and urine peak very nearly simultaneously.

The basal level (i.e. follicular level) of hLHbcf in normally cycling women was similar to the level which we obtained for male urine (Table 2). Both of these groups differ markedly from the values obtained for postmenopausal subjects which were characterized both by much higher levels and a wider range of values (FIG. 8). Levels of intact hLH were low in these subjects in both assays for hLH, but there was a substantial quantity of hLHb, perhaps reflecting dissociation of the intact molecule. Only low values of hCGbcf were detected.

There was no significant hLHbcf surge in blood but a substantial hLHbcf surge in urine, supporting the hypothesis that urinary hLHbcf is a product of hLH metabolic processing. The lag time in the appearance of the fragment suggests that it may be a consequence of metabolic processing by the kidney or in some other compartment.

We chose to use two assays for intact hLH measurements (hLH-1 and hLH-2) because, although the hLH-2 assay was highly specific for the intact hLH molecule, it occasionally produced a weak signal in urinary assays. The hLH-1 assay, although less specific for hLH, (some crossreactivity with hCG, Table 3) had a tendency to detect signals of greater amplitude, with a better incidence of detection when applied to urine specimens. Incidently, the hLH-2 assay barely detected hLH in the serum of this subject but detected the urinary form as well as the hLH-1 assay, which performed equally well in both serum and urine. The above observations probably reflect metabolic processing of the hLH which affects epitope presentation upon passage from blood to urine.

Another issue is the structure of the urinary and pituitary forms of hLHbcf. Are they identical or does the urinary variant, presumably arising from the intact hormone, differ in structure? The ultimate answer awaits the isolation and complete sequence and carbohydrate analysis of the urinary form. Although both the pituitary and urinary forms appear to have the same molecular size by gel filtration, on reverse phase HPLC analysis the isoforms differ in their hydrophobicity, with the urinary fragment being more hydrophilic. In contrast, urinary forms of hLHbcf molecules from either pre- or postmenopausal urine concentrates are closely related in structure, as evidenced by identical elution times from the Vydac C-4 column (Figure). Additional structural studies of the pituitary form using a combination of mass-spectrometry and ion chromatography indicate that the pituitary hLHbcf resembles its parent hLHβ In its carbohydrate moiety. This contrasts to the structure of the hCGβcf which has carbohydrate moieties trimmed to their mannose cores. Mass spectrometric analysis indicates that pituitary hLHβcf displays one peak on mass-spectrometry of about 10 000 Da similar to one of the two peaks of the hCGβcf which average 10 000 Da and 9000 Da respectively. The hCGbcf usually displays two bands on non-reduced PAGE which correspond with the two broad peaks observed on mass specrometry (Birken et al., 1988).

Livesey (Livesey et al., 1980; Livesey et al., 1983), Saketos (Saketos et al., 1994) and Kesner (Kesner et al., 1995), among others have all reported significant loss of urinary hLH or hFSH immunoreactivity upon prolonged frozen storage without addition of the cryoprotectant glycerol. Kesner determined that BSA also improved urinary analyte stability for both gonadotropins and urinary steroid metabolites in frozen storage (Kesner et al., 1995). These investigators also determined that both hLH and hFSH were essentially stable for up to two weeks at 4° C., with bacteriostatic additives having no consistent preservative effect. An investigation by de Medeiros concerning the stability of hCGbcf determined that this molecule was stable under a variety of conditions, including extended storage at room temperature, frozen storage, and repeated freeze/thaw cycles (de Medeiros et al., 1991). Again, preservatives, including protease inhibitors, did not affect immunological stability.

Analogous to hCGbcf, with which hLHbcf shares extensive structural homology, endogenous urinary hLHbcf has remarkable epitope stability, especially where contrasted with reports detailing the lack of stability during storage of the parent hLH molecule (Saketos et al., 1994; Livesey et al., 1980; Livesey et al., 1983; Kesner et al., 1995).

There are reports that measurement of the periovulatory surge of hLH in urine instead of blood leads either to errors in the assignment of the day of ovulation or to the inability to detect the surge at all (Kesner et al., 1992; Kesner et al., 1997). The identification of hLHbcf has suggested a possible source of these difficulties. The ambiguity in interpretation of different assay formats for hLH in urine is illustrated in (FIG. 9). Panel A shows the results obtained when IRMA's are used to measure hLH, hLHb, hLHbcf and hCGbcf. As expected, both assays for intact hLH plus the assay for hLH free beta subunit all produce a synchronous peak for their respective analytes. The immunoreactive hLHbcf peaks 1–3 days later and declines over several succeeding days. A small peak of hCGbcf is also evident under the hLHbcf, but most, if not all, of this signal may be ascribed to assay crossreactivity. A different profile is produced when the same urine specimens are analyzed by a polyclonal RIA assay for blood measurements provided by the NHPP (FIG. 9B). Although this assay produces a very satisfactory blood hLH and hLHb profile, because hLHbcf is not detected in significant amounts in blood, the results are less clear when applied to urine. The intact hLH surge now extends over several days (see also similar urinary hLH profiles in ref. (Kesner et al., 1992; Kesner et al., 1997) as examples), as does hLHb, after a two day lag time. This likely indicates that the polyclonal antisera to hLH and hLHb recognize urinary hLHbcf, suggesting that cross reactivity can lead to an incorrect assignment of the day of ovulation. Direct tests with $^{125}$I-hLHbcf indicate that both polyclonal antisera to hLH and hLHb cross react with hLHbcf in an RIA format (FIG. 10). These results demonstrate that such cross-reactivity can lead to an incorrect assignment of the day of ovulation. This problem would not be encountered with these assays as long as their use was restricted measurements in blood, since there is little or no hLHbcf present in this medium.

The data illustrate a potential risk associated with the use of ovulation test kits designed for personal use. Should the antibodies used in their construction detect hormone fragments in addition to the intact molecule the test results could be ambiguous and misleading.

REFERENCES

Birken, S., E. G. Armstrong, M. A. Kolks, L. A. Cole, G. M. Agosto, A. Krichevsky, J. L. Vaitukaitis, and R. E. Canfield. 1988. Structure of the human chorionic gonadotropin beta-subunit fragment from pregnancy urine. *Endocrinology* 123:572–583.

Birken, S., Y. Maydelman, M. A. Gawinowicz, A. Pound, Y. Liu, and A. S. Hartree. 1996. Isolation and characterization of human pituitary chorionic gonadotropin. *Endocrinology* 137:1402–1411.

Birken, S., Y. Chen, M. A. Gawinowicz, J. W. Lustbader, S. Pollak, G. Agosto, R. Buck, and J. O'Connor. 1993a. Separation of nicked human chorionic gonadotropin (hCG), intact hCG, and hCG beta fragment from standard reference preparations and raw urine samples. *Endocrinology* 133:1390–1397.

Birken, S., M. A. Gawinowicz, A. Kardana, and L. A. Cole. 1991. The heterogeneity of human chorionic gonadotropin (hCG). II. Characteristics and origins of nicks in hCG reference standards. *Endocrinology* 129:1551–1558.

Birken, S., Y. Chen, M. A. Gawinowicz, G. M. Agosto, R. E. Canfield, and A. S. Hartree. 1993b. Structure and significance of human luteinizing hormone-beta core fragment purified from human pituitary extracts. *Endocrinology* 133:985–989.

Blithe, D. L., Akar, A H, Wehmann, R E and Nisula, B C. (1988) Purification of beta-core fragment from pregnancy urine and demonstration that its carbohydrate moieties differ from those of native human chorionic gonadotropin-beta. *Endocrinology* 122:173–180.

Burger, H. G. 1994b. Diagnostic role of follicle-stimulating hormone (FSH) measurements during the menopausal transition—an analysis of FSH, oestradiol and inhibin. [Review]. *Eur. J. Endocrinol.* 130:38–42.

Burger, H. G. 1994a. The menopause: when it is all over or is it?. [Review]. *Aust. N. Z. J. Obstet. Gynaecol.* 34:293–295.

Burger, H. G., E. C. Dudley, J. L. Hopper, J. M. Shelley, A. Green, A. Smith, L. Dennerstein, and C. Morse. 1995. The endocrinology of the menopausal transition: a cross-sectional study of a population-based sample. *J. Clin. Endocrinol. Metab.* 80:3537–3545.

Burger, H. G. 1996. The endocrinology of the menopause. [Review]. *Maturitas* 23:129–136.

Burger, H. G., P. G. Farnworth, J. K. Findlay, C. J. Gurusinghe, D. L. Healy, P. Mamers, A. Mason, and D. M. Robertson. 1995. Aspects of current and future inhibin research. [Review]. *Reprod. Fertil. Dev.* 7:97–1002.

Cole L A, Schwartz P E, Wang Y X 1988b. Gynecol Oncol 31:82–90

Cole L A, Wang Y, Elliot M, Latef M, Chambers J T, Chambers S K, Schwartz P E 1988a. Cancer Res 48:1356–1360

Cole L A, Nam J H, Chambers J T, Schwartz P E 1990 Gynecol Oncol 36:391–394 de Medeiros, S. F., F. Amato, and R. J. Norman. 1991. Stability of immunoreactive beta-core fragment of hCG. *Obstet. Gynecol.* 77:53–59.

Hee, J., J. MacNaughton, M. Bangah, and H. G. Bgrger. 1993. Perimenopausal patterns of gonadotrophins, immunoreactive inhibin, oestradiol and progesterone. *Maturitas* 18:9–20

Iles, R. K., C. L. Lee, I. Howes, S. Davies, R. Edwards, and T. Chard. 1992. Immunoreactive beta-core-like material in normal postmenopausal urine: human chorionic gonadotrophin or LH origin? Evidence for the existence of LH core. *J. Endocrinol.* 133:459–466.

Kato Y. and Braunstein G. D. (1988) Beta-core fragment is a major form of immunoreactive urinary chorionic gonadotropin in human pregnancy. *J. Clin. Endocrinol. Metab.* 66:1197–1201.

Kovalevskaya, G., S. Birken, J. O'Connor, J. Schlatterer, Y. Maydelman, and R. Canfield. 1995. HLH beta core fragment immunoreactivity in the urine of ovulating women: a sensitive and specific immunometric assay for its detection. *Endocrine* 3:881–887.

Krichevsky, A., S. Birken, J. O'Connor, K. Bikel, J. Schlatterer, C. Yi, G. Agosto, and R. Cantield. 1991. Development and characterization of a new, highly specific antibody to the human chorionic gonadotropin-beta fragment. *Endocrinology* 128:1255–1264.

Krichevsky A, Birken S, O'Connor J F, Bikel K, Schlatterer J P and Canfield, R. E. (1994) The development of a panel of monoclonal antibodies to human luteinizing hormone and its application to immunological mapping and two-site assays. *Endocrine* 2: 511–520

Lee, C. L., R. K. Iles, J. H. Shepherd, C. N. Hudson, and T. Chard. 1991. The purification and development of a radioimmunoassay for beta-core fragment of human chorionic gonadotrophin in urine: application as a marker of gynaecological cancer in premenopausal and postmenopausal women. *J. Endocrinol.* 130:481–489.

Metcalf, M. G., R. A. Donald, and J. H. Livesey. 1981. Classification of menstrual cycles in pre- and perimenopausal women. *J. Endocrinol.* 91:1–10.

Metcalf, M. G., R. A. Donald, and J. H. Livesey. 1982. Pituitary-ovarian function before, during and after the menopause: a longitudinal study. *Clin. Endocrinol. (Oxf).* 17:489–494.

Metcalf, M. G. 1979. Incidence of ovulatory cycles in women approaching the menopause. *J. Biosoc. Sci.* 11:39–48.

Metcalf, M. G., R. A. Donald, and J. H. Livesey. 1981. Pituitary-ovarian function in normal women during the menopausal transition. *Clin. Endocrinol. (Oxf).* 14:245–255.

Metcalf, M. G. 1988. The approach of menopause: a New Zealand study. *N. Z. Med. J.* 101:103–106.

Metcalf, M. G. and R. A. Donald. 1979. Fluctuating ovarian function in a perimenopausal women. *N. S. Med. J.* 89:45–47.

Neven, P., R. K. Iles, C. L. Lee, C. N. Hudson, J. H. Shepherd, and T. Chard. 1993. Urinary chorionic gonadotropin subunits and beta-core in nonpregnant women. A study of benign and malignant gynecologic disorders. *Cancer* 71:4124–4130.

Never, P., R. K. Iles, I. Howes, K. Sharma, J. H. Shepherd, R. Edwards, W. P. Collins, and T. Chard. 1993. Substantial urinary concentrations of material resembling beta-core fragment of chorionic gonadotropin beta-subunit in midmenstrual cycle. *Clin. Chem.* 39:1857–1860.

O'Connor, J. F., J. P. Schlatterer, S. Birken, A. Krichevsky, E. G. Armstrong, D. McMahon, and R. E. Canfield. 1988. Development of highly sensitive immunoassays to measure human chorionic gonadotropin, its beta-subunit, and beta core fragment in the urine: application to malignancies. *Cancer Res.* 48:1361–1366.

O'Connor, J. F., S. Birken, J. W. Lustbader, A. Krichevsky, Y. Chen, and R. E. Canfield. 1994. Recent advances in the chemistry and immunochemistry of human chorionic gonadotropin: impact on clinical measurements. [Review]. *Endocr. Rev.* 15:650–683.

Santoro, N., J. R. Brown, T. Adel, and J. H. Skurnick. 1996. Characterization of reproductive hormonal dynamics in the perimenopause. *J. Clin. Endocrinol. Metab.* 81:1495–1501.

Schroeder, H. R. and Halter, C. M. (1983) Specificity of human beta-choriogonadotropin assays for the hormone and for an immunoreactive fragment present in urine during normal pregnancy. *Clinical Chemistry.* 29:667–671.

Stenman, U. H., J. M. Bidart, S. Birken, K. Mann, B. Nisula, and J. O'Connor. 1993. Standardization of protein immunoprocedures. Choriogonadotropin (CG). *Scand. J. Clin. Lab. Invest. Suppl.* 216:42–78.

References for Example 4

1. Monjan A A, Bellino F L, Ory M G, Sherman S. Weiss S. Conference on menopause. Research recommendations. Exp.Gerontol. 1994;29:525–528.
2. Prior J C. Perimenopause: the complex endocrinology of the menopausal transition. Endocr.Rev. 1998;19:397–428.
3. Burger H G. Diagnostic role of follicle-stimulating hormone (FSH) measurements during the menopausal transition—an analysis of FSH, oestradiol and inhibin. Eur.J.Endocrinol. 1994;130:38–42.
4. Burger H G. The endocrinology of the menopause. Maturitas 1996;23:129–136.
5. Stellato R K, Crawford S L, McKinlay S M, Longcope C. Can Follicle-Stimulating Hormone Status Be Used To Define Menopausal Status? Endocrine Practice 1998;4:137–141.
6. Reame N E, Kelche R P, Beitins I Z, Yu M Y, Zawacki C M, Padmanabhan V. Age effects of follicle-stimulating hormone and pulsatile luteinizing hormone secretion across the menstrual cycle of premenopausal women. J Clin Endocrinol.Metab. 1996;81:1512–1518.
7. Rannevik G, Jeppsson S, Johnell O, Bjerre E, Laurell-Borulf Y, Svanberg L. A longitudinal study of the perimenopausal transition: altered profiles of steroid and pituitary hormones, SHBCG and bone mineral density. Maturitas 1995;21:103–113.
8. O'Connor J F, Kovalevskaya G, Birken S, et al. The expression of the urinary forms of human luteinizing hormone beta fragment in various populations as assessed by a specific immunoradiometric assay. Hum.Reprod. 1998;13:826–835.
9. Birken S, Kovalevskaya G, O'Connor J. Metabolism of hCG and hLH to multiple urinary forms. Mol.Cell Endocrinol. 1996;125:121–131.
10. Birken S, Chen Y, Gawinowicz M A, Agosto G M, Canfield R E, Hartree A S. Structure and significance of human luteinizing hormone-beta core fragment purified from human pituitary extracts. Endocrinology 1993;133:985–989.
11. Santoro N, Brown J R, Adel T., Skurnick J H. Characterization of reproductive hormonal dynamics in the perimenopause. J.Clin.Endocrinol.Metab. 1996;81:1495–1501.
12. Brown J R, Skurnick J H, Sharma N, Adel T, Santoro N. Frequent intermittent ovarian function in women with premature menopause: a longitudinal study. Endocrine J 1993;1:467–474.
13. Kovalevskaya G, Birken S, O'Connor J, Schlatterer J P, Maydelman Y, Canfield R E. HLH β core fragment immunoreactivity in the urine of ovulating women: a sensitive and specific immunometric assay for its detection. Endocrine 1995;3:881–887.
14. Taussky H H. A microcolorimetric determination of creatinine in urine by the Jaffe reaction. J Biol Chem 1954;208:853–861.
15. Saketos M, Sharma N, Adel T, Raguwanshi M, Santoro N. Utility of time-resolved fluorescent immunoassay technique for urinary gonadotropin measurement. Clin Chem 1994;40:749–753.
16. Livesey J H, Roud H K, Metcalf M G, Donald R A. Glycerol prevents loss of immunoreactive follicle-stimulating hormone and luteinizing hormone from frozen urine. J.Endocrinol. 1983;98:381–384.
17. Guthrie J R, Dennerstein L, Hopper J L, Burger H G. Hot flushes, menstrual status, and hormone levels in a population-based sample of midlife women. Obstet.Gynecol. 1996;88:437–442.
18. Hegde B M. Change of life—menopause. J.Indian Med.Assoc. 1995;93:460–461.
19. Metcalf M G. The approach of menopause: a New Zealand study. N.Z.Med.J. 1988;101:103–106.
20. Santoro N, Banwell T, Tortoriello D, Lieman H, Adel T, Skurnick J. Effects of aging and gonadal failure on the hypothalamic-pituitary axis in women. Am.J Obstet.Gynecol. 1998;178:732–741.
21. Wehmann R E, Blithe D L, Flack M R, Nisula B C. Metabolic clearance rate and urinary clearance of purified beta-core. J.Clin.Endocrinol.Metab. 1989;69:510–517.
22. Udagawa A, Okamoto T, Nomura S, Matsuo K, Suzuki H, Mizutani S. Human chorionic gonadotropin β-core fragment is present in the human placenta. Mol.Cell.Endocrinol. 1998;139:171–178.

References for Example 6

Baird, D. D., Weinberg, C. R., Wilcox, A. J., McConnaughey, D. R. and Musey, P. I. (1991) Using the ratio of urinary oestrogen and progesterone metabolites to estimate day of ovulation. *Stat. Med.,* 10, 255–266.
Barbe, F., Legagneur, H., Watrin, V., Klein, M. and Badonnel, Y. (1995) Undetectable luteinizing hormone levels using a monoclonal immunometric assay. *J. Endocrinol. Invest.,* 18, 806–808.
Birken, S., Armstrong, E. G., Kolks, M. A., Cole, L. A., Agosto, G. M., Krichevsky, A., Vaitukaitis, J. L. and Canfield, R. E. (1988) Structure of the human chorionic gonadotropin beta-subunit fragment from pregnancy urine. *Endocrinology,* 123, 572–583.
Birken, S., Chen, Y., Gawinowicz, M. A., Agosto, G. M., Canfield, R. E. and Hartree, A. S. (1993) Structure and significance of human luteinizing hormone-beta core fragment purified from human pituitary extracts. *Endocrinology,* 133, 985–989.
Birken, S., Kovalevskaya, G. and O'Connor, J. (1996a) Metabolism of hCG and hLH to multiple urinary forms. *Molecular Cellular Endocrinology,* 125, 121–131.
Birken, S., Maydelman, Y., Gawinowicz, M. A., Pound, A., Liu, Y. and Hartree, A. S. (1996) Isolation and characterization of human pituitary chorionic gonadotropin. *Endocrinology,* 137, 1402–1411.
Blithe, D. L., Akar, A. H., Wehmann, R. E. and Nisula, B. C. (1988) Purification of beta-core fragment from pregnancy urine and demonstration that its carbohydrate moieties differ from those of native human chorionic gonadotropin-beta. *Endocrinology,* 122, 173–180.
Cano, A. and Aliaga, R. (1995) Characteristics of urinary luteinizing hormone (LH) during the induction of LH surges of different magnitude in blood. *Hum. Reprod.,* 10, 63–67.
Costagliola, S., Niccoli, P. and Carayon, P. (1994) Glycoprotein hormone isomorphism and assay discrepancy: the paradigm of luteinizing hormone (LH). [Review]. *J. Endocrinol. Invest.,* 17, 291–299.
de Medeiros, S. F., Amato, F. and Norman, R. J. (1991) Stability of immunoreactive beta-core fragment of hCG. *Obstet. Gynecol.,* 77, 53–59.
Edwards, R. G., Steptoe, P. C. and Purdy, J. M. (1980) Establishing full-term human pregnancies using cleaving embryos grown in vitro. *Br. J. Obstet. Gynaecol.,* 87, 737–756.
Flete, D., Srivastava V., Hindsgaul O. and Baenziger, J. U. (1991) A hepatic reticuloendothelial cell receptor specific for SO4-4GalNAc beta 1,4GlcNAc beta 1,2Man alpha that mediates rapid clearance of lutropin [see comments]. *Cell,* 67, 1103–1110.
Iles, R. K., Lee, C. L., Howes, I., Davies, S., Edwards, R. and Chard, T. (1992) Immunoreactive beta-core-like material in normal postmenopausal urine: human chorionic gonadotrophin or LH origin? Evidence for the existence of LH core. *J. Endocrinol.,* 133, 459–466.
Kato, Y. and Braunstein, G. D. (1988) Beta-core fragment is a major form of immunoreactive urinary chorionic gonadotropin in human pregnancy. *J. Clin. Endcrinol. Metab.,* 66, 1197–1201.
Kawasaki, T. and Ashwell, G. (1976) Chemical and physical properties of an hepatic membrane protein that specifically binds asialoglycoproteins. *J. Biol. Chem.,* 251, 1296–1302.
Kesner, J. S., Knecht, E. A., Krieg, E. F., Wilcox, A. J. and O'Connor, J. F. (1997) Detecting previously undetectable preovulatory luteinizing hormone surges in urine. *Hum. Reprod.,* In Press.
Kesner, J. S., Knecht, E. A. and Krieg, E. F., Jr. (1995) Stability of urinary female reproductive hormones stored under various conditions. *Reprod. Toxicol,* 9, 239–244.
Kesner, J. S., Wright, D. M., Schrader, S. M., Chin, N. W. and Krieg, E. F., Jr. (1992) Methods of monitoring menstrual function in field studies: efficacy of methods. *Reprod. Toxicol.,* 6, 385–400.
Knobil, E. (1988) The hypothalamic gonadotrophic hormone releasing hormone (GnRH) pulse generator in the rhesus monkey and its neuroendocrine control. [Review] [19 refs]. *Hum. Reprod.,* 3, 29–31.
Kovalevskaya, G., Birken, S., O'Connor, J., Schlatterer, J., Maydelman, Y. and Canfield, R. (1995) HLH beta core fragment in the urine of ovulating women: a sensitive and specific immunometric assay for its detection. *Endocrine,* 3, 881–887.
Krichevsky, A., Birken, S., O'Connor, J., Bikel, K., Schlatterer, J., Yi, C., Agosto, G. and Canfield, R. (1991) Development and characterization of a new, highly specific antibody to the human chorionic gonadotropin-beta fragment. *Endocrinology,* 128, 1255–1264.
Krichevsky, A., Birken, S., O'Connor, J., Bikel, K., Schlatterer, J. and Canfield, R. (1994) The development of a panel of monoclonal antibodies to human luteinizing hormone and its application to immunological mapping and two-site assays. *Endocrine,* 2, 511–520.
Livesey, J. H., Hodgkinson, S. C., Roud, H. P. and Donald, R. A. (1980) Effect of time, temperature and freezing on the stability of immunoreactive LH, FSH, TSH, growth hormone, prolactin and insulin in plasma. *Clin. Biochem.*, 13, 151–155.

Livesey, J. H., Roud, H. K., Metcalf, M. G. and Donald, R. A. (1983) Glycerol prevents loss of immunoreactive follicle-stimulating hormone and luteinizing hormone from frozen urine. *J. Endocrinol.*, 98, 381–384.

Martin-Du-Pan, R. C., Horak, M. and Bischof, P. (1994) Clinical significance of invisible or partially visible luteinizing hormone. *Hum. Reprod*, 9, 1987–1990.

Mitchell, R., Hollis, S., Crowley, V., McLoughlin, J., Peers, N. and Robertson, W. R. (1995) Immunometric assays of luteinizing hormone (LH): differences in recognition of plasma LH by anti-intact and beta-subunit-specific antibodies in various physiological and pathophysiological situations. *Clin. Chem.*, 41, Pt 1):1139–45.

Munro, C. J., Stabenfeldt, G. H., Cragun, J. R., Addiego, L. A., Overstreet, J. W. and Lasley, B. L. (1991) Relationship of serum estradiol and progesterone concentrations to the excretion profiles of their major urinary metabolites as measured by enzyme immunoassay and radioimmunoassay. *Clin. Chem.*, 37, 838–844.

Neven, P., Iles, R. K., Howes, I., Sharma, K., Shepherd, J. H., Edwards, R., Collins, W. P. and Chard, T. (1993) Substantial urinary concentrations of material resembling beta-core fragment of chorionic gonadotropin beta-subunit in mid-menstrual cycle. *Clin. Chem.*, 39, 1857–1860.

Nisula, B. C., Blithe, D. L., Akar, A., Lefort, G. and Wehmann, R. E. (1989) Metabolic fate of human chori-ogonadotropin. [Review], *J. Steroid Biochem.*, 33, 733–737.

O'Connor, J. F., Birken, S., Lustbader, J. W., Krichevsky, A., Chen, Y. and Canfield, R. E. (1994) Recent advances in the chemistry and immunochemistry of human chorionic gonadotropin: impact on clinical measurements. [Review]. *Endocr. Rev.*, 15, 650–683.

Pettersson, K., Ding, Y. Q. and Huhtaniemi, I. (1991) Monoclonal antibody-based discrepancies between two-site immunometric tests for lutropin. *Clin. Chem.*, 37, Pt 1):1745–8.

Pettersson, K., Ding, Y. Q. and Huhtaniemi, I. (1992) An immunologically anomalous luteinizing hormone variant in a healthy woman. *J. Clin. Endocrinol. Metab.*, 74, 164–171.

Pettersson, K. S. and Soderholm, J. R. (1991) Individual differences in lutropin immunoreactivity revealed by monoclonal antibodies [see comments]. *Clin. Chem.*, 37, 333–340.

Saketos, M., Sharma, N., Adel, T., Raghuwanshi, M. and Santoro, N. (1994) Evalution of time-resolved immunof-luorometric assay and specimen storage conditions for measuring gonadotropins. *Clin Chem.*, 40, 749–753.

Schroeder, H. R. and Halter, C. M. (1983) Specificity of human beta-choriogonadotropin assays for the hormone and for an immunoreactive fragment present in urine during normal pregnancy. *Clinical. Chemistry.* 29, 667–671.

Shoham, Z., Schacter, M., Loumaye, E., Weissman, A., MacNamee, M. and Insler, V. (1995) The luteinizing hormone surge—the final stage in ovulation induction: modern aspects of ovulation triggering. [Review]. *Fertil. Steril.*, 64, 237–251.

Steer, C. J. and Ashwell, G. (1986) Hepatic membrane receptors for glycoproteins. [Review]. *Prog. Liver Dis.*, 8, 99–123.

Taussky, H. H. (1954) A microcolorimetric determination of creatinine in urine by the Jaffe reaction. *J. Biol. Chem.*, 208, 853–861.

Van Dieten, J. A. M. J. and De Koning, J. (1995) From basal luteinizing hormone (LH) concentrations to the pre-ovulatory LH surge: Titration of the physiological effect of gonadotrophin surge-inhibiting attenuating factor. *Hum. Reprod.*, 10, 3110–3116.

Weiss, P. and Ashwell, G. (1989) The asialoglycoprotein receptor: properties and modulation by ligand. [Review], *Prog. Clin. Biol. Res.*, 300, 169–184.

Westhoff, C., Levin, B., Ladd, G. and O'Connor, J. (1992) Sources of variability in normal CA 125 levels. *Cancer Epidemiology,. Biomarkers. &. Prevention.*, 1, 357–359.

Wilcox, A. J., Baird, D. D., Weinberg, C. R., Armstrong, E. G., Musey, P. I., Wehmann, R. E. and Canfield, R. E. (1987) The use of biochemical assays in epidemiologic studies ot reproduction. *Environ. Health Perspect.*, 75, 29–35.

---

What is claimed is:

1. A method for determining the temporal proximity to or distance from the onset of menopause in a perimenopausal female subject comprising the steps of:
   (a) contacting a urine sample obtained from the subject during the follicular phase of menses with an antibody which specifically binds to hLHβcf without substantially cross-reacting with hLH, hLHβ or hCGβcf, under conditions permitting formation of a complex between the antibody and hLHβcf;
   (b) measuring the amount of complex formed, so as to thereby determine the amount of hLHβcf in the sample; and
   (c) comparing the amount of hLHβcf in the subject's sample determined in step (b) with either (i) the amount of hLHβcf determined for a sample from a subject known to be postmenopausal or (ii) the amount of hLHβcf determined for a sample from a subject known to be premenopausal, wherein an amount of hLHβcf in the sample similar to the amount of hLHβcf in the postmenopausal sample or dissimilar to the amount of hLHβcf in the premenopausal sample indicates temporal proximity to the onset of menopause, and an amount of hLHβcf in the sample similar to the amount of hLHβcf in the premenopausal sample or dissimilar to the amount of hLHβcf in the postmenopausal sample indicates temporal distance from the onset of menopause in the subject.

2. The method of claim 1, wherein in step (a) the antibody specifically binds to a region of hLHβcf comprising a protein moiety or both protein and carbohydrate moieties.

3. The method of claim 1, wherein the antibody of step (a) is monoclonal antibody B505 produced by the hybridoma cell line B505 deposited with the American Type Culture Collection under Designation No. HB-12000.

4. The method of claim 1, wherein in step (a) the antibody is bound to a solid support and in step (b) the amount of complex formed is measured by contacting the complex with a second antibody which binds to the complex and which is labeled with a detectable marker.

5. The method of claim 1, wherein the urine sample is a first morning void urine sample, an aggregate sample of the first morning void urine samples for at least two consecutive days, an aggregate sample of the first morning void urine samples for five or more consecutive days, or a collection of all consecutive urinations obtained within a 24–48 hour time period.

6. A method for determining the temporal proximity to or distance from the onset of menopause in a perimenopausal female subject comprising the steps of:
   (a) contacting a urine sample obtained from the subject during the follicular phase of menses with a capturing antibody which specifically binds to hLHβcf without substantially cross-reacting with hLH, hLHβ or hCGβcf, under conditions permitting binding of the antibody with any hLHβcf present in the sample wherein the capturing antibody is bound to a matrix;
   (b) separating hLHβcf bound to the capturing antibody from hLHβcf not so bound;
   (c) contacting the bound hLHβcf with a second antibody which specifically binds to the bound hLHβcf without cross-reacting with hLH, hLHβ or hCGβcf, under conditions permitting binding of the second antibody to the bound hLHβcf;
   (d) measuring the amount of the second antibody bound to the bound hLHβcf, so as to thereby determine the amount of hLHβcf in the sample; and
   (e) comparing the amount of hLHβcf in the subject's sample determined in step (d) with either (i) the amount of hLHβcf determined for a sample from a subject known to be postmenopausal or (ii) the amount of hLHβcf determined for a sample from a subject known to be premenopausal, wherein an amount of hLHβcf in the sample similar to the amount of hLHβcf in the postmenopausal sample or dissimilar to the amount of hLHβcf in the premenopausal sample indicates temporal proximity to the onset of menopause, and an amount of hLHβcf in the sample similar to the amount of hLHβcf in the premenopausal sample or dissimilar to the amount of hLHβcf in the postmenopausal sample indicates temporal distance from the onset of menopause in the subject.

7. The method of claim 6 wherein in step (a), the capturing antibody specifically binds to a region of hLHβcf comprising a protein moiety or both a protein and a carbohydrate moiety.

8. The method of claim 7, wherein the capturing antibody is monoclonal antibody B505 produced by the hybridoma cell line B505 deposited with the American Type Culture Collection under Designation No. HB-12000.

9. The method of claim 6, wherein separating the bound hLHβcf from unbound hLHβcf comprises:
   (a) removing the sample from contact with the matrix; and
   (b) washing the matrix with an appropriate buffer to remove unbound hLHβcf.

10. The method of claim 6, wherein the urine sample is a first morning void urine sample, an aggregate sample of the first morning void urine samples for at least two consecutive days, an aggregate sample of the first morning void urine samples for five or more consecutive days, or a collection of all consecutive urinations obtained within a 24–48 hour time period.

11. The method of claim 6, wherein the second antibody is labeled with a detectable marker and is monoclonal antibody B503 or B504 produced by the hybridoma cell lines B503 and B504 deposited with the American Type Culture Collection under Designation Nos. HB-11999 and HB-12002, repectively.

* * * * *

SEQUENCE LISTING

```
<160> NUMBER OF SEQ ID NOS:  2

<210> SEQ ID NO 1
<211> LENGTH: 122
<212> TYPE: PRT
<213> ORGANISM: Homo sapiens

<400> SEQUENCE: 1

Ser Arg Glu Pro Leu Arg Pro Trp Cys His Pro Ile Asn Ala Ile Leu
 1               5                  10                  15

Ala Val Glu Lys Glu Gly Cys Pro Val Cys Ile Thr Val Asn Thr Thr
            20                  25                  30

Ile Cys Ala Gly Tyr Cys Pro Thr Met Met Arg Val Leu Gln Ala Val
        35                  40                  45

Leu Pro Pro Leu Pro Gln Val Val Cys Thr Tyr Arg Asp Val Arg Phe
    50                  55                  60
```

-continued

```
Glu Ser Ile Arg Leu Pro Gly Cys Pro Arg Gly Val Asp Pro Val Val
 65                  70                  75                  80

Ser Phe Pro Val Ala Leu Ser Cys Arg Cys Gly Pro Cys Arg Arg Ser
                 85                  90                  95

Thr Ser Asp Cys Gly Gly Pro Lys Asp His Pro Leu Thr Cys Asp His
            100                 105                 110

Pro Gln Pro Gln Leu Ser Gly Leu Leu Phe
        115                 120

<210> SEQ ID NO 2
<211> LENGTH: 80
<212> TYPE: PRT
<213> ORGANISM: Homo sapiens

<400> SEQUENCE: 2

Arg Pro Trp Cys His Pro Ile Asn Ala Ile Leu Ala Val Glu Lys Glu
  1               5                  10                  15

Gly Cys Pro Val Cys Ile Thr Val Asn Thr Thr Ile Cys Ala Gly Tyr
             20                  25                  30

Cys Pro Thr Leu Pro Pro Leu Pro Gln Val Val Cys Thr Tyr Arg Asp
             35                  40                  45

Val Arg Phe Glu Ser Ile Arg Leu Pro Gly Cys Pro Arg Gly Val Asp
         50                  55                  60

Pro Val Val Ser Phe Pro Val Ala Leu Ser Cys Arg Cys Gly Pro Cys
 65                  70                  75                  80
```